US012616701B2

(12) United States Patent
Lapido et al.

(10) Patent No.: US 12,616,701 B2
(45) Date of Patent: May 5, 2026

(54) SOLID STATE FORMS OF RESMETIROM

(71) Applicant: ASSIA CHEMICAL INDUSTRIES LTD., Tel Aviv (IL)

(72) Inventors: Polina Lapido, Rishon Lezion (IL); Jenny Goldshtein, Netanya (IL); Vitaly Krimer, Petah-Tikva (IL); Doron Rudik, Modi'in (IL)

(73) Assignee: ASSIA CHEMICAL INDUSTRIES LTD, Tel Aviv (IL)

( * ) Notice: Subject to any disclaimer, the term of this patent is extended or adjusted under 35 U.S.C. 154(b) by 457 days.

(21) Appl. No.: 18/029,962

(22) PCT Filed: Oct. 19, 2021

(86) PCT No.: PCT/US2021/055507
§ 371 (c)(1),
(2) Date: Apr. 3, 2023

(87) PCT Pub. No.: WO2022/086894
PCT Pub. Date: Apr. 28, 2022

(65) Prior Publication Data
US 2023/0364099 A1      Nov. 16, 2023

Related U.S. Application Data

(60) Provisional application No. 63/208,032, filed on Jun. 8, 2021, provisional application No. 63/158,540, filed on Mar. 9, 2021, provisional application No. 63/146,776, filed on Feb. 8, 2021, provisional application No. 63/125,425, filed on Dec. 15, 2020, provisional application No. 63/093,396, filed on Oct. 19, 2020.

(51) Int. Cl.
*A61K 31/53*      (2006.01)
*A61K 31/522*      (2006.01)

(52) U.S. Cl.
CPC ............ *A61K 31/53* (2013.01); *A61K 31/522* (2013.01)

(58) Field of Classification Search
CPC .............................. A61K 31/53; A61K 31/522
See application file for complete search history.

(56) References Cited

U.S. PATENT DOCUMENTS 9,266,861 B2      2/2016   Hester, II et al.

FOREIGN PATENT DOCUMENTS

WO      2018075650 A1      4/2018
WO      2020010068 A1      1/2020

OTHER PUBLICATIONS

Office Action issued in corresponding Canadian Application 3,195,789 dated Jun. 5, 2024 (5 pages).
Malamatari et al., "Experimental cocrystal screening and solution based scale-up cocrystallization methods", Advanced Drug Delivery Reviews, vol. 117, 2017, p. 162-177. XP085279598.
Kuminek et al., "Cocrystals to facilitate delivery of poorly soluble compounds beyond-rule-of-5", Advanced Drug Delivery Reviews, vol. 101, Apr. 29, 2016 (Apr. 29, 2016), p. 143-166. XP029580998.
Byrn et al., "Pharmaceutical Solids: A Strategic Approach to Regulatory Considerations", Pharmaceutical Research, vol. 12, No. 7, 1995, p. 945-954. XP055396556.
International Search Report and Written Opinion of the International Searching Authority issued in corresponding application PCT/US2021/055507 mailed Mar. 28, 2022 (29 pages).

*Primary Examiner* — Adam C Milligan
*Assistant Examiner* — Karen Cheng
(74) *Attorney, Agent, or Firm* — Carter, DeLuca & Farrell LLP

(57)      ABSTRACT

The present disclosure encompasses solid state forms of Resmetirom, in embodiments crystalline polymorphs of Resmetirom, processes for preparation thereof, and pharmaceutical compositions thereof.

21 Claims, 45 Drawing Sheets

A characteristic X-ray powder diffraction pattern (XRPD) of Resmetirom Form 2.

A characteristic X-ray powder diffraction pattern (XRPD) of Resmetirom Form 3.

A characteristic X-ray powder diffraction pattern (XRPD) of Resmetirom Form 4.

FIG. 3

A characteristic X-ray powder diffraction pattern (XRPD) of Resmetirom Form 6.

A characteristic X-ray powder diffraction pattern (XRPD) of Resmetirom Form 7.

A characteristic X-ray powder diffraction pattern (XRPD) of Resmetirom Form 8.

A characteristic X-ray powder diffraction pattern (XRPD) of Resmetirom Form 9.

A characteristic X-ray powder diffraction pattern (XRPD) of Resmetirom Form 10.

A characteristic X-ray powder diffraction pattern (XRPD) of Resmetirom Form 13.

A characteristic X-ray powder diffraction pattern (XRPD) of Resmetirom Form 14.

A characteristic X-ray powder diffraction pattern (XRPD) of Resmetirom Form 17.

A characteristic X-ray powder diffraction pattern (XRPD) of Resmetirom Form 19.

A characteristic X-ray powder diffraction pattern (XRPD) of Resmetirom Form 20.

A characteristic X-ray powder diffraction pattern (XRPD) of Resmetirom Form 21.

A characteristic X-ray powder diffraction pattern (XRPD) of Resmetirom Form 22.

A characteristic X-ray powder diffraction pattern (XRPD) of Resmetirom N-methyl morpholine salt Form R1-A.

A characteristic X-ray powder diffraction pattern (XRPD) of Resmetirom piperazine salt Form R2-A.

A characteristic X-ray powder diffraction pattern (XRPD) of Resmetirom L-proline salt Form R3-A.

A characteristic X-ray powder diffraction pattern (XRPD) of Resmetirom benzathine salt Form R4-A.

A characteristic X-ray powder diffraction pattern (XRPD) of Resmetirom: nicotinamide form RC1-A A characteristic X-ray powder diffraction pattern (XRPD) of Resmetirom: caffeine form RC2-A A characteristic X-ray powder diffraction pattern (XRPD) of Resmetirom: caffeine form RC2-B A characteristic X-ray powder diffraction pattern (XRPD) of Resmetirom: 2-picolinic acid form RC3-A A characteristic X-ray powder diffraction pattern (XRPD) of Resmetirom: urea form RC4-A 2Theta (Two Theta) WL=1.54060

A characteristic solid state $^{13}C$ NMR spectrum of Form 20 of Resmetirom (200-100 ppm)

A characteristic solid state $^{13}C$ NMR spectrum of Form 20 of Resmetirom (100-0 ppm)

A characteristic solid state $^{13}C$ NMR spectrum of Form RC1-A of Resmetirom: nicotinamide co-crystal (full range 200-0 ppm)

A characteristic solid state $^{13}C$ NMR spectrum of Form RC1-A of Resmetirom: nicotinamide co-crystal (200-100 ppm)

A characteristic solid state $^{13}C$ NMR spectrum of Form RC1-A of Resmetirom: nicotinamide co-crystal (100-0 ppm)

A characteristic solid state $^{13}C$ NMR spectrum of Form RC2-A of Resmetirom: caffeine co-crystal (full range 200-0 ppm)

A characteristic solid state $^{13}$C NMR spectrum of Form RC2-A of Resmetirom: caffeine co-crystal (200-100 ppm)

A characteristic solid state $^{13}C$ NMR spectrum of Form RC2-A of Resmetirom: caffeine co-crystal (100-0 ppm)

A characteristic solid state $^{13}C$ NMR spectrum of Form RC2-B of Resmetirom: caffeine co-crystal (full range 200-0 ppm)

A characteristic solid state $^{13}C$ NMR spectrum of Form RC2-B of Resmetirom: caffeine co-crystal (200-100 ppm)

-108.7132
-121.5431
-124.4559
-125.5444
-127.7144
-137.4529
-142.6680
-145.8918
-148.6075
-151.7723
-153.6191
-155.3443
-161.1174

A characteristic solid state $^{13}C$ NMR spectrum of Form RC2-B of Resmetirom: caffeine co-crystal (100-0 ppm)

A characteristic solid state $^{13}C$ NMR spectrum of Form R3-A of Resmetirom: L-proline co-crystal (full range 200-0 ppm)

A characteristic solid state $^{13}C$ NMR spectrum of Form R3-A of Resmetirom: L-proline co-crystal (200-100 ppm)

A characteristic solid state $^{13}C$ NMR spectrum of Form R3-A of Resmetirom: L-proline co-crystal (100-0 ppm)

A characteristic solid state $^{13}C$ NMR spectrum of Form R2-A of Resmetirom piperazine salt (full range 200-0 ppm)

A characteristic solid state $^{13}C$ NMR spectrum of Form R2-A of Resmetirom piperazine salt (200-100 ppm)

−113.9555
−120.8267
−122.2744
−125.7700
−128.1585
−129.2705
−137.9587
−143.6799
−151.9887
−153.1423
−161.1165
−164.6073

A characteristic solid state $^{13}C$ NMR spectrum of Form R2-A of Resmetirom piperazine salt (100-0 ppm)

SOLID STATE FORMS OF RESMETIROM

CROSS REFERENCE TO RELATED APPLICATIONS

This application is a National Stage of, and claims priority to and the benefit of, International Patent Application No. PCT/US2021/055507, filed Oct. 19, 2021, which, in turn, claims the benefit of and priority to, U.S. Provisional Application No. 63/093,396, filed on Oct. 19, 2020; U.S. Provisional Application No. 63/125,425, filed on Dec. 15, 2020; U.S. Provisional Application No. 63/146,776, filed on Feb. 8, 2021; U.S. Provisional Application No. 63/158,540, filed on Mar. 9, 2021; and U.S. Provisional Application No. 63/208,032, filed on Jun. 8, 2021, the entire disclosures of each of which are incorporated by reference herein.

FIELD OF THE DISCLOSURE

The present disclosure encompasses solid state forms of Resmetirom, in embodiments crystalline polymorphs of Resmetirom, processes for preparation thereof, and pharmaceutical compositions thereof.

BACKGROUND OF THE DISCLOSURE

Resmetirom, 2-[3,5-dichloro-4-[(6-oxo-5-propan-2-yl-1H-pyridazin-3-yl)oxy]phenyl]-3,5-dioxo-1,2,4-triazine-6-carbonitrile, has the following chemical structure:

Resmetirom is a thyroid hormone receptor (THR) β-selective agonist, and it is developed for the treatment of for non-alcoholic steatohepatitis (NASH), non-alcoholic fatty liver disease (NAFLD) and associated dyslipidemias.

The compound is described in International Publication No. WO 2007/009913. International Publication Nos. WO 2014/043706, WO 2018/075650, WO 2020/010068, WO 2021/063367 and WO 2021/129465 relate to crystalline forms and salts of Resmetirom.

International Publication No. WO 2020/010068 discloses difficulties in preparing co-crystal of Resmetirom with many potential co-formers, and only the glutaric acid co-crystal has been observed, despite extensive efforts.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Resmetirom.

SUMMARY OF THE DISCLOSURE

The present disclosure provides crystalline polymorphs of Resmetirom and salts thereof. The present disclosure further provides crystalline Resmetirom:nicotinamide, Resmetirom:caffeine, Resmetirom: 2-picolinic acid and/or Resmetirom:Urea and solid state forms thereof. The present disclosure further provides Resmetirom N-methyl-morpholine salt, Resmetirom piperazine salt, Resmetirom benzathine salt, Resmetirom:L-proline, and crystalline forms thereof. The present disclosure also provides processes for preparation thereof, and pharmaceutical compositions thereof. The crystalline forms of Resmetirom as well as Resmetirom: nicotinamide, Resmetirom:caffeine, Resmetirom: 2-picolinic acid and/or Resmetirom:Urea and the solid state forms thereof, or Resmetirom N-methyl-morpholine salt, Resmetirom piperazine salt, Resmetirom benzathine salt, Resmetirom:L-proline, and crystalline forms thereof, can be used to prepare other solid state forms of Resmetirom, Resmetirom salts or co-crystals and their solid state forms.

The present disclosure also provides uses of the said solid state forms of Resmetirom and/or salts thereof and of Resmetirom:nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom:L-proline, and crystalline forms thereof, in the preparation of other solid state forms of Resmetirom or salts or co-crystals thereof.

The present disclosure provides crystalline polymorphs of Resmetirom and/or salts thereof and of Resmetirom:nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom:L-proline, and crystalline forms thereof, for use in medicine, including for the treatment of non-alcoholic steatohepatitis (NASH), non-alcoholic fatty liver disease (NAFLD) and/or associated dyslipidemias.

The present disclosure also encompasses the use of crystalline polymorphs of Resmetirom and/or salts thereof and of Resmetirom:nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom:L-proline, and crystalline forms thereof, of the present disclosure for the preparation of pharmaceutical compositions and/or formulations.

In another aspect, the present disclosure provides pharmaceutical compositions comprising crystalline polymorphs of Resmetirom and/or salts thereof and of Resmetirom: nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom:L-proline, and crystalline forms thereof, according to the present disclosure.

The present disclosure includes processes for preparing the above mentioned pharmaceutical compositions. The processes include combining any one or a combination of the crystalline polymorphs of Resmetirom and/or salts thereof and of Resmetirom:nicotinamide, Resmetirom:caffeine, Resmetirom: 2-picolinic acid and/or Resmetirom: Urea, or Resmetirom N-methyl-morpholine salt, Resmetirom piperazine salt, and Resmetirom benzathine salt, Resmetirom:L-proline, and crystalline forms thereof, with at least one pharmaceutically acceptable excipient.

The crystalline polymorphs of Resmetirom and/or salts thereof and/or of Resmetirom:nicotinamide, Resmetirom: caffeine, Resmetirom: 2-picolinic acid and/or Resmetirom: Urea, or Resmetirom N-methyl-morpholine salt, Resmetirom piperazine salt, Resmetirom benzathine salt, Resmetirom:L-proline, and crystalline forms thereof, as defined herein and the pharmaceutical compositions or formulations of the crystalline polymorphs of Resmetirom and of Resmetirom:nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom:L-proline, and crystalline forms thereof, may be used as medicaments, such as for the treatment of non-alcoholic steatohepatitis (NASH), non-alcoholic fatty liver disease (NAFLD) and/or associated dyslipidemias.

The present disclosure also provides methods of treating non-alcoholic steatohepatitis (NASH), non-alcoholic fatty liver disease (NAFLD) and/or associated dyslipidemias, by administering a therapeutically effective amount of any one or a combination of the crystalline polymorphs of Resmetirom and/or salts thereof and of Resmetirom:nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom:L-proline, and crystalline forms thereof, of the present disclosure, or at least one of the above pharmaceutical compositions, to a subject suffering from non-alcoholic steatohepatitis (NASH), non-alcoholic fatty liver disease (NAFLD) and/or associated dyslipidemias, or otherwise in need of the treatment.

The present disclosure also provides uses of any one or a combination of the crystalline polymorphs of Resmetirom and/or salts thereof and/or of Resmetirom:nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom: L-proline, and crystalline forms thereof, of the present disclosure, or at least one of the above pharmaceutical compositions, for the manufacture of medicaments for treating e.g., non-alcoholic steatohepatitis (NASH), non-alcoholic fatty liver disease (NAFLD) and/or associated dyslipidemias.

BRIEF DESCRIPTION OF THE DRAWINGS

FIG. 3 shows a characteristic X-ray powder diffraction pattern (XRPD) of Resmetirom Form 4.

DETAILED DESCRIPTION OF THE DISCLOSURE

Figure 1:
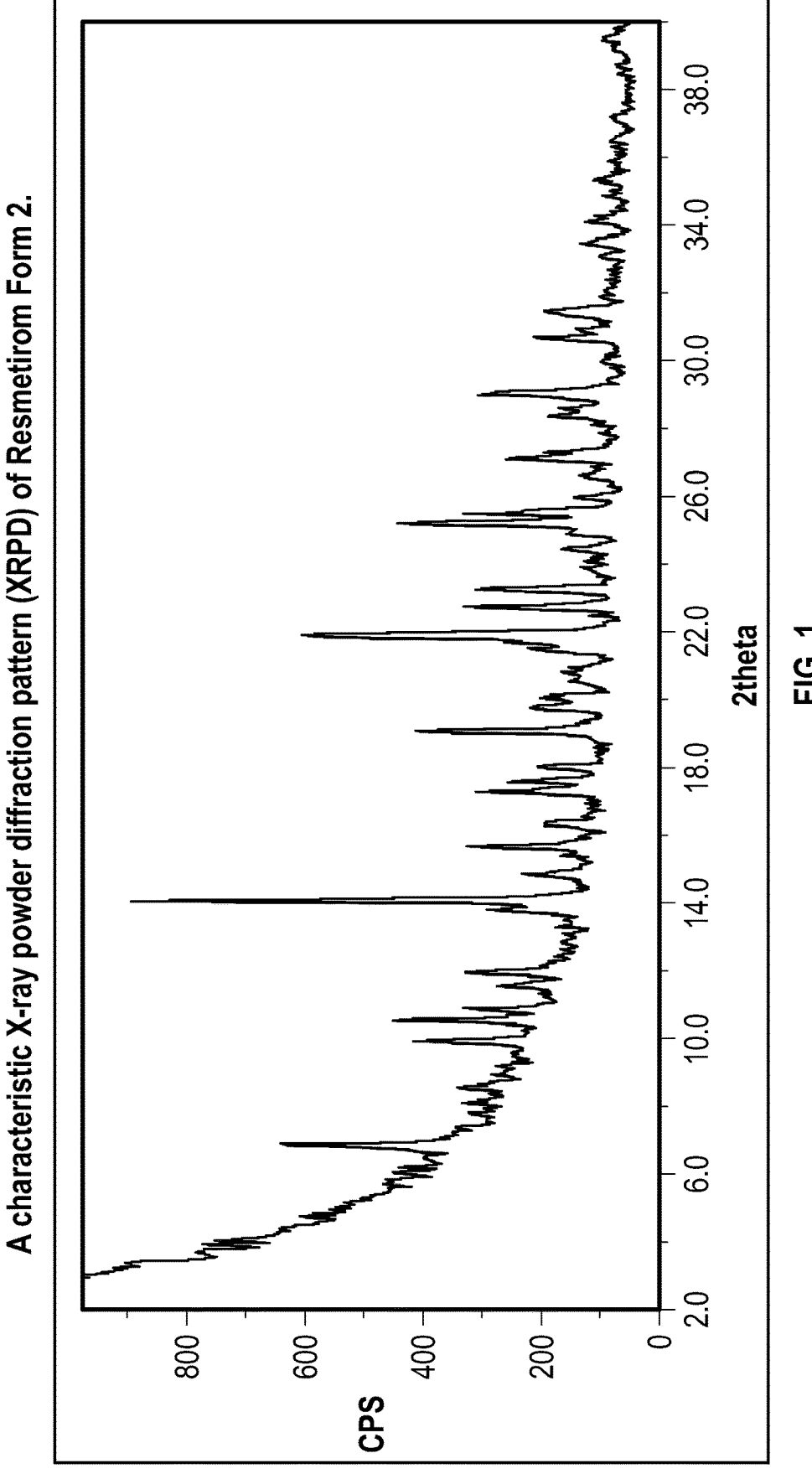
FIG. 1 shows a characteristic X-ray powder diffraction pattern (XRPD) of Resmetirom Form 2.

The present disclosure provides crystalline polymorphs of Resmetirom and salts thereof. The present disclosure further provides crystalline Resmetirom:nicotinamide, Resmetirom:caffeine, Resmetirom: 2-picolinic acid and/or Resmetirom:Urea and solid state forms thereof. The present disclosure also provides Resmetirom N-methyl-morpholine salt, Resmetirom piperazine salt, Resmetirom benzathine salt, Resmetirom:L-proline, and crystalline forms thereof, The present disclosure also provides processes for preparation thereof, and pharmaceutical compositions thereof. The crystalline forms of Resmetirom as well as Resmetirom: nicotinamide, Resmetirom:caffeine, Resmetirom: 2-picolinic acid and/or Resmetirom:Urea and the solid state forms thereof, or Resmetirom N-methyl-morpholine salt, Resmetirom piperazine salt, Resmetirom benzathine salt, Resmetirom:L-proline, and crystalline forms thereof, can be used to prepare other solid state forms of Resmetirom, Resmetirom salts or co-crystals and their solid state forms.

Solid state properties of Resmetirom, salts thereof as well as Resmetirom:nicotinamide, Resmetirom:caffeine, Resmetirom: 2-picolinic acid and/or and Resmetirom:Urea and crystalline polymorphs thereof, or of Resmetirom N-methyl-morpholine salt, Resmetirom piperazine salt, Resmetirom benzathine salt, Resmetirom:L-proline, and crystalline forms thereof, can be influenced by controlling the conditions under which they are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Resmetirom described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Resmetirom. In some embodiments of the disclosure, the described crystalline polymorph of Resmetirom may contain from about 1% to about 20% (w/w), from about 5% to about 20% (w/w), or from about 5% to about 10% (w/w) of one or more other crystalline polymorph of the same Resmetirom.

Depending on which other crystalline polymorphs a comparison is made, the crystalline polymorphs of Resmetirom of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Resmetirom referred to herein as being characterized by graphical data "as depicted in" or "as substantially depicted in" a Figure will thus be understood to include any crystal forms of Resmetirom characterized with the graphical data having such small variations, as are well known to the skilled person, in comparison with the Figure.

As used herein, and unless stated otherwise, the term "anhydrous" in relation to crystalline forms of Resmetirom, relates to a crystalline form of Resmetirom which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

"Co-Crystal" or "Co-crystal" as used herein is defined as a crystalline material including two or more molecules in the same crystalline lattice and associated by non-ionic and non-covalent bonds. In some embodiments, the co-crystal includes two molecules which are in natural state.

As used herein, the term "isolated" in reference to crystalline polymorph of Resmetirom of the present disclosure corresponds to a crystalline polymorph of Resmetirom that is physically separated from the reaction mixture in which it is formed.

As used herein, unless stated otherwise, the XRPD measurements are taken using copper Kα radiation wavelength 1.5418 Å. XRPD peaks reported herein are measured using CuK α radiation, λ=1.5418 Å, typically at a temperature of 25±3° C. For FIG. 27, copper radiation of 1.54060 Å was used, typically at a temperature of 25±3° C.

As used herein, $^{13}C$ NMR spectra are preferably measured at 11.7 T at magic angle spinning (MAS) frequency ωr/2π=64 kHz.

As used herein, unless stated otherwise, TGA analysis is carried out at a heating rate of 10° C./min to 250° C., preferably with a nitrogen flow of 40 ml/minute.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

As used herein, crystalline Resmetirom:nicotinamide is a distinct molecular species. Crystalline Resmetirom:nicotinamide may be a co-crystal of Resmetirom and nicotinamide. Alternatively, crystalline Resmetirom:nicotinamide may be a salt.

As used herein, crystalline Resmetirom:caffeine is a distinct molecular species. Crystalline Resmetirom:caffeine may be a co-crystal of Resmetirom and caffeine. Alternatively, crystalline Resmetirom:caffeine may be a salt.

As used herein, crystalline Resmetirom: 2-picolinic acid is a distinct molecular species. Crystalline Resmetirom: 2-picolinic acid may be a co-crystal of Resmetirom and 2-picolinic acid. Alternatively, crystalline Resmetirom: 2-picolinic acid may be a salt.

As used herein, crystalline Resmetirom:Urea acid is a distinct molecular species. Crystalline Resmetirom:Urea may be a co-crystal of Resmetirom and Urea. Alternatively, crystalline Resmetirom:Urea may be a salt.

The present disclosure includes a crystalline polymorph Resmetirom, designated Form 2. The crystalline Form 2 of Resmetirom may be characterized by data selected from one or more of the following: an X-ray powder diffraction pattern substantially as depicted in FIG. 1; an X-ray powder diffraction pattern having peaks at 6.9, 10.0, 14.1, 19.1 and 21.9 degrees 2-theta±0.2 degrees 2-theta; and combinations of these data.

Crystalline Form 2 of Resmetirom may be further characterized by an X-ray powder diffraction pattern having peaks at 6.9, 10.0, 14.1, 19.1 and 21.9 degrees 2-theta±0.2 degrees 2-theta, and also having any one, two, three, four or five additional peaks selected from 12.0, 15.7, 22.7, 23.3 and 25.2 degrees 2-theta±0.2 degrees 2-theta.

Crystalline form 2 may be alternatively characterized by an X-ray powder diffraction pattern having peaks at 6.9, 10.0, 12.0, 14.1, 15.7, 19.1, 21.9, 22.7, 23.3 and 25.2 degrees 2-theta±0.2 degrees 2-theta.

In one embodiment of the present disclosure, crystalline Form 2 of Resmetirom is isolated.

Crystalline Form 2 of Resmetirom may be a Methyl isopropyl ketone solvate.

Crystalline Form 2 of Resmetirom may be characterized by each of the above characteristics alone/or by all possible combinations, e.g., an XRPD pattern having peaks at 6.9, 10.0, 14.1, 19.1 and 21.9 degrees 2-theta±0.2 degrees 2-theta; an XRPD pattern as depicted in FIG. 1, and combinations thereof.

Figure 2:
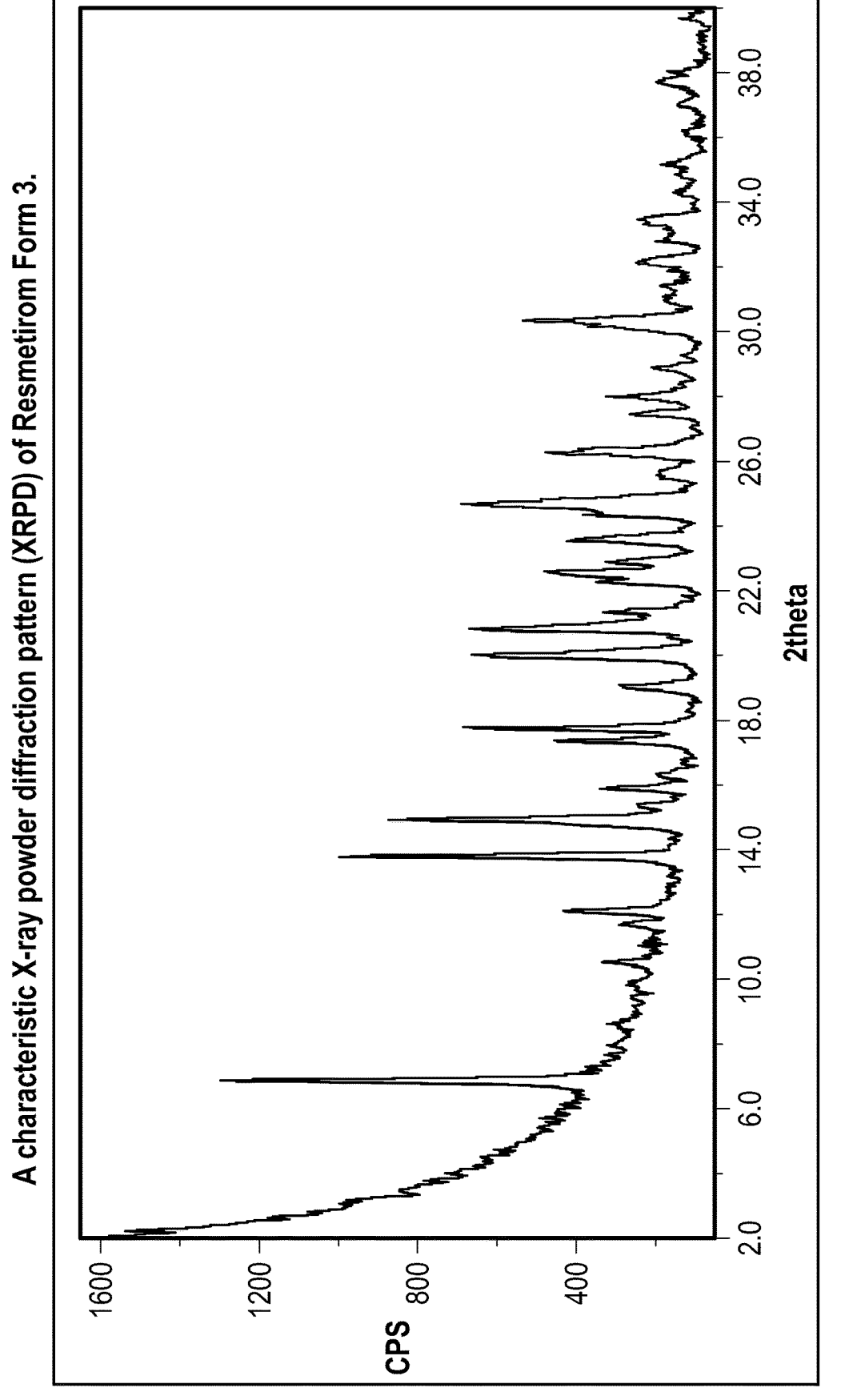
FIG. 2 shows a characteristic X-ray powder diffraction pattern (XRPD) of Resmetirom Form 3.

The present disclosure includes a crystalline polymorph Resmetirom, designated Form 3. The crystalline Form 3 of Resmetirom may be characterized by data selected from one or more of the following: an X-ray powder diffraction pattern substantially as depicted in FIG. 2; an X-ray powder diffraction pattern having peaks at 6.9, 13.8, 15.0, 20.0 and 20.8 degrees 2-theta±0.2 degrees 2-theta; and combinations of these data.

Crystalline Form 3 of Resmetirom may be further characterized by an X-ray powder diffraction pattern having peaks at 6.9, 13.8, 15.0, 20.0 and 20.8 degrees 2-theta±0.2 degrees 2-theta, and also having any one, two, three, four or five additional peaks selected from 12.1, 17.4, 17.8, 19.0 and 23.6 degrees 2-theta±0.2 degrees 2-theta.

Crystalline form 3 may be alternatively characterized by an X-ray powder diffraction pattern having peaks at 6.9, 12.1, 13.8, 15.0, 17.4, 17.8, 19.0, 20.0, 20.8 and 23.6 degrees 2-theta±0.2 degrees 2-theta.

In one embodiment of the present disclosure, crystalline Form 3 of Resmetirom is isolated.

Crystalline Form 3 of Resmetirom may be a dioxane solvate.

Crystalline Form 3 of Resmetirom may be characterized by each of the above characteristics alone/or by all possible combinations, e.g., an XRPD pattern having peaks at 6.9, 13.8, 15.0, 20.0 and 20.8 degrees 2-theta±0.2 degrees 2-theta; an XRPD pattern as depicted in FIG. 2, and combinations thereof.

Figure 3:
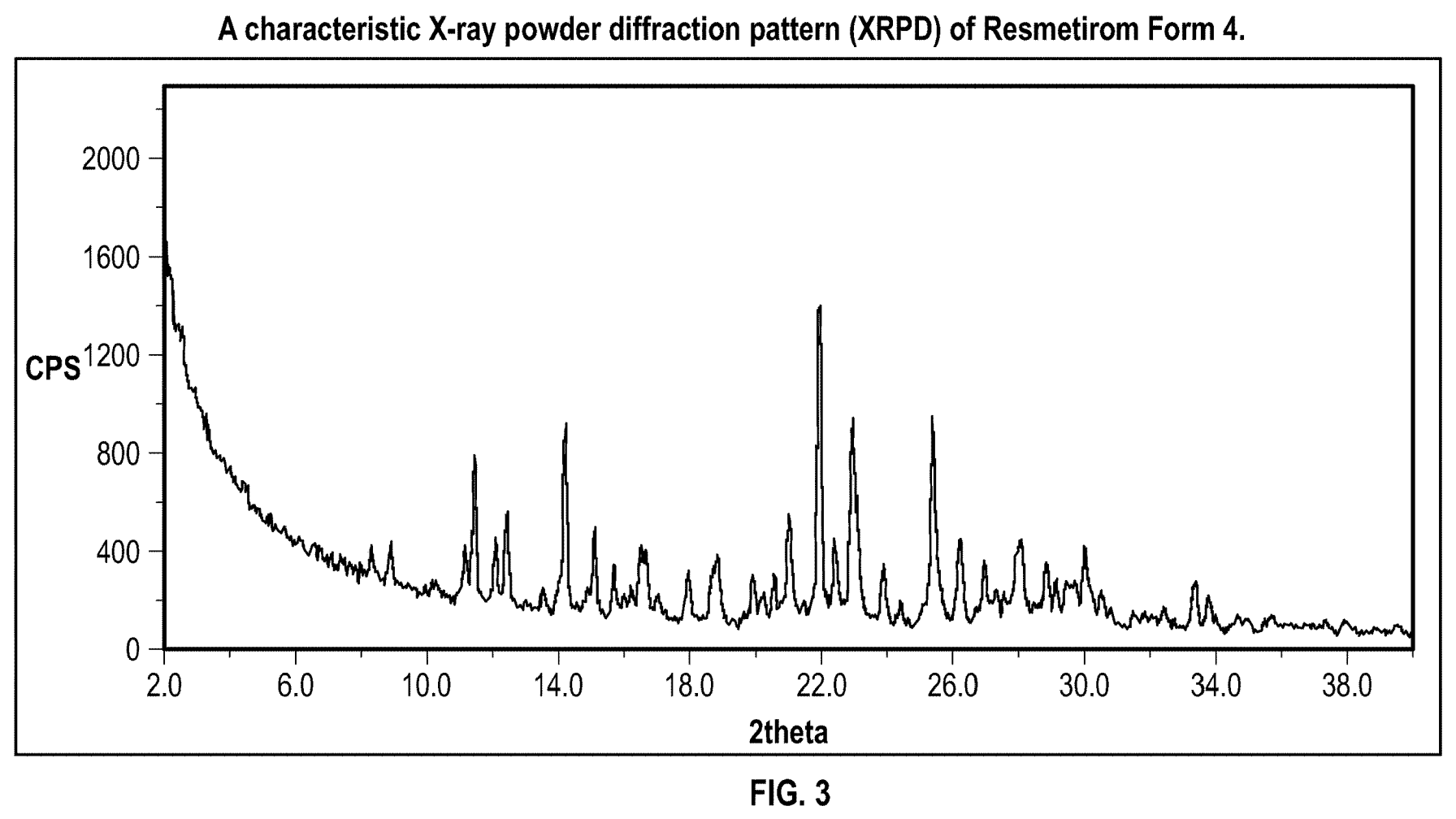

The present disclosure includes a crystalline polymorph Resmetirom, designated Form 4. The crystalline Form 4 of Resmetirom may be characterized by data selected from one or more of the following: an X-ray powder diffraction pattern substantially as depicted in FIG. 3; an X-ray powder diffraction pattern having peaks at 11.5, 14.2, 18.0, 22.0 and 25.4 degrees 2-theta±0.2 degrees 2-theta; and combinations of these data.

Crystalline Form 4 of Resmetirom may be further characterized by an X-ray powder diffraction pattern having peaks at 11.5, 14.2, 18.0, 22.0 and 25.4 degrees 2-theta±0.2 degrees 2-theta, and also having any one, two, three, four or five additional peaks selected from 12.1, 12.5, 15.2, 21.0 and 23.0 degrees 2-theta±0.2 degrees 2-theta.

Crystalline form 4 may be alternatively characterized by an X-ray powder diffraction pattern having peaks at 11.5, 12.1, 12.5, 14.2, 15.2, 18.0, 21.0, 22.0, 23.0 and 25.4 and degrees 2-theta±0.2 degrees 2-theta.

In one embodiment of the present disclosure, crystalline Form 4 of Resmetirom is isolated.

Crystalline Form 4 of Resmetirom may be an Anisole solvate.

Crystalline Form 4 of Resmetirom may be characterized by each of the above characteristics alone/or by all possible combinations, e.g., an XRPD pattern having peaks at 11.5, 14.2, 18.0, 22.0 and 25.4 degrees 2-theta±0.2 degrees 2-theta; an XRPD pattern as depicted in FIG. 3, and combinations thereof.

Figure 4:
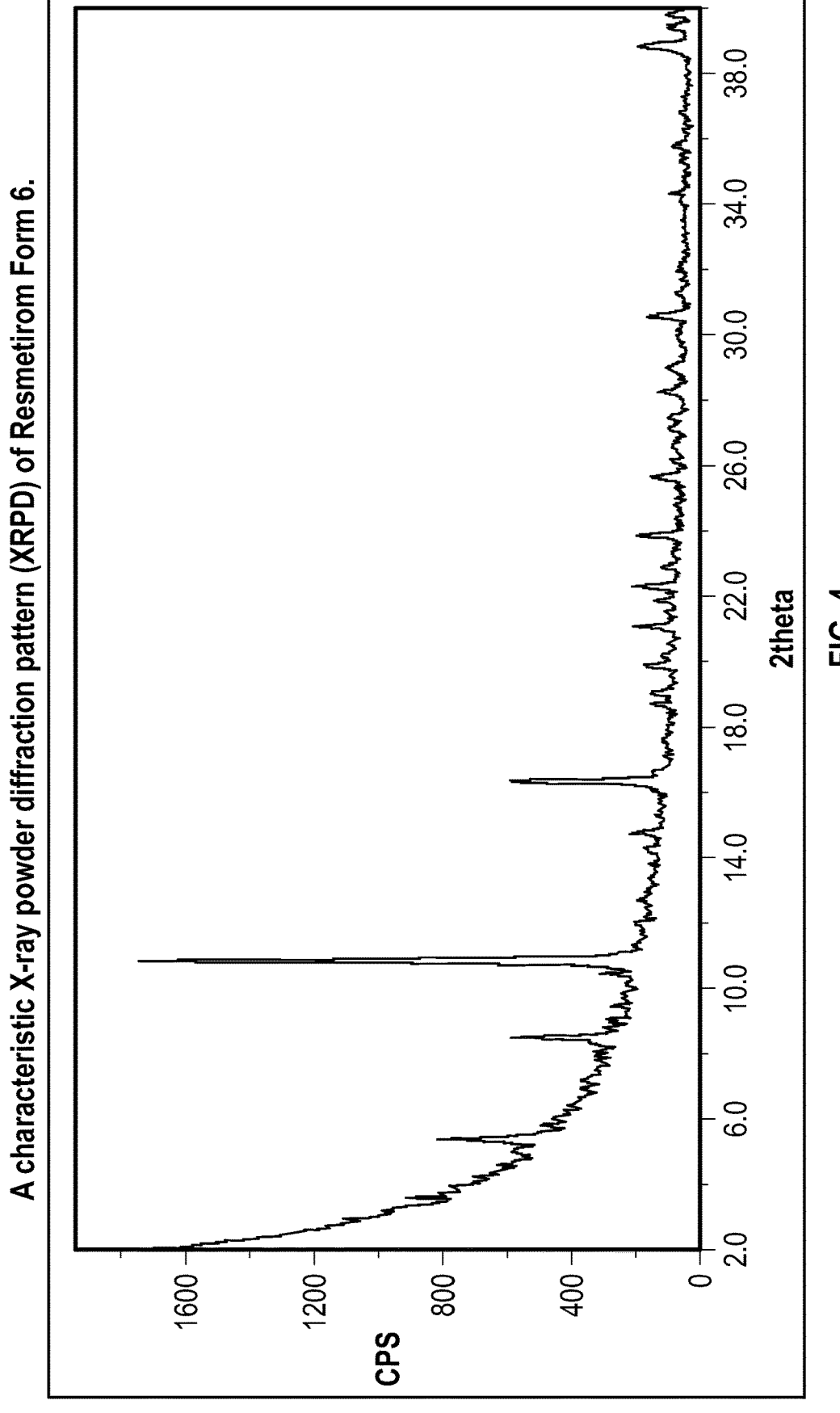
FIG. 4 shows a characteristic X-ray powder diffraction pattern (XRPD) of Resmetirom Form 6.

The present disclosure includes a crystalline polymorph Resmetirom, designated Form 6. The crystalline Form 6 of Resmetirom may be characterized by data selected from one or more of the following: an X-ray powder diffraction pattern substantially as depicted in FIG. 4; an X-ray powder diffraction pattern having peaks at 5.4, 8.5, 10.9, 16.4 and 23.9 degrees 2-theta±0.2 degrees 2-theta; and combinations of these data.

Crystalline Form 6 of Resmetirom may be further characterized by an X-ray powder diffraction pattern having peaks at 5.4, 8.5, 10.9, 16.4 and 23.9 degrees 2-theta±0.2 degrees 2-theta, and also having any one, two, three, four or five additional peaks selected from 19.1, 19.9, 21.1, 22.3 and 25.7 degrees 2-theta±0.2 degrees 2-theta.

Crystalline form 6 may be alternatively characterized by an X-ray powder diffraction pattern having peaks at 5.4, 8.5, 10.9, 16.4, 19.1, 19.9, 21.1, 22.3, 23.9 and 25.7 and degrees 2-theta±0.2 degrees 2-theta.

In one embodiment of the present disclosure, crystalline Form 6 of Resmetirom is isolated.

Crystalline Form 6 of Resmetirom may be a DMF solvate.

Crystalline Form 6 of Resmetirom may be characterized by each of the above characteristics alone/or by all possible combinations, e.g., an XRPD pattern having peaks at 5.4, 8.5, 10.9, 16.4 and 23.9 degrees 2-theta±0.2 degrees 2-theta; an XRPD pattern as depicted in FIG. 4, and combinations thereof.

Figure 5:
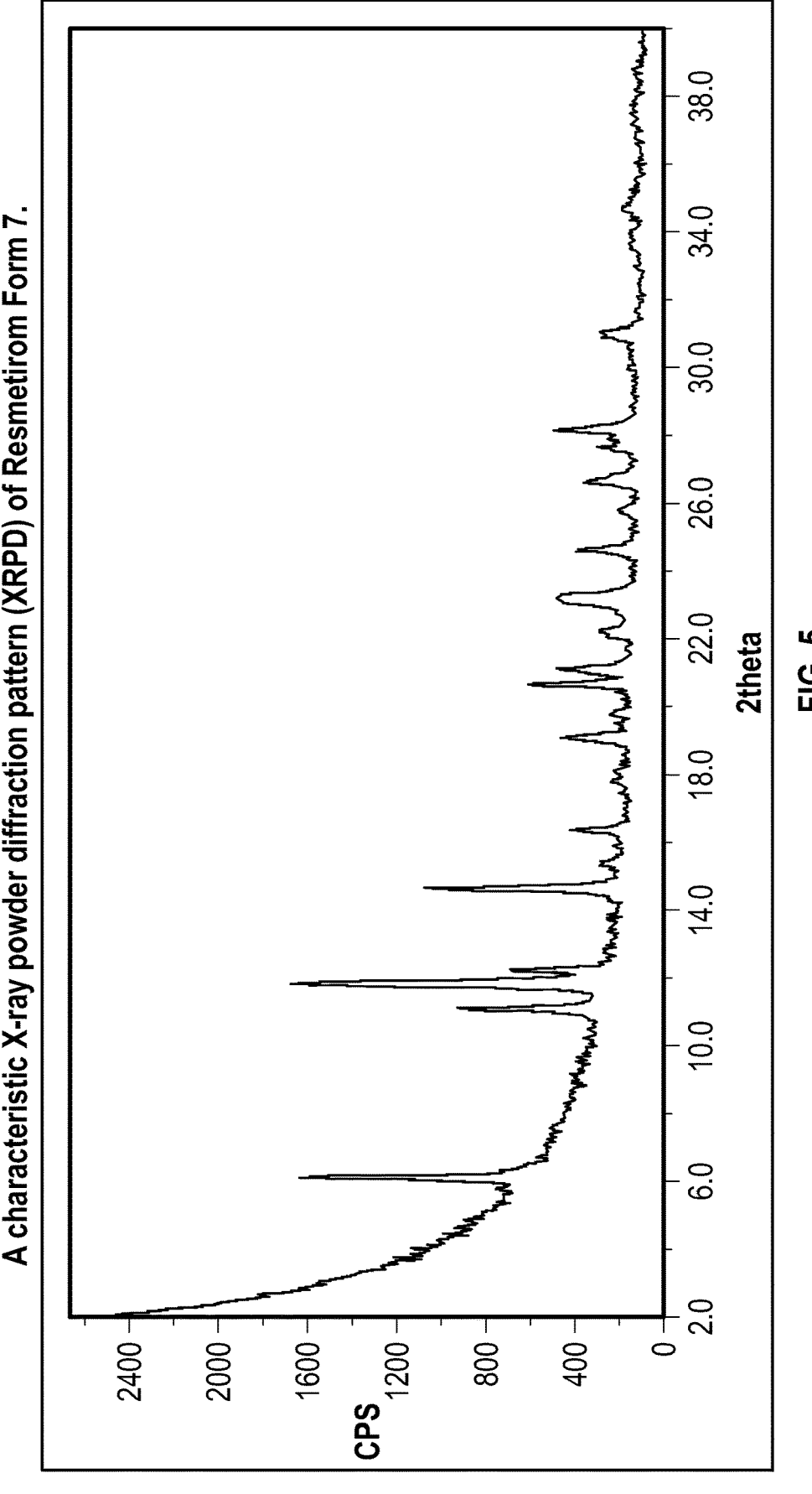
FIG. 5 shows a characteristic X-ray powder diffraction pattern (XRPD) of Resmetirom Form 7.

The present disclosure includes a crystalline polymorph Resmetirom, designated Form 7. The crystalline Form 7 of Resmetirom may be characterized by data selected from one or more of the following: an X-ray powder diffraction pattern substantially as depicted in FIG. 5; an X-ray powder diffraction pattern having peaks at 6.1, 11.8, 14.6, 19.1 and 26.6 degrees 2-theta±0.2 degrees 2-theta; and combinations of these data.

Crystalline Form 7 of Resmetirom may be further characterized by an X-ray powder diffraction pattern having peaks at 6.1, 11.8, 14.6, 19.1 and 26.6 degrees 2-theta±0.2 degrees 2-theta, and also having any one, two, three, four or five additional peaks selected from 11.0, 20.6, 21.2, 23.2 and 25.7 degrees 2-theta±0.2 degrees 2-theta.

Crystalline form 7 may be alternatively characterized by an X-ray powder diffraction pattern having peaks at 6.1, 11.0, 11.8, 14.6, 19.1, 20.6, 21.2, 23.2, 25.7 and 26.6 degrees 2-theta±0.2 degrees 2-theta.

In one embodiment of the present disclosure, crystalline Form 7 of Resmetirom is isolated.

Crystalline Form 7 of Resmetirom may be an Acetyl acetone solvate.

Crystalline Form 7 of Resmetirom may be characterized by each of the above characteristics alone/or by all possible combinations, e.g., an XRPD pattern having peaks at 6.1, 11.8, 14.6, 19.1 and 26.6 degrees 2-theta±0.2 degrees 2-theta; an XRPD pattern as depicted in FIG. 5, and combinations thereof.

Figure 6:
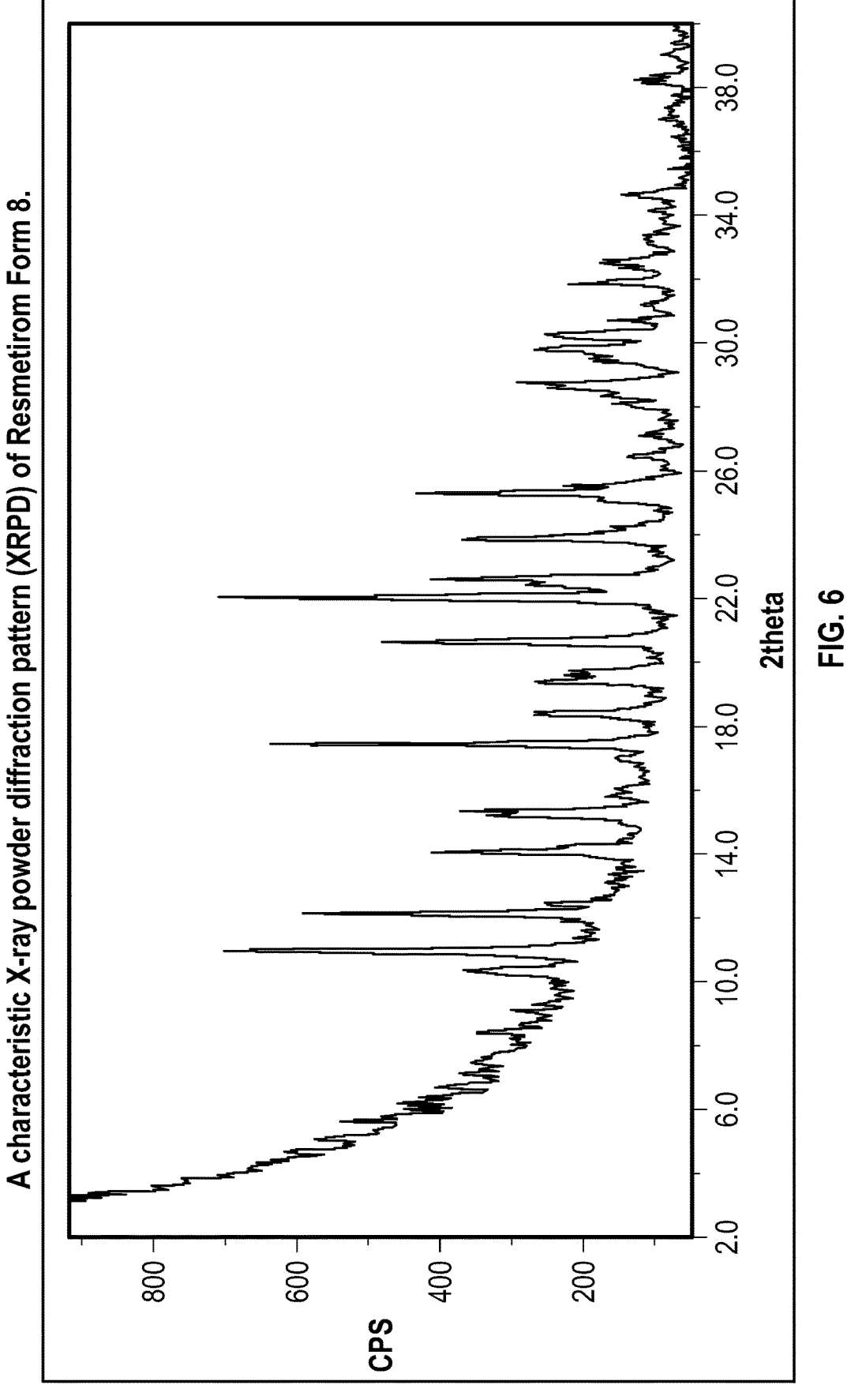
FIG. 6 shows a characteristic X-ray powder diffraction pattern (XRPD) of Resmetirom Form 8.

The present disclosure includes a crystalline polymorph Resmetirom, designated Form 8. The crystalline Form 8 of Resmetirom may be characterized by data selected from one or more of the following: an X-ray powder diffraction pattern substantially as depicted in FIG. 6; an X-ray powder diffraction pattern having peaks at 11.0, 12.2, 17.5, 20.7 and 22.0 degrees 2-theta±0.2 degrees 2-theta; and combinations of these data.

Crystalline Form 8 of Resmetirom may be further characterized by an X-ray powder diffraction pattern having peaks at 11.0, 12.2, 17.5, 20.7 and 22.0 degrees 2-theta±0.2 degrees 2-theta, and also having any one, two, three, four or five additional peaks selected from 10.3, 14.1, 15.4, 23.9 and 25.4 degrees 2-theta±0.2 degrees 2-theta.

Crystalline form 8 may be alternatively characterized by an X-ray powder diffraction pattern having peaks at 10.3, 11.0, 12.2, 14.1, 15.4, 17.5, 20.7, 22.0, 23.9 and 25.4 degrees 2-theta±0.2 degrees 2-theta.

In one embodiment of the present disclosure, crystalline Form 8 of Resmetirom is isolated.

Crystalline Form 8 of Resmetirom may be a propionitrile solvate.

Crystalline Form 8 of Resmetirom may be characterized by each of the above characteristics alone/or by all possible combinations, e.g., an XRPD pattern having peaks at 11.0, 12.2, 17.5, 20.7 and 22.0 degrees 2-theta±0.2 degrees 2-theta; an XRPD pattern as depicted in FIG. 6, and combinations thereof.

Figure 7:
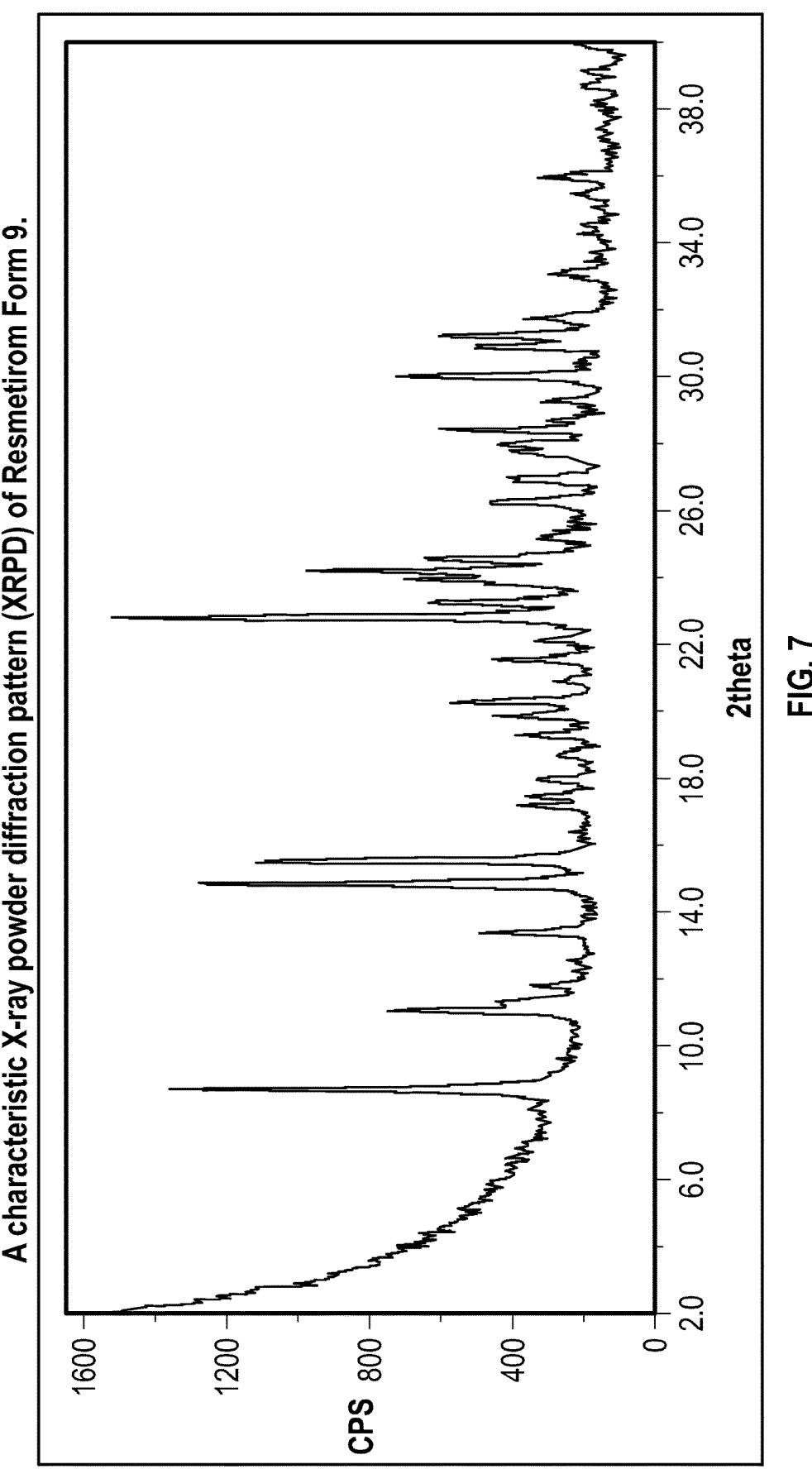
FIG. 7 shows a characteristic X-ray powder diffraction pattern (XRPD) of Resmetirom Form 9.

The present disclosure includes a crystalline polymorph Resmetirom, designated Form 9. The crystalline Form 9 of Resmetirom may be characterized by data selected from one or more of the following: an X-ray powder diffraction pattern substantially as depicted in FIG. 7; an X-ray powder diffraction pattern having peaks at 8.7, 13.4, 14.8, 15.5 and 22.8 degrees 2-theta±0.2 degrees 2-theta; and combinations of these data.

Crystalline Form 9 of Resmetirom may be further characterized by an X-ray powder diffraction pattern having peaks at 8.7, 13.4, 14.8, 15.5 and 22.8 degrees 2-theta±0.2 degrees 2-theta, and also having any one, two, three, four or five additional peaks selected from 11.1, 19.8, 20.3, 21.5 and 24.4 degrees 2-theta±0.2 degrees 2-theta.

Crystalline form 8 may be alternatively characterized by an X-ray powder diffraction pattern having peaks at 8.7, 11.1, 13.4, 14.8, 15.5 19.8, 20.3, 21.5, 22.8 and 24.4 degrees 2-theta±0.2 degrees 2-theta.

In one embodiment of the present disclosure, crystalline Form 9 of Resmetirom is isolated.

Crystalline Form 9 of Resmetirom may be a Nitrobenzene solvate.

Crystalline Form 9 of Resmetirom may be characterized by each of the above characteristics alone/or by all possible combinations, e.g., an XRPD pattern having peaks at 8.7, 13.4, 14.8, 15.5 and 22.8 degrees 2-theta±0.2 degrees 2-theta; an XRPD pattern as depicted in FIG. 7, and combinations thereof.

Figure 8:
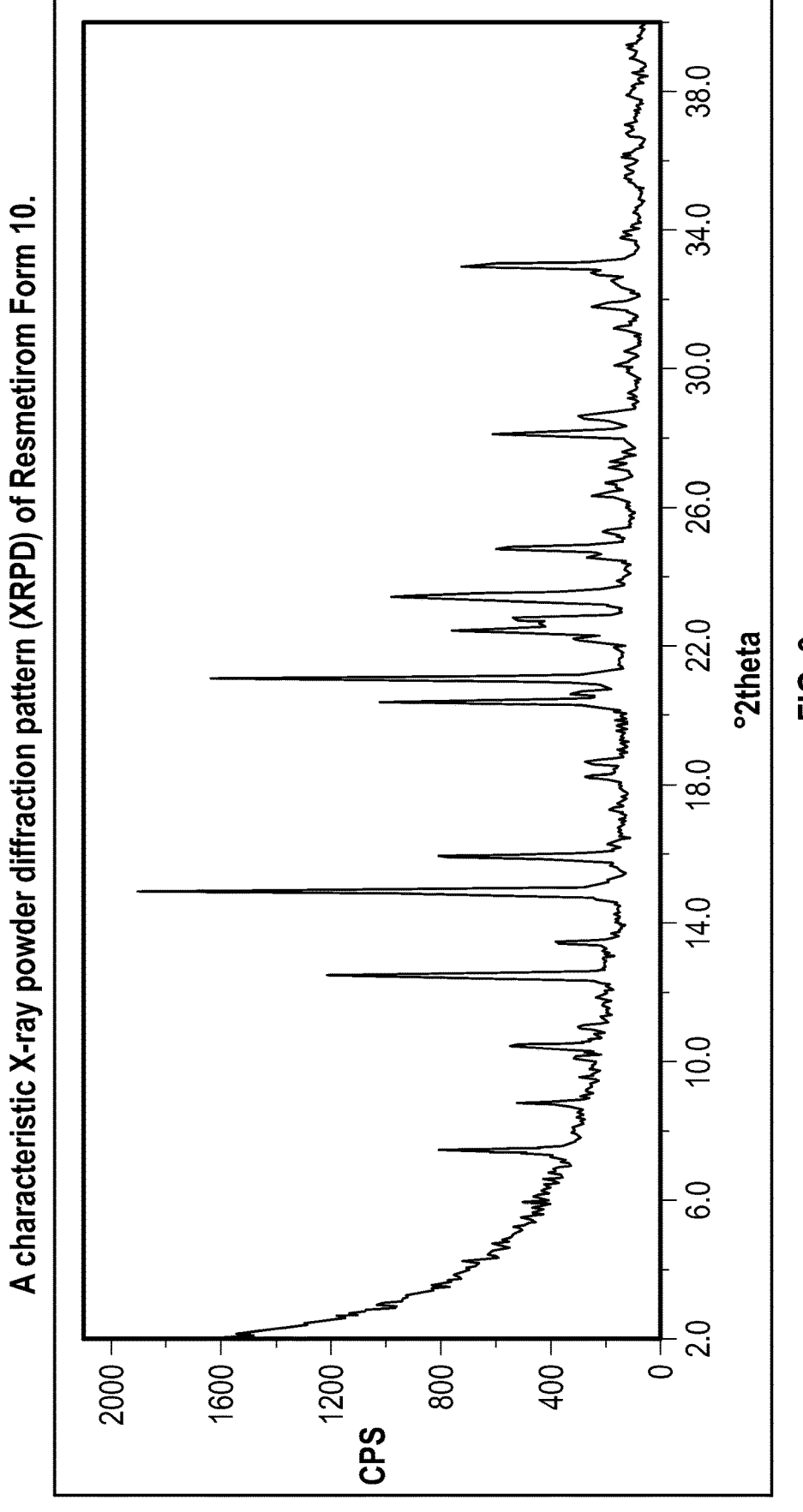
FIG. 8 shows a characteristic X-ray powder diffraction pattern (XRPD) of Resmetirom Form 10.

The present disclosure includes a crystalline polymorph Resmetirom, designated Form 10. The crystalline Form 10 of Resmetirom may be characterized by data selected from one or more of the following: an X-ray powder diffraction pattern substantially as depicted in FIG. 8; an X-ray powder diffraction pattern having peaks at 12.5, 14.9, 20.4, 21.1 and 23.4 degrees 2-theta±0.2 degrees 2-theta; and combinations of these data.

Crystalline Form 10 of Resmetirom may be further characterized by an X-ray powder diffraction pattern having peaks at 12.5, 14.9, 20.4, 21.1 and 23.4 degrees 2-theta±0.2 degrees 2-theta, and also having any one, two, three, four or five additional peaks selected from 7.4, 13.4, 16.0, 22.5 and 24.8 degrees 2-theta±0.2 degrees 2-theta.

Crystalline form 10 may be alternatively characterized by an X-ray powder diffraction pattern having peaks at 7.4, 12.5, 13.4, 14.9, 16.0, 20.4, 21.1, 22.5, 23.4 and 24.8 degrees 2-theta±0.2 degrees 2-theta.

In one embodiment of the present disclosure, crystalline Form 10 of Resmetirom is isolated.

Crystalline Form 10 of Resmetirom may be Di(ethylene glycol)ethyl ether solvate.

Crystalline Form 10 of Resmetirom may be characterized by each of the above characteristics alone/or by all possible combinations, e.g., an XRPD pattern having peaks at 12.5, 14.9, 20.4, 21.1 and 23.4 degrees 2-theta±0.2 degrees 2-theta; an XRPD pattern as depicted in FIG. 8, and combinations thereof.

Figure 9:
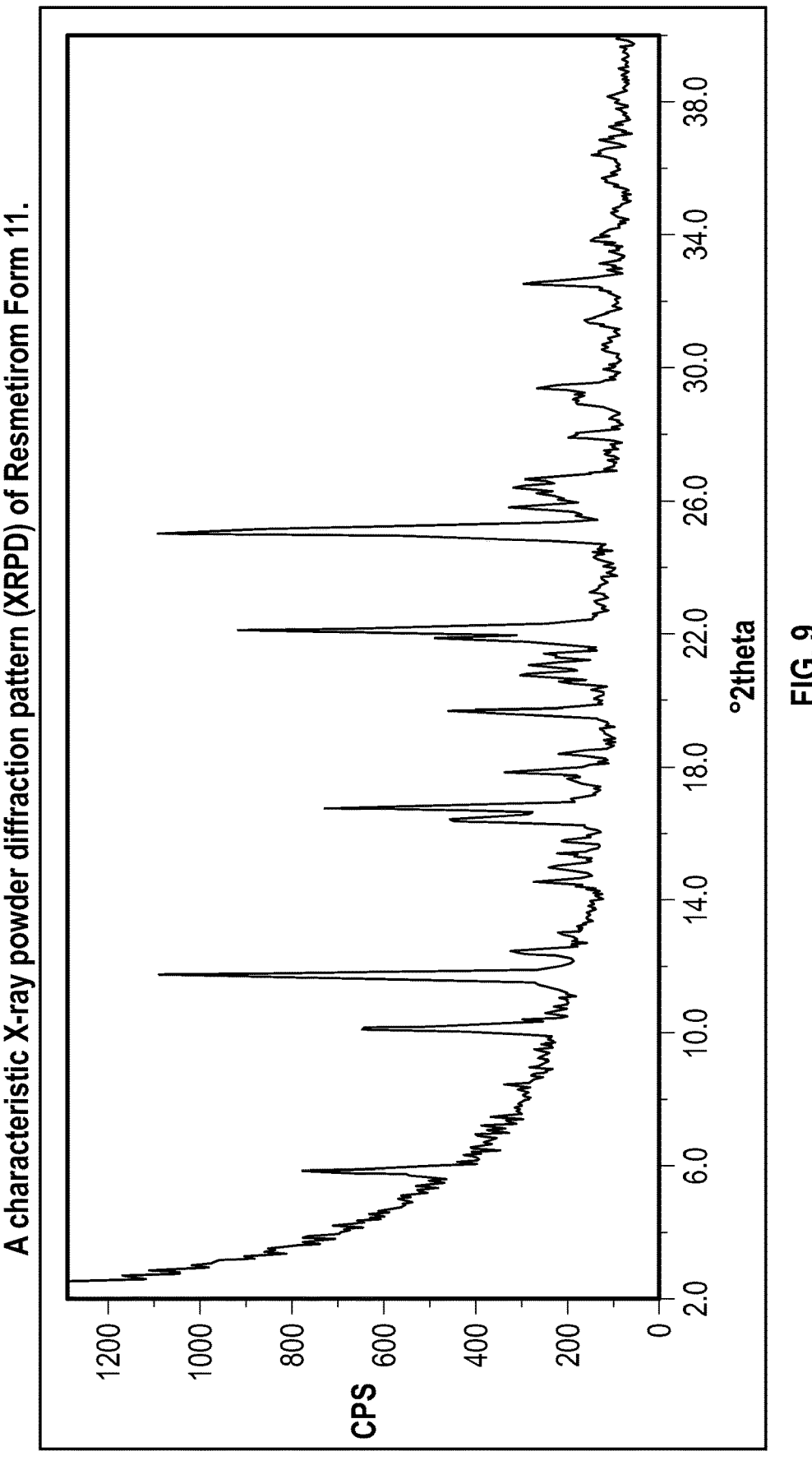
FIG. 9 shows a characteristic X-ray powder diffraction pattern (XRPD) of Resmetirom Form 11.

The present disclosure includes a crystalline polymorph Resmetirom, designated Form 11. The crystalline Form 11 of Resmetirom may be characterized by data selected from one or more of the following: an X-ray powder diffraction pattern substantially as depicted in FIG. 9; an X-ray powder diffraction pattern having peaks at 5.9, 10.1, 11.8, 19.7 and 25.1 degrees 2-theta±0.2 degrees 2-theta; and combinations of these data.

Crystalline Form 11 of Resmetirom may be further characterized by an X-ray powder diffraction pattern having peaks at 5.9, 10.1, 11.8, 19.7 and 25.1 degrees 2-theta±0.2 degrees 2-theta, and also having any one, two, three, four or five additional peaks selected from 12.5, 16.4, 16.8, 17.9 and 22.2 degrees 2-theta±0.2 degrees 2-theta.

Crystalline form 11 may be alternatively characterized by an X-ray powder diffraction pattern having peaks at 5.9, 10.1, 11.8, 12.5, 16.4, 16.8, 17.9, 19.7, 22.2 and 25.1 degrees 2-theta±0.2 degrees 2-theta.

In one embodiment of the present disclosure, crystalline Form 11 of Resmetirom is isolated.

Crystalline Form 11 of Resmetirom may be a 1,3-dioxolane solvate.

Crystalline Form 11 of Resmetirom may be characterized by each of the above characteristics alone/or by all possible combinations, e.g., an XRPD pattern having peaks at 5.9, 10.1, 11.8, 19.7 and 25.1 degrees 2-theta±0.2 degrees 2-theta; an XRPD pattern as depicted in FIG. 9, and combinations thereof.

Figure 10:
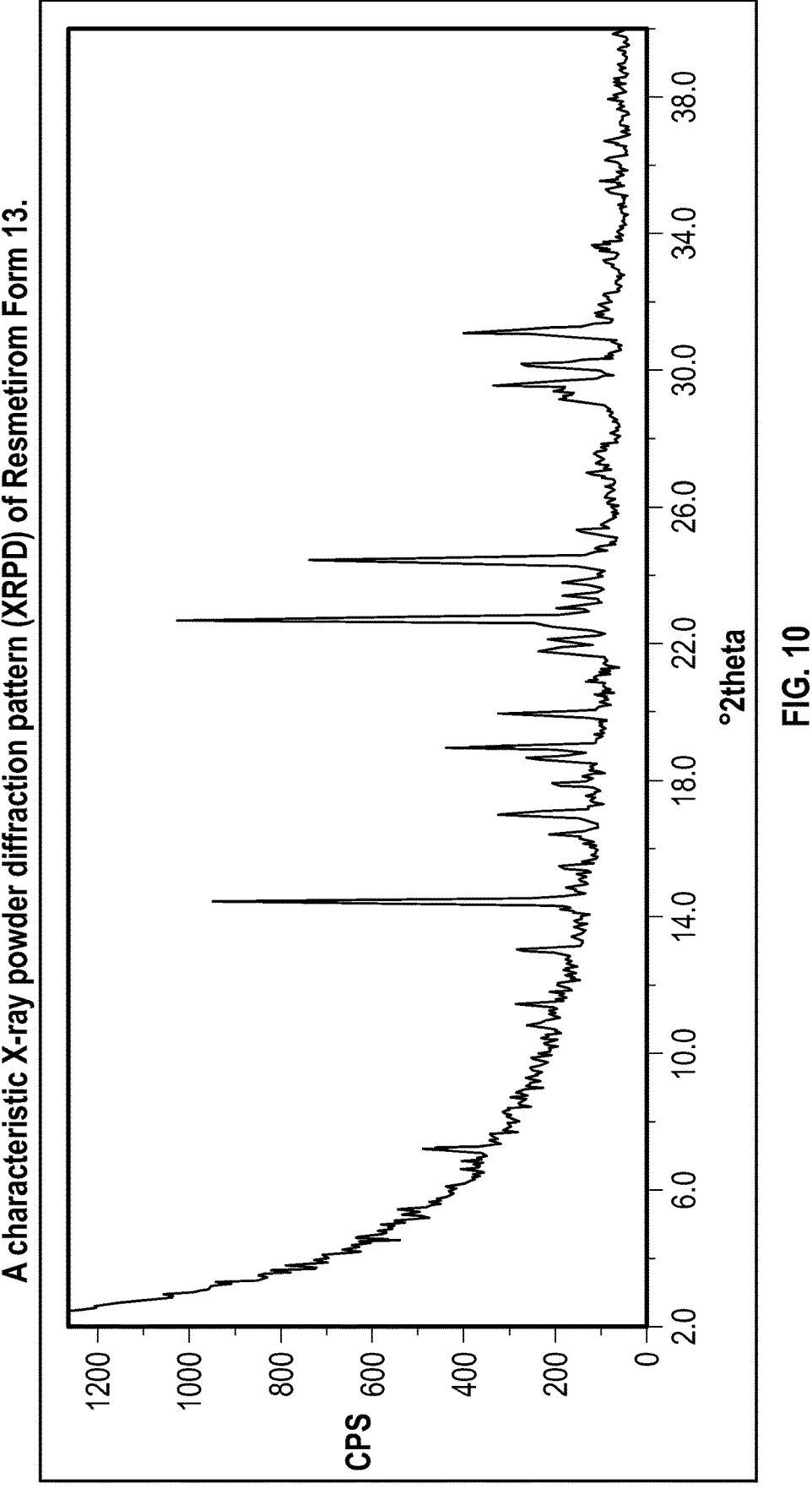
FIG. 10 shows a characteristic X-ray powder diffraction pattern (XRPD) of Resmetirom Form 13.

The present disclosure includes a crystalline polymorph Resmetirom, designated Form 13. The crystalline Form 13 of Resmetirom may be characterized by data selected from one or more of the following: an X-ray powder diffraction pattern substantially as depicted in FIG. 10; an X-ray powder diffraction pattern having peaks at 14.4, 17.0, 20.0, 22.7 and 24.5 degrees 2-theta±0.2 degrees 2-theta; and combinations of these data.

Crystalline Form 13 of Resmetirom may be further characterized by an X-ray powder diffraction pattern having peaks at 14.4, 17.0, 20.0, 22.7 and 24.5 degrees 2-theta±0.2 degrees 2-theta, and also having any one, two, three, four or five additional peaks selected from 7.3, 13.0, 17.9, 18.7 and 19.0 degrees 2-theta±0.2 degrees 2-theta.

Crystalline form 13 may be alternatively characterized by an X-ray powder diffraction pattern having peaks at 7.3, 13.0, 14.4, 17.0, 17.9, 18.7 and 19.0, 20.0, 22.7 and 24.5 degrees 2-theta±0.2 degrees 2-theta.

In one embodiment of the present disclosure, crystalline Form 13 of Resmetirom is isolated.

Crystalline Form 13 of Resmetirom may be a Dichloroethane solvate.

Crystalline Form 13 of Resmetirom may be characterized by each of the above characteristics alone/or by all possible combinations, e.g., an XRPD pattern having peaks at 14.4, 17.0, 20.0, 22.7 and 24.5 degrees 2-theta±0.2 degrees 2-theta; an XRPD pattern as depicted in FIG. 10, and combinations thereof.

The present disclosure includes a crystalline polymorph Resmetirom, designated Form 14. The crystalline Form 14 of Resmetirom may be characterized by data selected from one or more of the following: an X-ray powder diffraction pattern substantially as depicted in FIG. 11; an X-ray powder diffraction pattern having peaks at 9.8, 11.1 and 23.2 degrees 2-theta±0.2 degrees 2-theta; and combinations of these data.

In one embodiment of the present disclosure, crystalline Form 14 of Resmetirom is isolated. Particularly, crystalline form 14 of Resmetirom according to any aspect or embodiment of the disclosure may be isolated.

Crystalline Form 14 of Resmetirom may be a methyl THF solvate, preferably a mono methyl THF solvate. In embodiments, crystalline form 14 of Resmetirom may contain about 11% to about 16% of methyl THF by weight, as determined by TGA.

Figure 11:
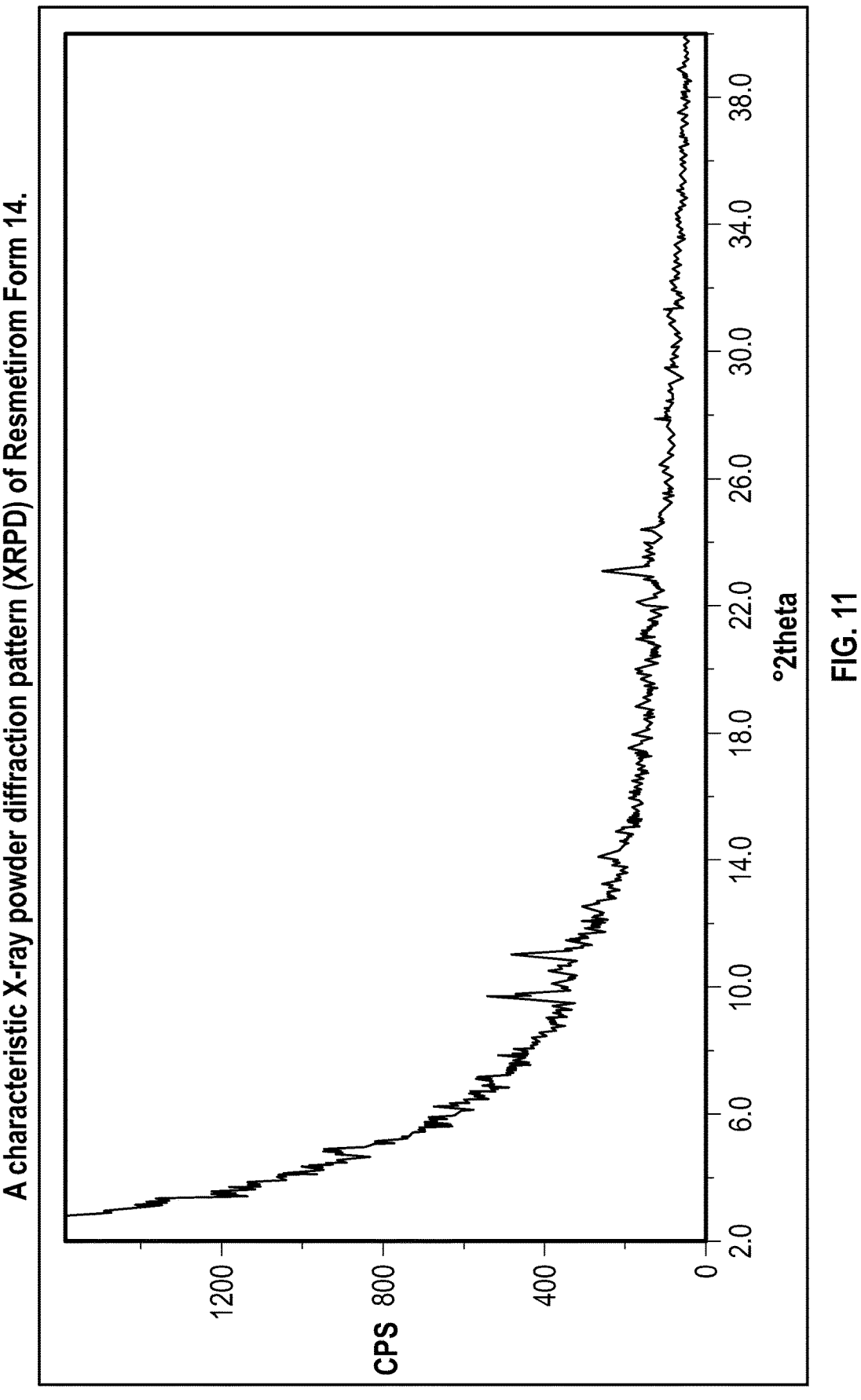
FIG. 11 shows a characteristic X-ray powder diffraction pattern (XRPD) of Resmetirom Form 14.

Crystalline Form 14 of Resmetirom may be characterized by each of the above characteristics alone/or by all possible combinations, e.g., an XRPD pattern having peaks at 9.8, 11.1 and 23.2 degrees 2-theta±0.2 degrees 2-theta; an XRPD pattern as depicted in FIG. 11, and combinations thereof.

Alternatively, crystalline form 14 may be characterized an X-ray powder diffraction pattern having peaks at 9.8, 11.1 and 23.2 degrees 2-theta±0.2 degrees 2-theta wherein form 14 is a methyl THF solvate.

Figure 12:
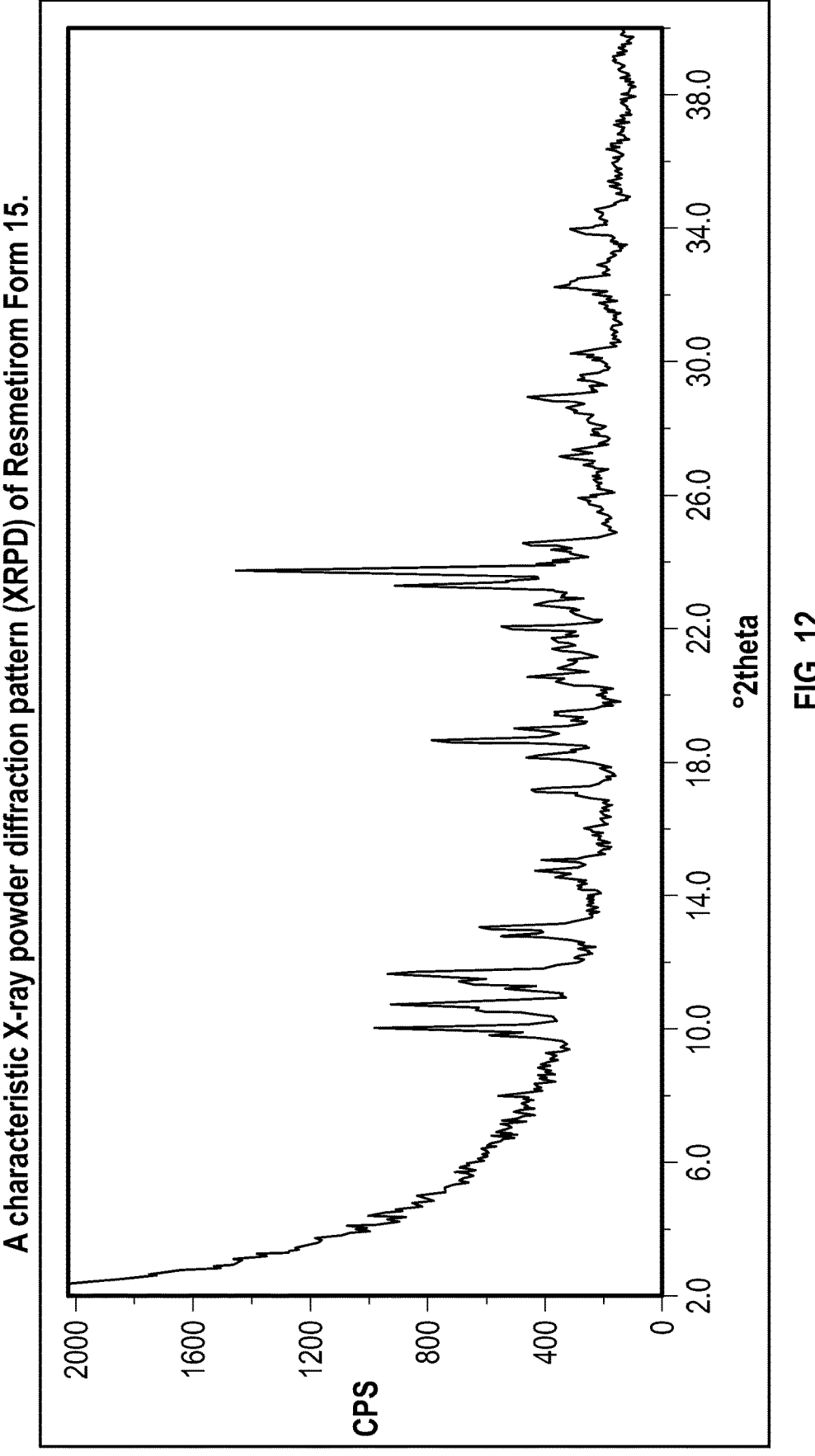
FIG. 12 shows a characteristic X-ray powder diffraction pattern (XRPD) of Resmetirom Form 15.

The present disclosure includes a crystalline polymorph Resmetirom, designated Form 15. The crystalline Form 15 of Resmetirom may be characterized by data selected from one or more of the following: an X-ray powder diffraction pattern substantially as depicted in FIG. 12; an X-ray powder diffraction pattern having peaks at 10.0, 11.6, 13.0, 18.6 and 23.8 degrees 2-theta±0.2 degrees 2-theta; and combinations of these data.

Crystalline Form 15 of Resmetirom may be further characterized by an X-ray powder diffraction pattern having peaks at 10.0, 11.6, 13.0, 18.6 and 23.8 degrees 2-theta±0.2 degrees 2-theta, and also having any one, two, three, four or five additional peaks selected from 10.7, 17.0, 18.2, 22.0 and 23.3 degrees 2-theta±0.2 degrees 2-theta.

Crystalline form 15 may be alternatively characterized by an X-ray powder diffraction pattern having peaks at 10.0, 10.7, 11.6, 13.0, 17.0, 18.2, 18.6, 22.0, 23.3 and 23.8 degrees 2-theta±0.2 degrees 2-theta.

In one embodiment of the present disclosure, crystalline Form 15 of Resmetirom is isolated.

Crystalline Form 15 of Resmetirom may be a Propionic acid solvate.

Crystalline Form 15 of Resmetirom may be characterized by each of the above characteristics alone/or by all possible combinations, e.g., an XRPD pattern having peaks at 10.0, 11.6, 13.0, 18.6 and 23.8 degrees 2-theta±0.2 degrees 2-theta; an XRPD pattern as depicted in FIG. 12, and combinations thereof.

Figure 13:
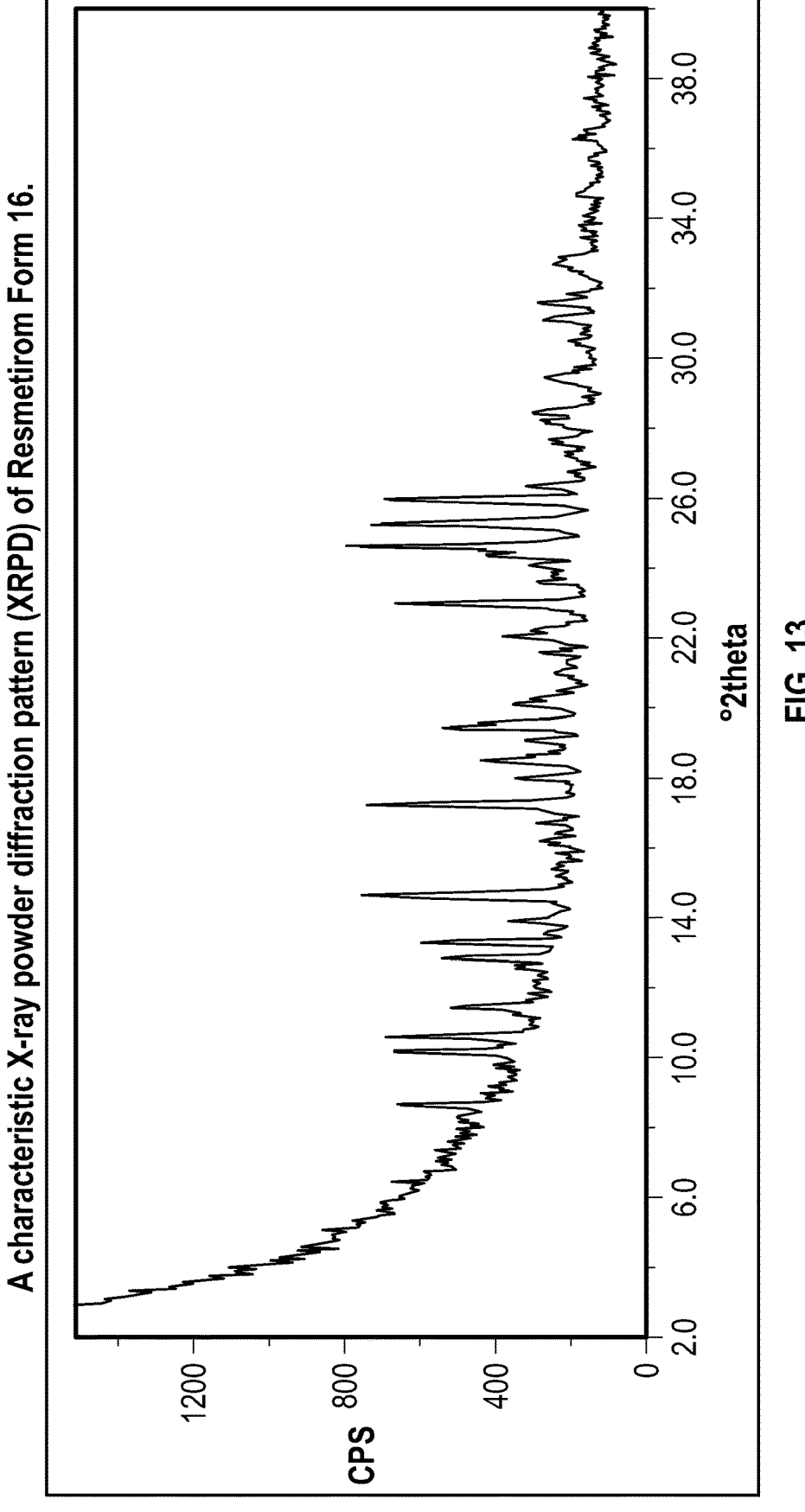
FIG. 13 shows a characteristic X-ray powder diffraction pattern (XRPD) of Resmetirom Form 16.

The present disclosure includes a crystalline polymorph Resmetirom, designated Form 16. The crystalline Form 16 of Resmetirom may be characterized by data selected from one or more of the following: an X-ray powder diffraction pattern substantially as depicted in FIG. 13; an X-ray powder diffraction pattern having peaks at 8.7, 11.5, 13.3, 14.7 and 26.0 degrees 2-theta±0.2 degrees 2-theta; and combinations of these data.

Crystalline Form 16 of Resmetirom may be further characterized by an X-ray powder diffraction pattern having peaks at 8.7, 11.5, 13.3, 14.7 and 26.0 degrees 2-theta±0.2 degrees 2-theta, and also having any one, two, three, four or five additional peaks selected from 10.2, 12.8, 19.5, 25.3 and 26.4 degrees 2-theta±0.2 degrees 2-theta.

Crystalline form 16 may be alternatively characterized by an X-ray powder diffraction pattern having peaks at 8.7, 10.2, 11.5, 12.8, 13.3, 14.7, 19.5, 25.3, 26.0 and 26.4 degrees 2-theta±0.2 degrees 2-theta.

In one embodiment of the present disclosure, crystalline Form 16 of Resmetirom is isolated.

Crystalline Form 16 of Resmetirom may be a Propionic acid solvate.

Crystalline Form 16 of Resmetirom may be characterized by each of the above characteristics alone/or by all possible combinations, e.g., an XRPD pattern having peaks at 8.7, 11.5, 13.3, 14.7 and 26.0 degrees 2-theta±0.2 degrees 2-theta; an XRPD pattern as depicted in FIG. 13, and combinations thereof.

Figure 14:
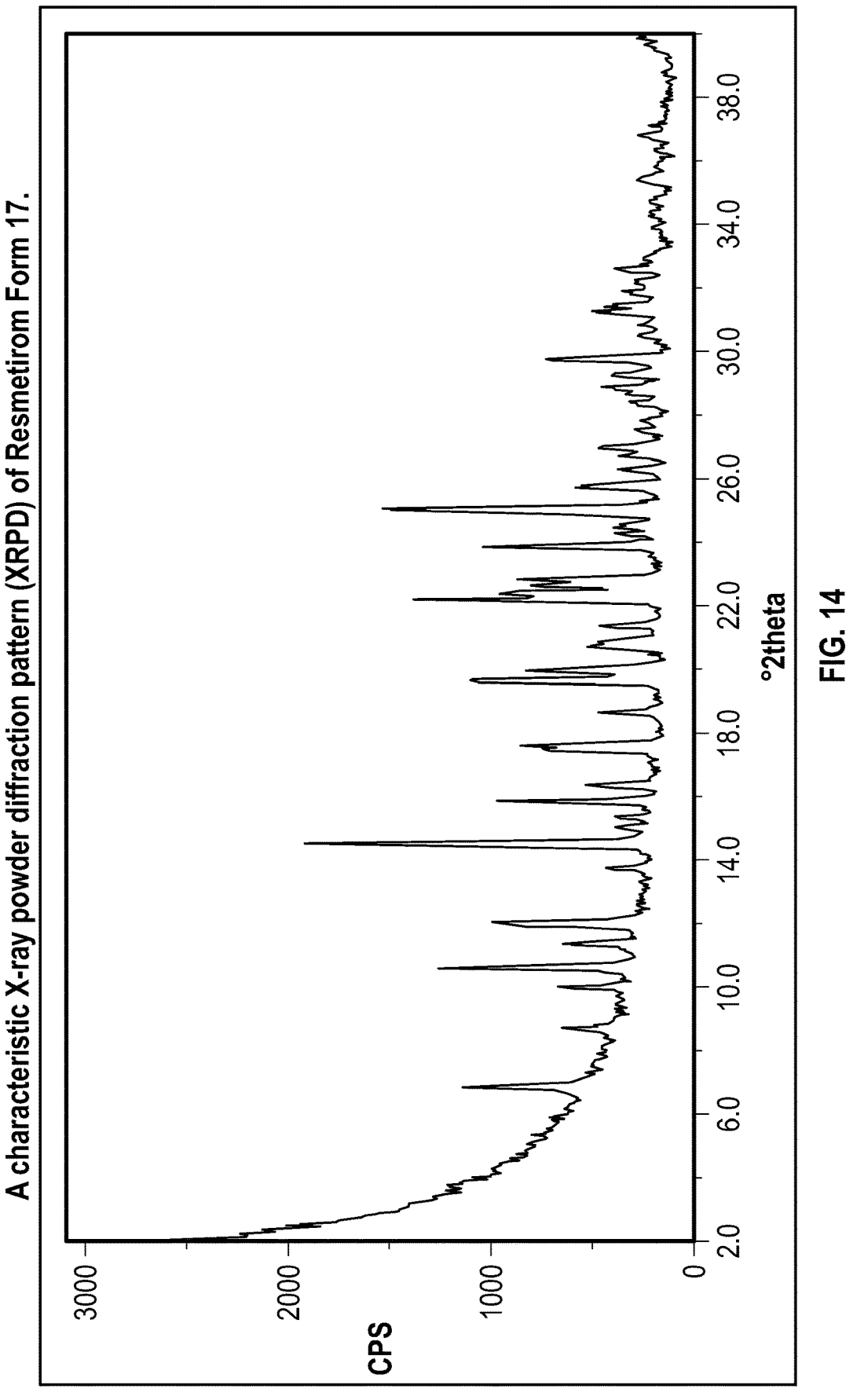
FIG. 14 shows a characteristic X-ray powder diffraction pattern (XRPD) of Resmetirom Form 17.

The present disclosure includes a crystalline polymorph Resmetirom, designated Form 17. The crystalline Form 17 of Resmetirom may be characterized by data selected from one or more of the following: an X-ray powder diffraction pattern substantially as depicted in FIG. 14; an X-ray powder diffraction pattern having peaks at 6.8, 8.7, 11.4, 14.5 and 29.7 degrees 2-theta±0.2 degrees 2-theta; and combinations of these data.

Crystalline Form 17 of Resmetirom may be further characterized by an X-ray powder diffraction pattern having peaks at 6.8, 8.7, 11.4, 14.5 and 29.7 degrees 2-theta±0.2 degrees 2-theta, and also having any one, two, three, four or five additional peaks selected from 10.1, 15.0, 15.4, 19.7 and 20.0 degrees 2-theta±0.2 degrees 2-theta.

Crystalline form 17 may be alternatively characterized by an X-ray powder diffraction pattern having peaks at 6.8, 8.7, 10.1, 11.4, 14.5, 15.0, 15.4, 19.7, 20.0 and 29.7 degrees 2-theta±0.2 degrees 2-theta.

In one embodiment of the present disclosure, crystalline Form 17 of Resmetirom is isolated. Particularly, crystalline form 17 of Resmetirom according to any aspect or embodiment of the disclosure may be isolated Crystalline Form 17 of Resmetirom may be a Methyl ethyl ketone solvate. In embodiments, crystalline form 17 of Resmetirom may contain about 12% to about 15% of methyl ethyl ketone by weight, or about 13 to about 14% or about 13.5% to about 13.9% by weight, or about 13.7% of methyl ethyl ketone by weight, as determined by TGA.

Crystalline Form 17 of Resmetirom may be characterized by each of the above characteristics alone/or by all possible combinations, e.g., an XRPD pattern having peaks at 6.8, 8.7, 11.4, 14.5 and 29.7 degrees 2-theta±0.2 degrees 2-theta; an XRPD pattern as depicted in FIG. 14, and combinations thereof.

Figure 15:
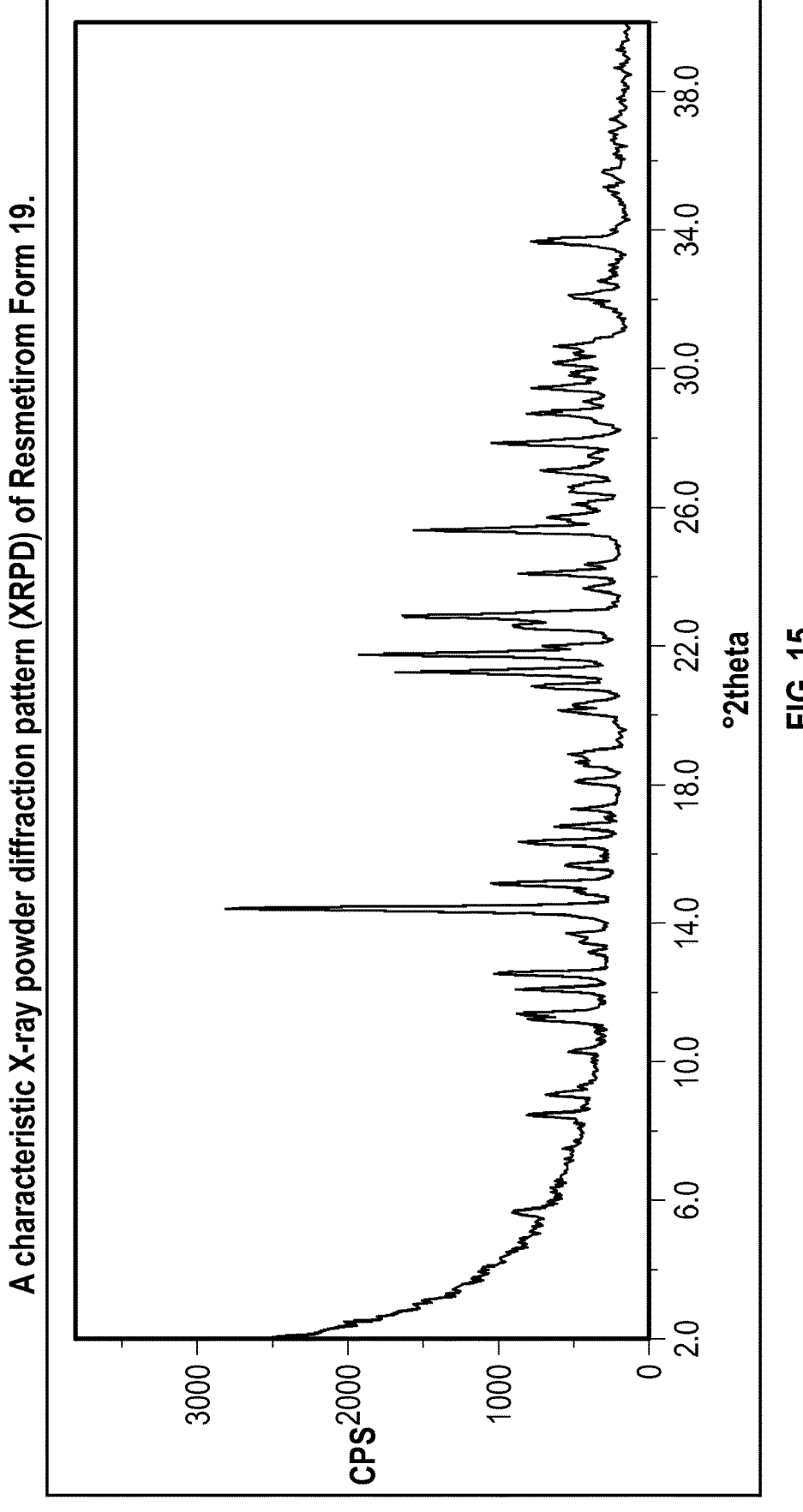
FIG. 15 shows a characteristic X-ray powder diffraction pattern (XRPD) of Resmetirom Form 19.

The present disclosure includes a crystalline polymorph Resmetirom, designated Form 19. The crystalline Form 19 of Resmetirom may be characterized by data selected from one or more of the following: an X-ray powder diffraction pattern substantially as depicted in FIG. 15; an X-ray powder diffraction pattern having peaks at 8.5, 9.1, 12.6, 14.5 and 15.2 degrees 2-theta±0.2 degrees 2-theta; and combinations of these data.

Crystalline Form 19 of Resmetirom may be further characterized by an X-ray powder diffraction pattern having peaks at 8.5, 9.1, 12.6, 14.5 and 15.2 degrees 2-theta±0.2 degrees 2-theta, and also having any one, two, three, four or five additional peaks selected from 12.1, 15.7, 20.8, 21.1 and 25.4 degrees 2-theta±0.2 degrees 2-theta.

Crystalline form 19 may be alternatively characterized by an X-ray powder diffraction pattern having peaks at 8.5, 9.1, 12.1, 12.6, 14.5, 15.2, 15.7, 20.8, 21.1 and 25.4 degrees 2-theta±0.2 degrees 2-theta.

In one embodiment of the present disclosure, crystalline Form 19 of Resmetirom is isolated.

Crystalline Form 19 of Resmetirom may be a Toluene solvate.

Crystalline Form 19 of Resmetirom may be characterized by each of the above characteristics alone/or by all possible combinations, e.g., an XRPD pattern having peaks at 8.5, 9.1, 12.6, 14.5 and 15.2 degrees 2-theta±0.2 degrees 2-theta; an XRPD pattern as depicted in FIG. 15, and combinations thereof.

Figure 16:
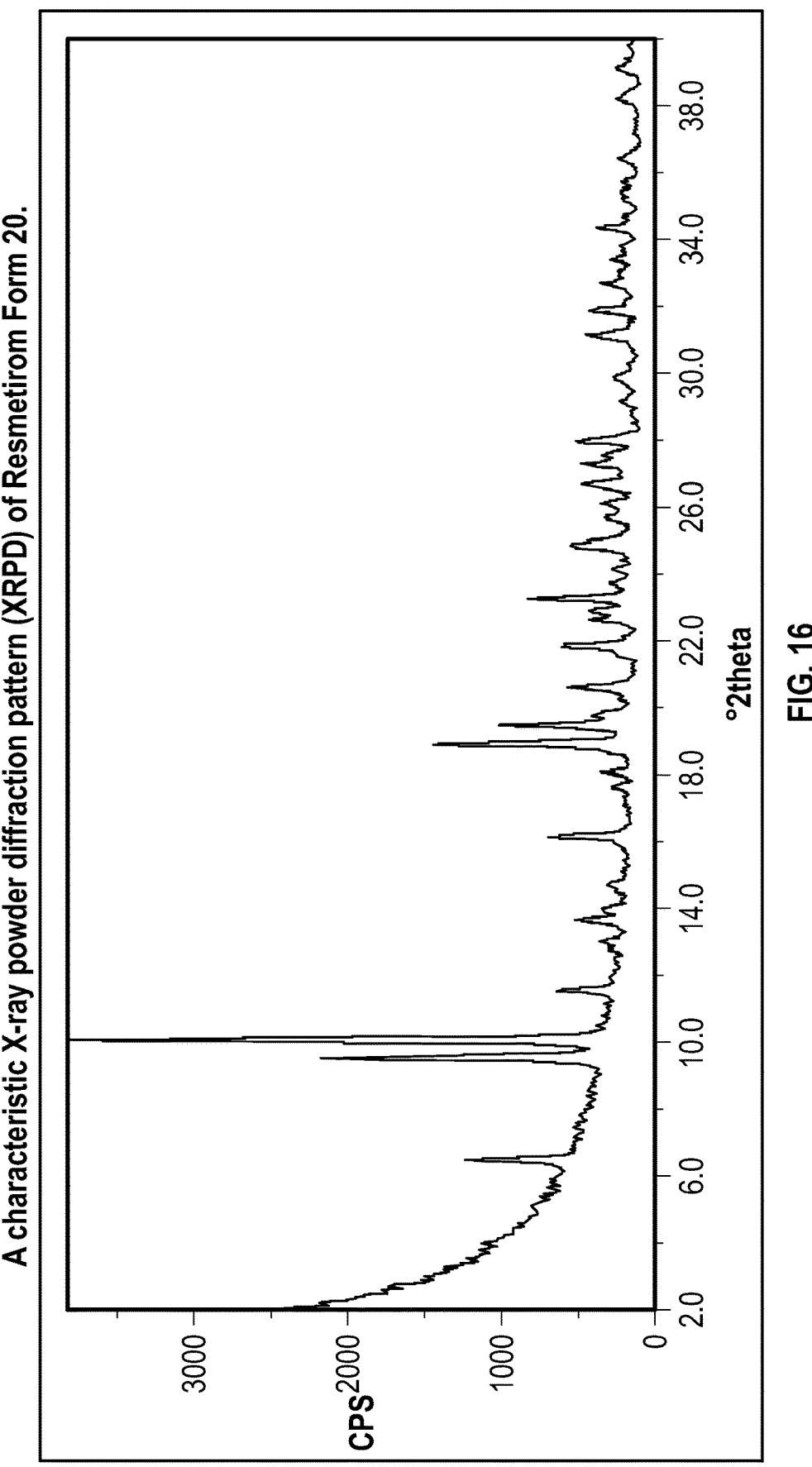
FIG. 16 shows a characteristic X-ray powder diffraction pattern (XRPD) of Resmetirom Form 20.
Figure 28:
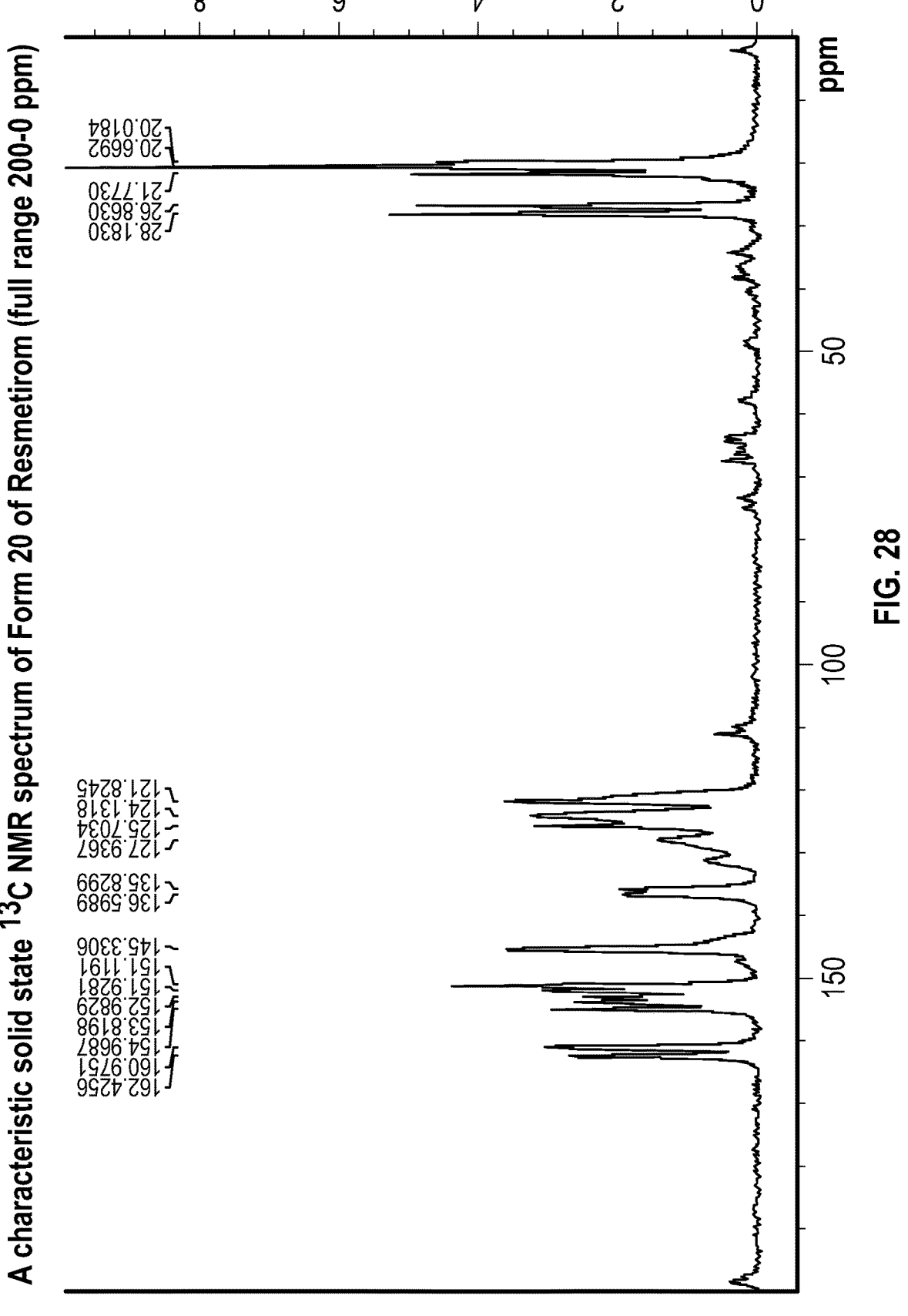
FIG. 28 shows a characteristic solid state $^{13}$C NMR spectrum of Form 20 of Resmetirom (full range 200-0 ppm).
Figure 29:
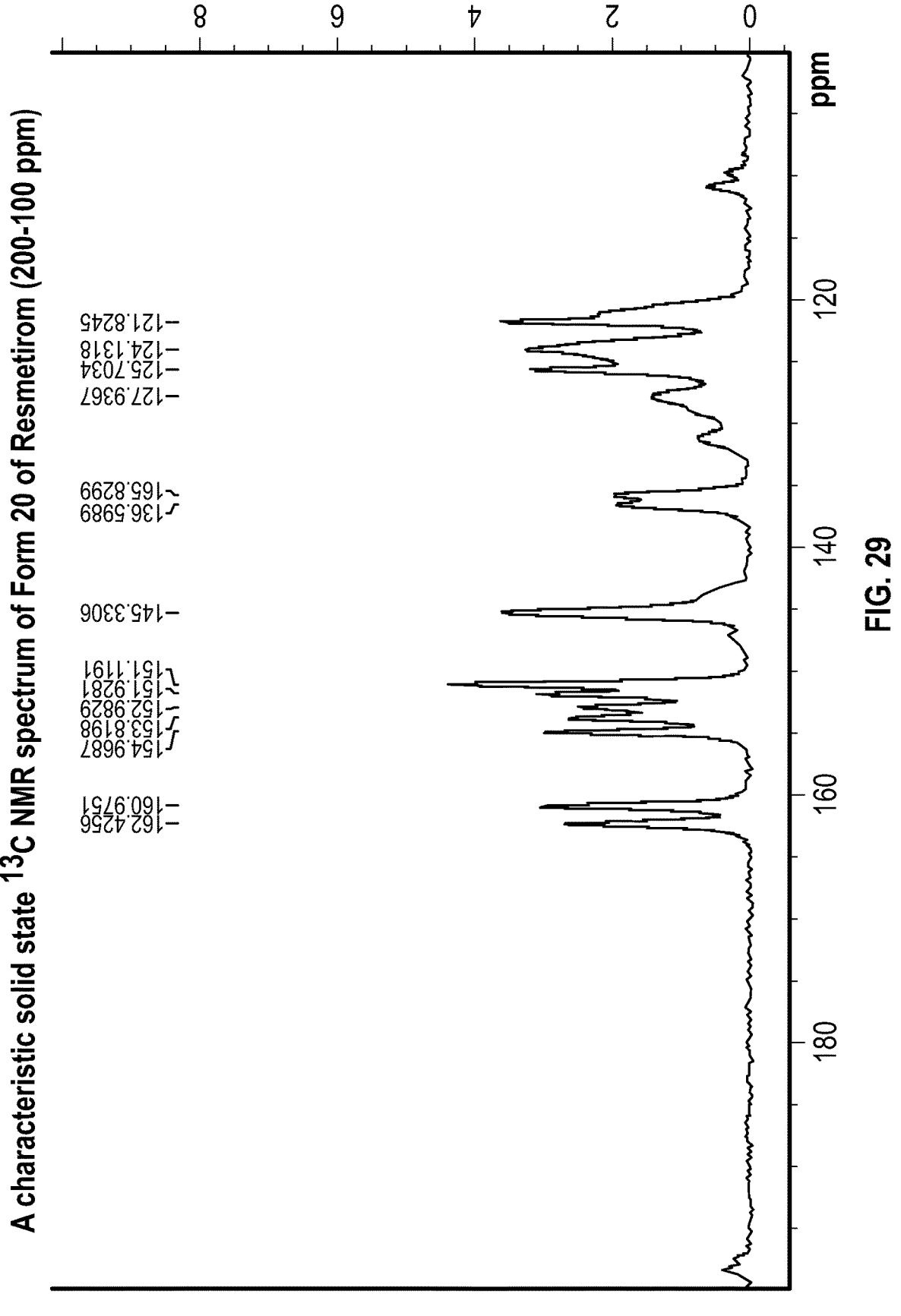
FIG. 29 shows a characteristic solid state $^{13}$C NMR spectrum of Form 20 of Resmetirom (200-100 ppm).
Figure 30:
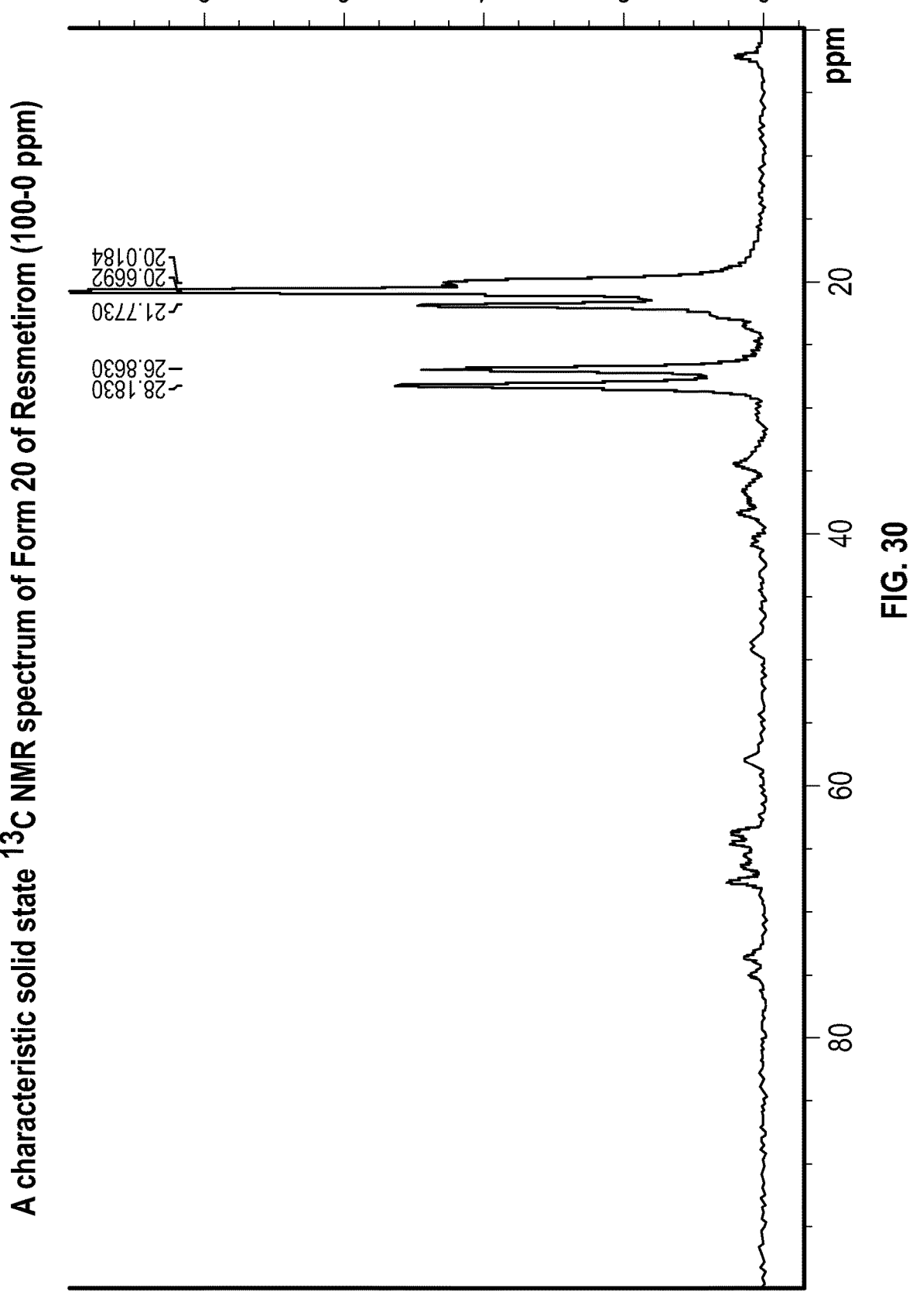
FIG. 30 shows a characteristic solid state $^{13}$C NMR spectrum of Form 20 of Resmetirom (100-0 ppm).

The present disclosure includes a crystalline polymorph Resmetirom, designated Form 20. The crystalline Form 20 of Resmetirom may be characterized by data selected from one or more of the following: an X-ray powder diffraction pattern substantially as depicted in FIG. 16; an X-ray powder diffraction pattern having peaks at 6.5, 9.6, 10.1, 19.0 and 23.3 degrees 2-theta±0.2 degrees 2-theta; a solid state $^{13}$C NMR spectrum with characteristic peaks at 161.0, 155.0, 151.1, 145.3 and 121.8 ppm±0.2 ppm; a solid state $^{13}$C NMR spectrum having the following chemical shift absolute differences from reference peak at 162.4 ppm±1 ppm: 1.4, 7.5, 11.3, 17.1 and 40.6 ppm±0.1 ppm; a solid state $^{13}$C NMR spectrum substantially as depicted in FIG. 28, 29 or 30; and combinations of these data.

Crystalline Form 20 of Resmetirom may be further characterized by an X-ray powder diffraction pattern having peaks at 6.5, 9.6, 10.1, 19.0 and 23.3 degrees 2-theta±0.2 degrees 2-theta, and also having any one, two, three, four or five additional peaks selected from 11.6, 16.2, 19.5, 21.8 and 24.9 degrees 2-theta±0.2 degrees 2-theta.

Crystalline form 20 may be alternatively characterized by an X-ray powder diffraction pattern having peaks at 6.5, 9.6, 10.1, 11.6, 16.2, 19.0, 19.5, 21.8, 23.3 and 24.9 degrees 2-theta±0.2 degrees 2-theta.

In one embodiment of the present disclosure, crystalline Form 20 of Resmetirom is isolated. Particularly, crystalline form 20 of Resmetirom according to any aspect or embodiment of the disclosure may be isolated.

Crystalline form 20 according to any aspect or embodiment of the disclosure may be anhydrous.

In any aspect or embodiment of the present disclosure, crystalline Form 20 of Resmetirom is non-hygroscopic. Particularly, Form 20 of Resmetirom according to any aspect or embodiment is polymorphically stable at up to 80% relative humidity at room temperature for at least 7 days.

Crystalline Form 20 of Resmetirom may be characterized by each of the above characteristics alone/or by all possible combinations, e.g., an XRPD pattern having peaks at 6.5, 9.6, 10.1, 19.0 and 23.3 degrees 2-theta±0.2 degrees 2-theta; an XRPD pattern as depicted in FIG. 16, and combinations thereof.

Figure 17:
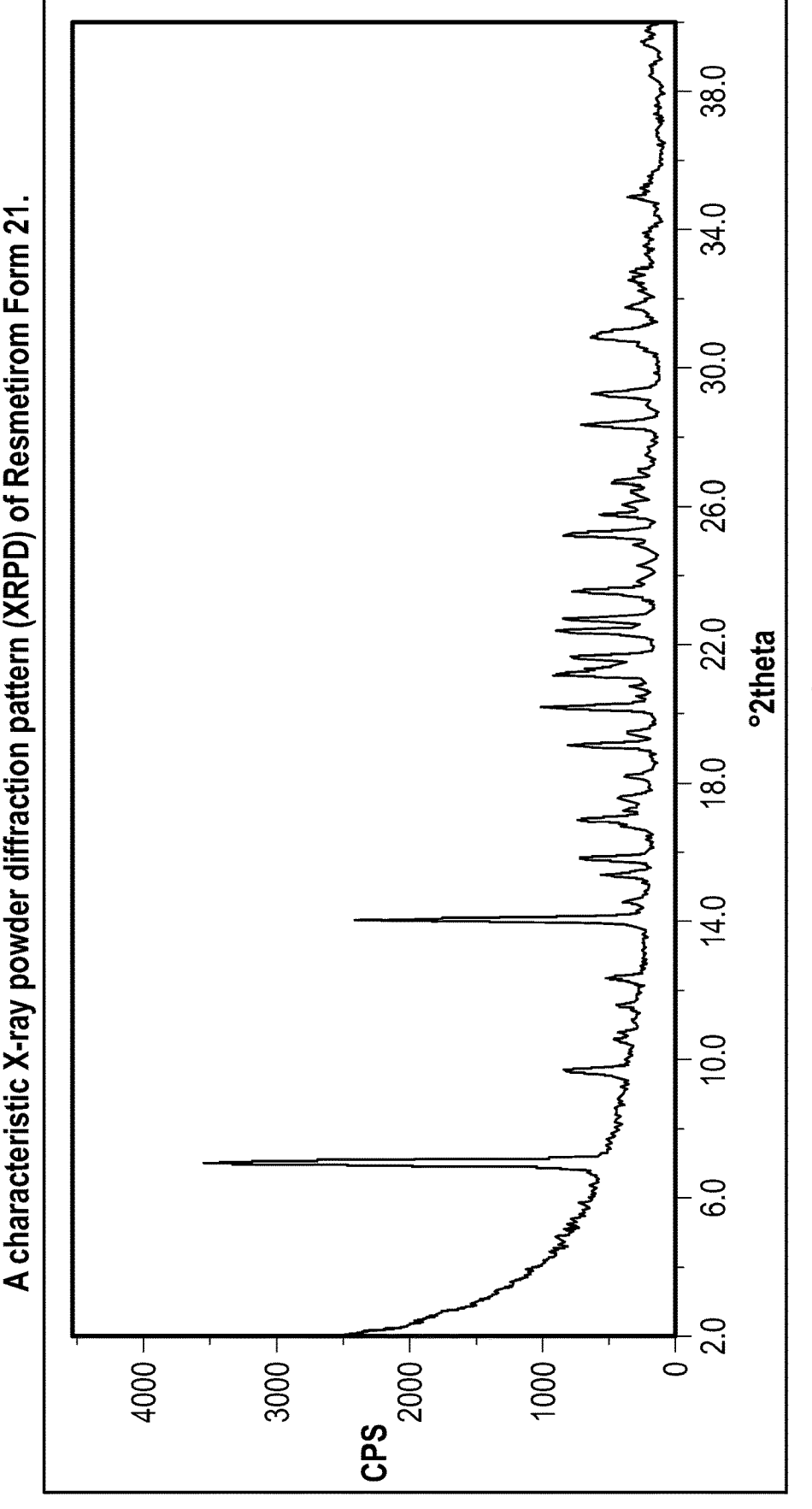
FIG. 17 shows a characteristic X-ray powder diffraction pattern (XRPD) of Resmetirom Form 21.

The present disclosure includes a crystalline polymorph Resmetirom, designated Form 21. The crystalline Form 21 of Resmetirom may be characterized by data selected from one or more of the following: an X-ray powder diffraction pattern substantially as depicted in FIG. 17; an X-ray powder diffraction pattern having peaks at 7.0, 14.1, 15.9, 20.2 and 28.4 degrees 2-theta±0.2 degrees 2-theta; and combinations of these data.

Crystalline Form 21 of Resmetirom may be further characterized by an X-ray powder diffraction pattern having peaks at 7.0, 14.1, 15.9, 20.2 and 28.4 degrees 2-theta±0.2 degrees 2-theta, and also having any one, two, three, four or five additional peaks selected from 12.4, 17.0, 25.1, 25.8 and 29.3 degrees 2-theta±0.2 degrees 2-theta.

Crystalline form 21 may be alternatively characterized by an X-ray powder diffraction pattern having peaks at 7.0, 12.4, 14.1, 15.9, 17.0, 20.2, 25.1, 25.8, 28.4 and 29.3 degrees 2-theta±0.2 degrees 2-theta.

In one embodiment of the present disclosure, crystalline Form 21 of Resmetirom is isolated.

Crystalline Form 21 of Resmetirom may be an Acetonitrile solvate.

Crystalline Form 21 of Resmetirom may be characterized by each of the above characteristics alone/or by all possible combinations, e.g., an XRPD pattern having peaks at 7.0, 14.1, 15.9, 20.2 and 28.4 degrees 2-theta±0.2 degrees 2-theta; an XRPD pattern as depicted in FIG. 17, and combinations thereof.

Figure 18:
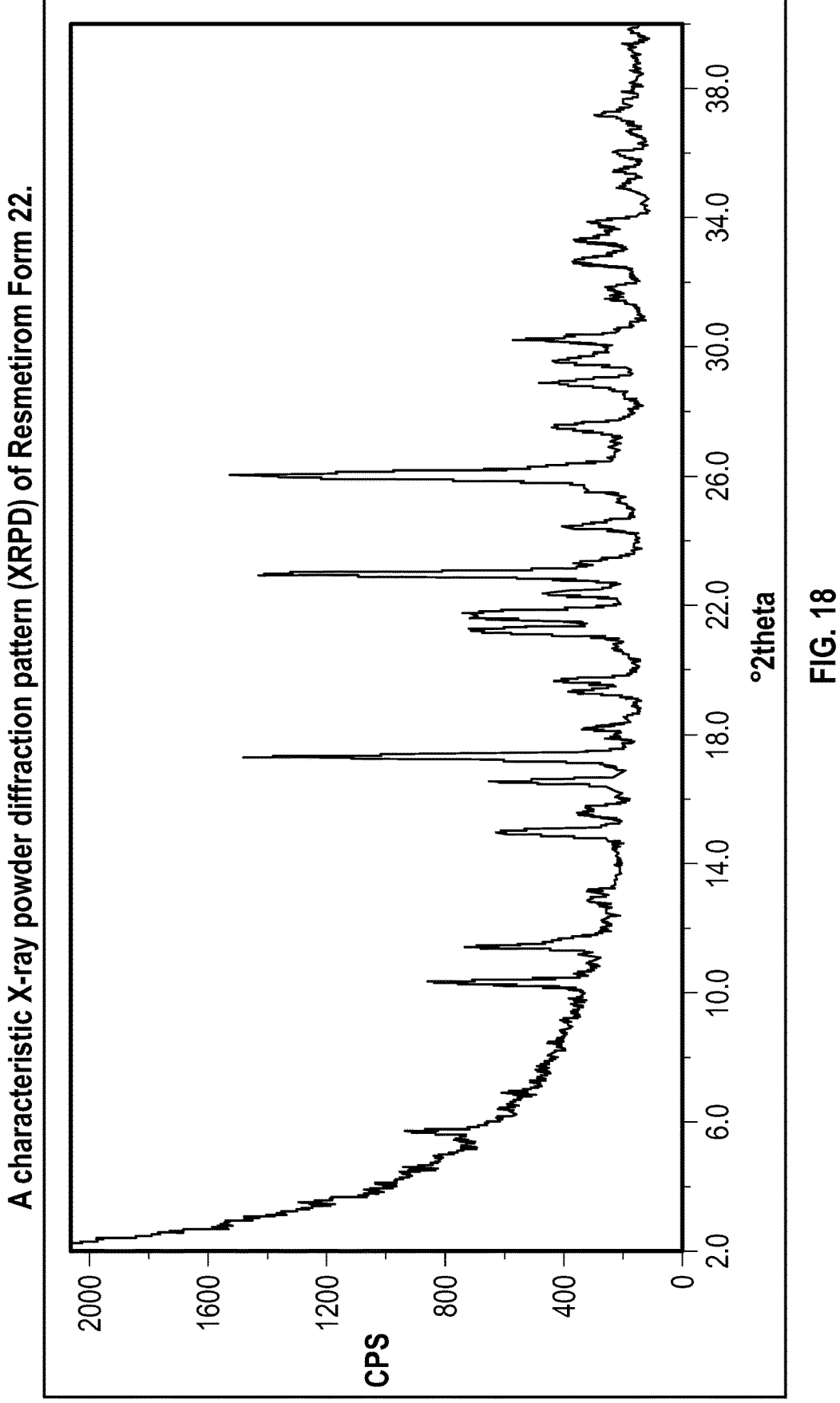
FIG. 18 shows a characteristic X-ray powder diffraction pattern (XRPD) of Resmetirom Form 22.

The present disclosure includes a crystalline polymorph Resmetirom, designated Form 22. The crystalline Form 22 of Resmetirom may be characterized by data selected from one or more of the following: an X-ray powder diffraction pattern substantially as depicted in FIG. 18; an X-ray powder diffraction pattern having peaks at 5.6, 15.0, 16.6, 17.4 and 23.0 degrees 2-theta±0.2 degrees 2-theta; and combinations of these data.

Crystalline Form 22 of Resmetirom may be further characterized by an X-ray powder diffraction pattern having peaks at 5.6, 15.0, 16.6, 17.4 and 23.0 degrees 2-theta±0.2 degrees 2-theta, and also having any one, two, three, four or five additional peaks selected from 11.5, 23.3, 26.1, 27.6 and 28.9 degrees 2-theta±0.2 degrees 2-theta.

Crystalline form 22 may be alternatively characterized by an X-ray powder diffraction pattern having peaks at 5.6, 11.5, 15.0, 16.6, 17.4, 23.0, 23.3, 26.1, 27.6 and 28.9 degrees 2-theta±0.2 degrees 2-theta.

In one embodiment of the present disclosure, crystalline Form 22 of Resmetirom is isolated.

Crystalline Form 22 of Resmetirom may be an Ethylene glycol solvate.

Crystalline Form 22 of Resmetirom may be characterized by each of the above characteristics alone/or by all possible combinations, e.g., an XRPD pattern having peaks at 5.6, 15.0, 16.6, 17.4 and 23.0 degrees 2-theta±0.2 degrees 2-theta; an XRPD pattern as depicted in FIG. 18, and combinations thereof.

Figure 19:
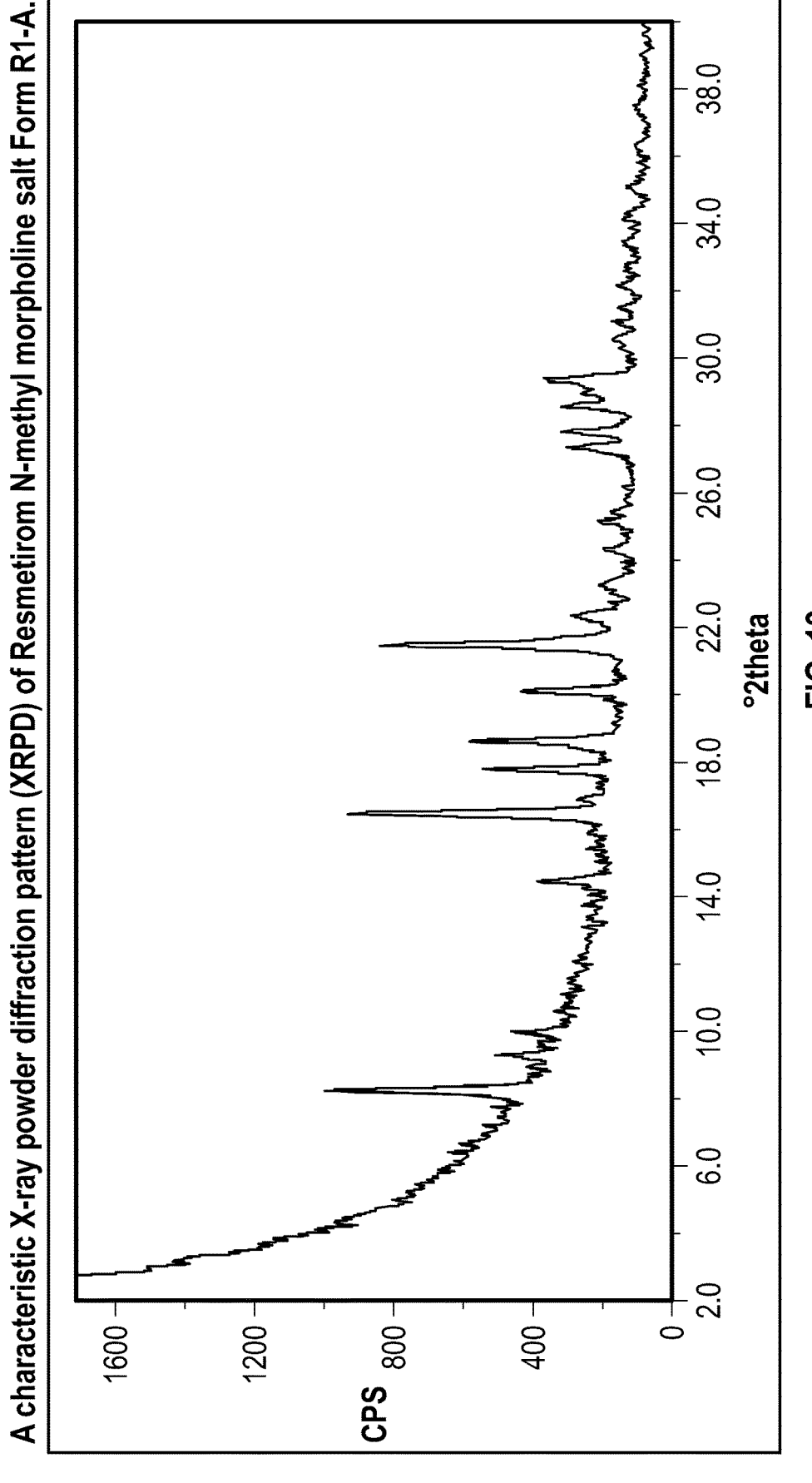
FIG. 19 shows a characteristic X-ray powder diffraction pattern (XRPD) of Resmetirom N-methyl morpholine salt Form R1-A.

The present disclosure includes a crystalline polymorph Resmetirom N-methylmorpholine salt designated Form R1-A. The crystalline Form R1-A of Resmetirom N-methylmorpholine salt may be characterized by data selected from one or more of the following: an X-ray powder diffraction pattern substantially as depicted in FIG. 19; an X-ray powder diffraction pattern having peaks at 8.2, 16.5, 17.8, 18.6 and 21.5 degrees 2-theta±0.2 degrees 2-theta; and combinations of these data.

Crystalline Form R1-A of Resmetirom N-methylmorpholine salt may be further characterized by an X-ray powder diffraction pattern having peaks at 8.2, 16.5, 17.8, 18.6 and 21.5 degrees 2-theta±0.2 degrees 2-theta, and also having any one, two, three, four or five additional peaks selected from 10.0, 14.5, 20.2, 22.4 and 27.4 degrees 2-theta±0.2 degrees 2-theta.

Crystalline Form R1-A of Resmetirom N-methylmorpholine salt may be further characterized by an X-ray powder diffraction pattern having peaks at 8.2, 10.0, 14.5, 16.5, 17.8, 18.6, 20.2, 21.5, 22.4, and 27.4 degrees 2-theta±0.2 degrees 2-theta.

In one embodiment of the present disclosure, crystalline Form R1-A of Resmetirom N-methylmorpholine salt is isolated.

Crystalline Form R1-A of Resmetirom N-methylmorpholine salt may be characterized by each of the above characteristics alone/or by all possible combinations, e.g., an XRPD pattern having peaks at 8.2, 16.5, 17.8, 18.6 and 21.5 degrees 2-theta±0.2 degrees 2-theta; an XRPD pattern as depicted in FIG. 19, and combinations thereof.

The present disclosure includes Resmetirom piperazine salt, optionally in crystalline form. In embodiments the molar ratio of Resmetirom to piperazine is typically about 2:1. In embodiments, crystalline Resmetirom piperazine is Form R2-A.

Figure 20:
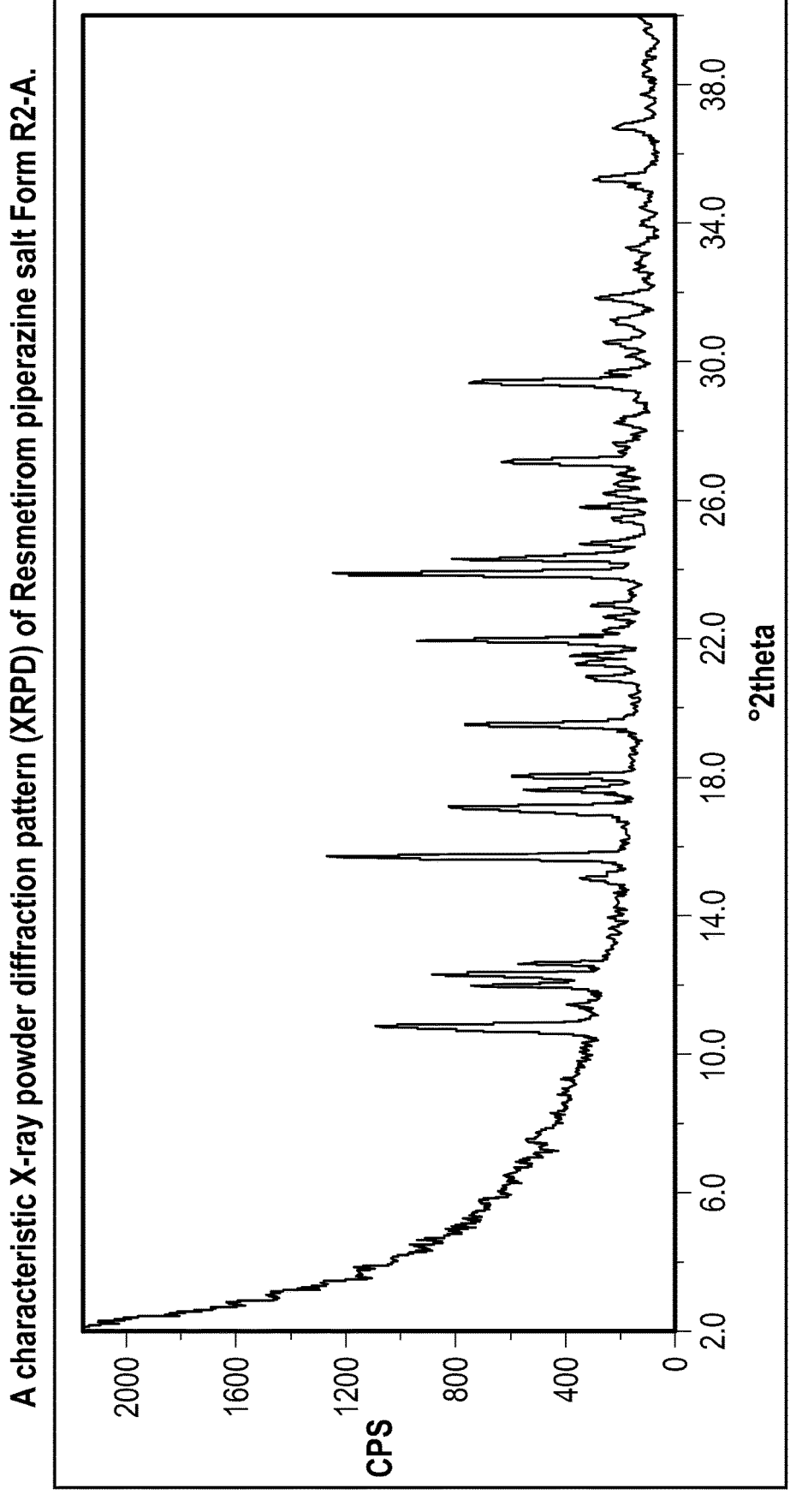
FIG. 20 shows a characteristic X-ray powder diffraction pattern (XRPD) of Resmetirom piperazine salt Form R2-A.
Figure 43:
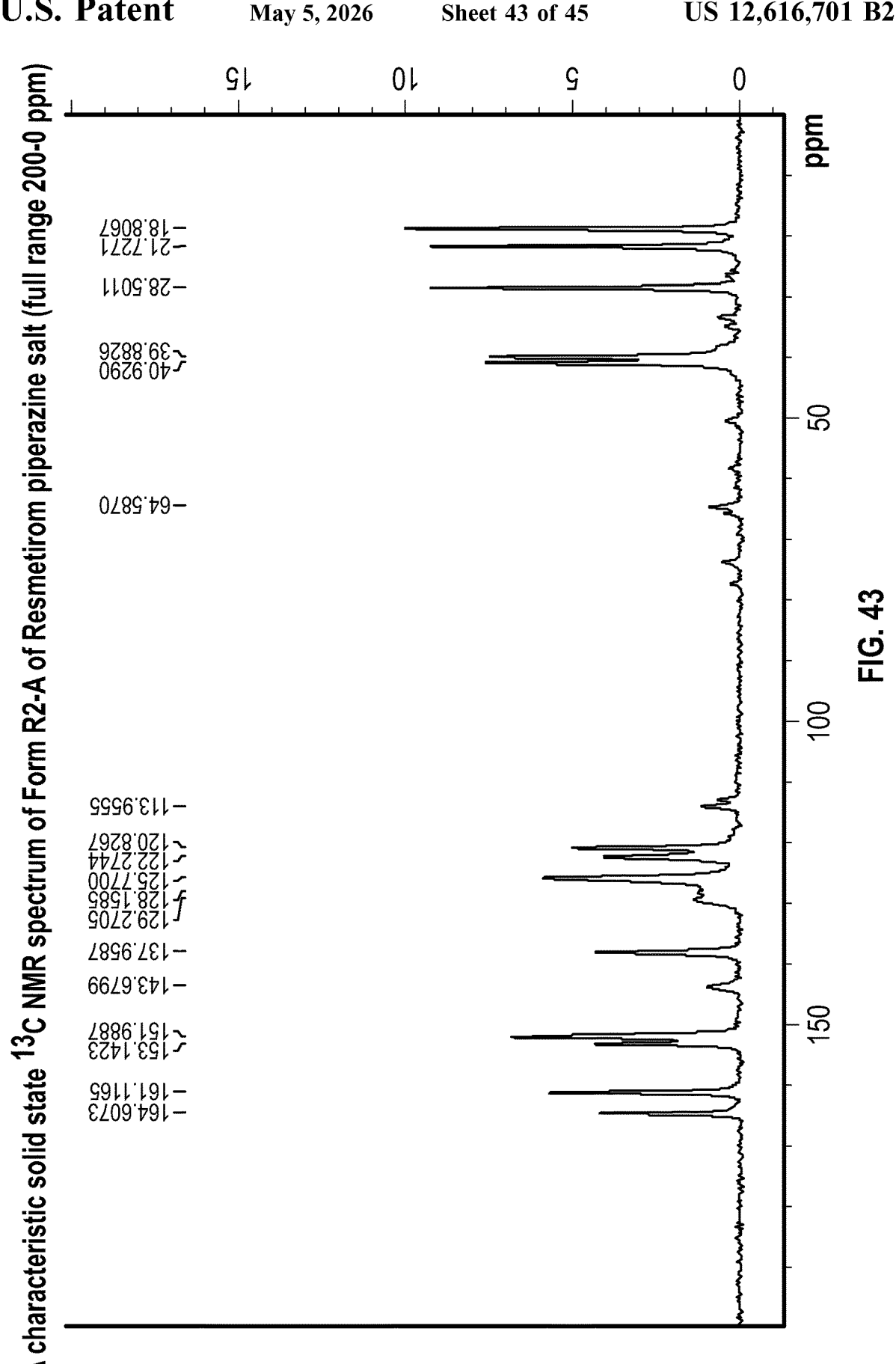
FIG. 43 shows a characteristic solid state $^{13}$C NMR spectrum of Form R2-A of Resmetirom piperazine salt (full range 200-0 ppm).
Figure 44:
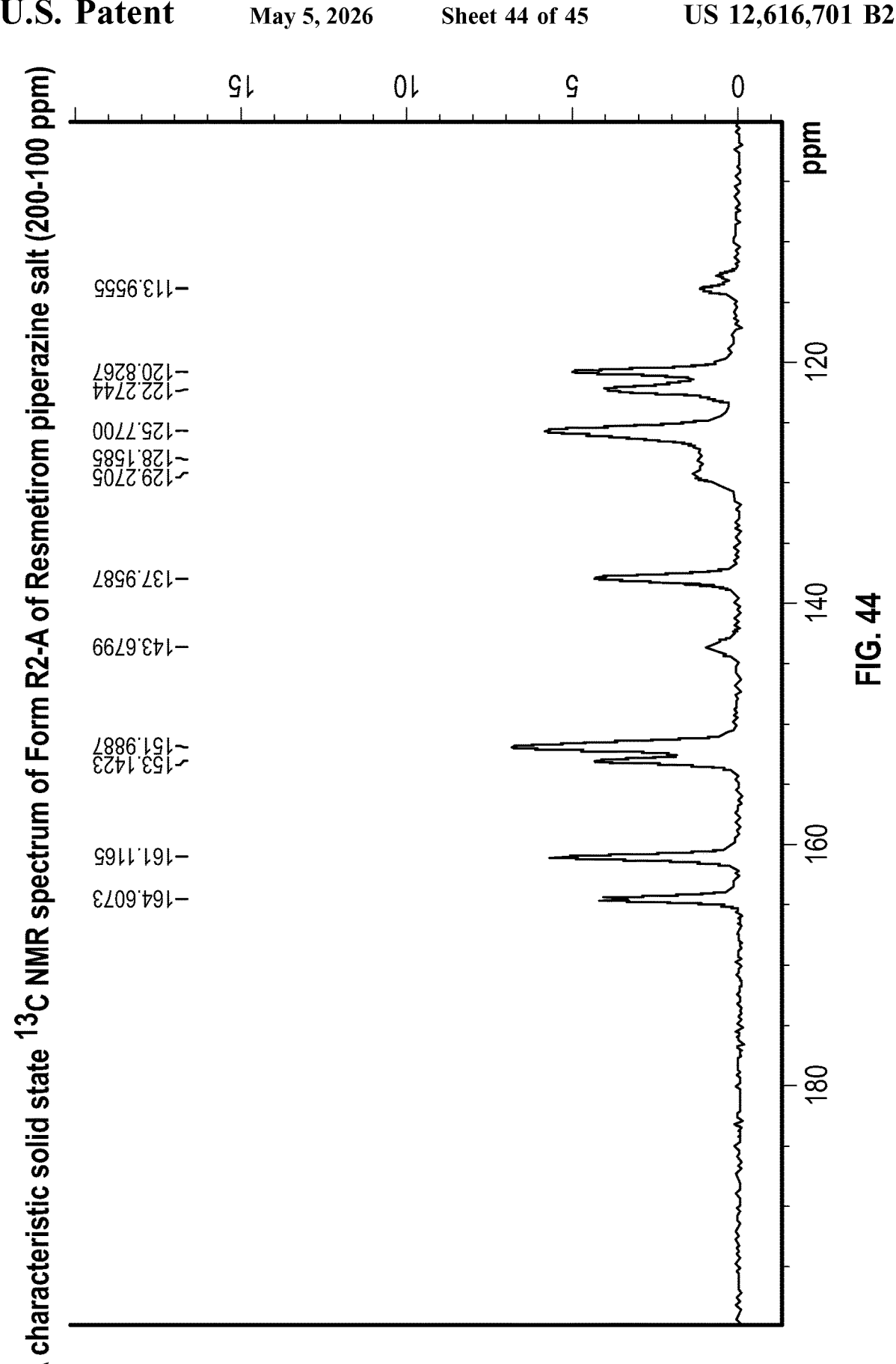
FIG. 44 shows a characteristic solid state $^{13}$C NMR spectrum of Form R2-A of Resmetirom piperazine salt (200-100 ppm).
Figure 45:
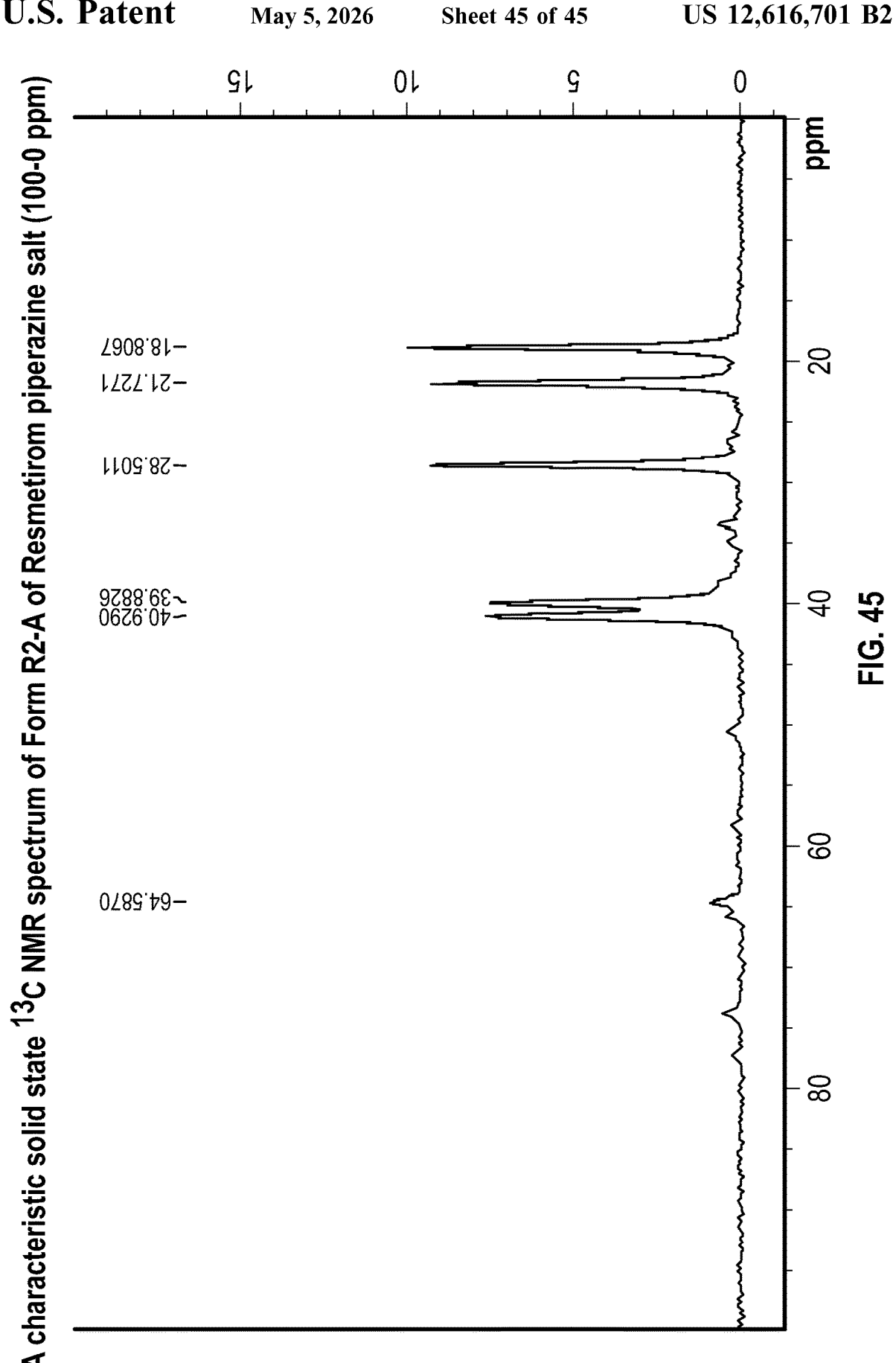
FIG. 45 shows a characteristic solid state $^{13}$C NMR spectrum of Form R2-A of Resmetirom piperazine salt (100-0 ppm).

The crystalline Form R2-A of Resmetirom piperazine salt may be characterized by data selected from one or more of the following: an X-ray powder diffraction pattern substantially as depicted in FIG. 20; an X-ray powder diffraction pattern having peaks at 10.7, 15.7, 19.5, 22.0 and 23.9 degrees 2-theta±0.2 degrees 2-theta; a solid state $^{13}$C NMR spectrum with characteristic peaks at 161.1, 152.0, 138.0, 40.9 and 39.9 ppm±0.2 ppm; a solid state 13C NMR spectrum having the following chemical shift absolute differences from reference peak at 164.6 ppm±1 ppm: 3.5, 12.6, 26.6, 123.7 and 124.7 ppm±0.1 ppm; a solid state $^{13}$C NMR spectrum substantially as depicted in FIG. 43, 44 or 45; and combinations of these data.

Crystalline Form R2-A of Resmetirom piperazine salt may be further characterized by an X-ray powder diffraction pattern having peaks at 10.7, 15.7, 19.5, 22.0 and 23.9 degrees 2-theta±0.2 degrees 2-theta, and also having any one, two, three, four or five additional peaks selected from 12.0, 12.3, 12.6, 17.1 and 21.5 degrees 2-theta±0.2 degrees 2-theta.

Crystalline form R2-A of Resmetirom piperazine salt may be alternatively characterized by an X-ray powder diffraction pattern having peaks at 10.7, 12.0, 12.3, 12.6, 15.7, 17.1, 19.5, 21.5, 22.0 and 23.9 degrees 2-theta±0.2 degrees 2-theta.

In one embodiment of the present disclosure, crystalline Form R2-A of Resmetirom piperazine salt is isolated. Particularly, crystalline form R2-A of Resmetirom piperazine salt according to any aspect or embodiment of the disclosure may be isolated.

Crystalline form R2-A of Resmetirom piperazine salt according to any aspect or embodiment of the disclosure may be anhydrous.

In any aspect or embodiment of the present disclosure, crystalline Form R2-A of Resmetirom piperazine salt is non-hygroscopic. Particularly, Form R2-A of Resmetirom piperazine salt according to any aspect or embodiment is polymorphically stable at up to 100% relative humidity at room temperature for at least 7 days.

Crystalline Form R2-A of Resmetirom piperazine salt may be characterized by each of the above characteristics alone/or by all possible combinations, e.g., an XRPD pattern having peaks at 10.7, 15.7, 19.5, 22.0 and 23.9 degrees 2-theta±0.2 degrees 2-theta; an XRPD pattern as depicted in FIG. 20, and combinations thereof.

The present disclosure relates to Resmetirom:L-proline. Particularly, the present disclosure includes a crystalline polymorph Resmetirom L-proline salt or Resmetirom L-proline cocrystal designated Form R3-A. In any aspect or embodiment of the disclosure, Resmetirom:L-proline Form R3-A may be Resmetirom L-proline salt, optionally, wherein the molar ratio of Resmetirom to L-proline is about 1:1. Preferably, in any aspect or embodiment of the disclosure, the Resmetirom L-proline Form R3-A may be a cocrystal of Resmetirom with L-proline, optionally wherein the molar ratio of L-proline to Resmetirom in form R3-A is typically about 1:1.

Figure 21:
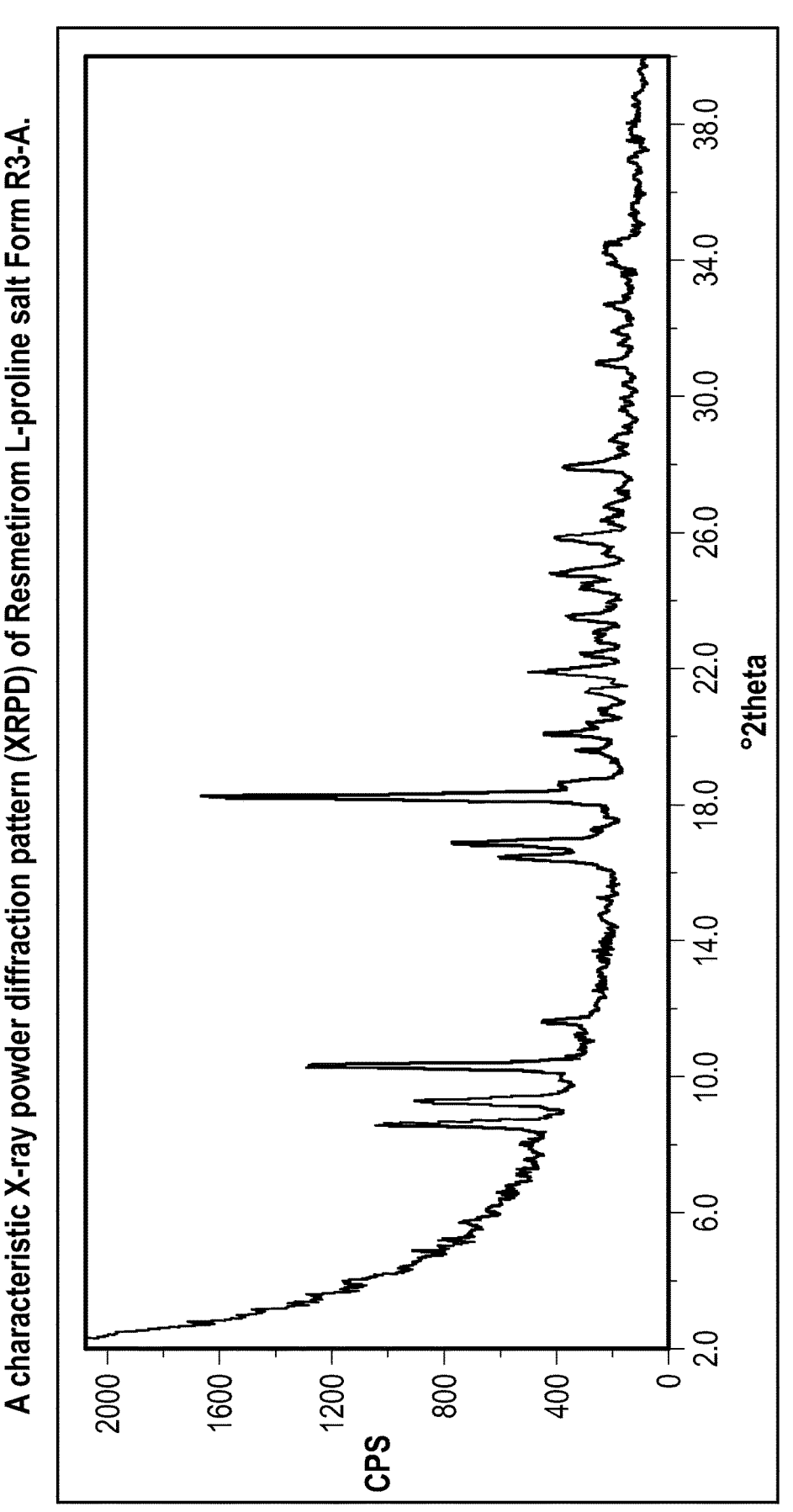
FIG. 21 shows a characteristic X-ray powder diffraction pattern (XRPD) of Resmetirom:L-proline Form R3-A.
Figure 40:
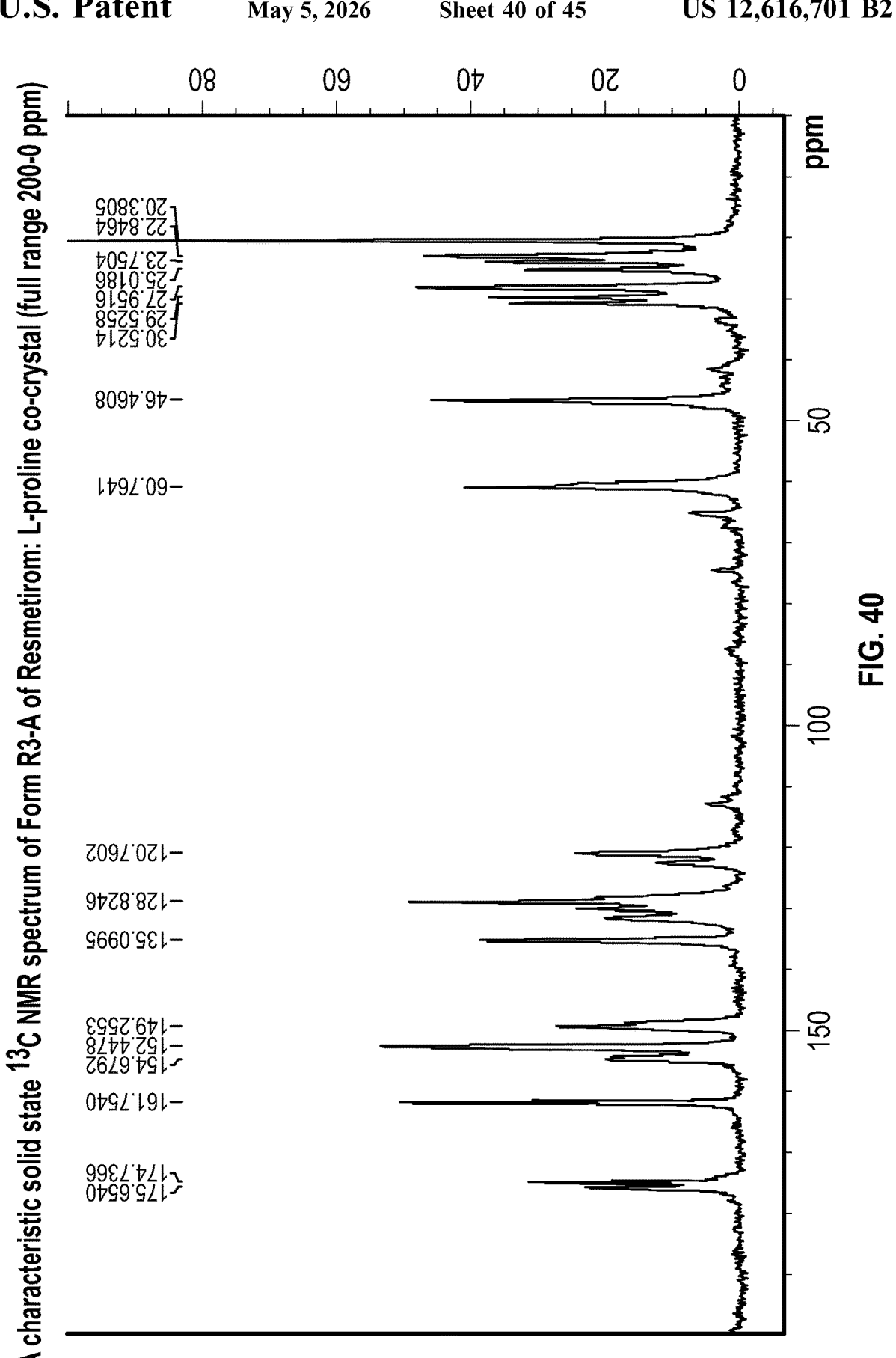
FIG. 40 shows a characteristic solid state $^{13}$C NMR spectrum of Form R3-A of Resmetirom:L-proline co-crystal (full range 200-0 ppm).
Figure 41:
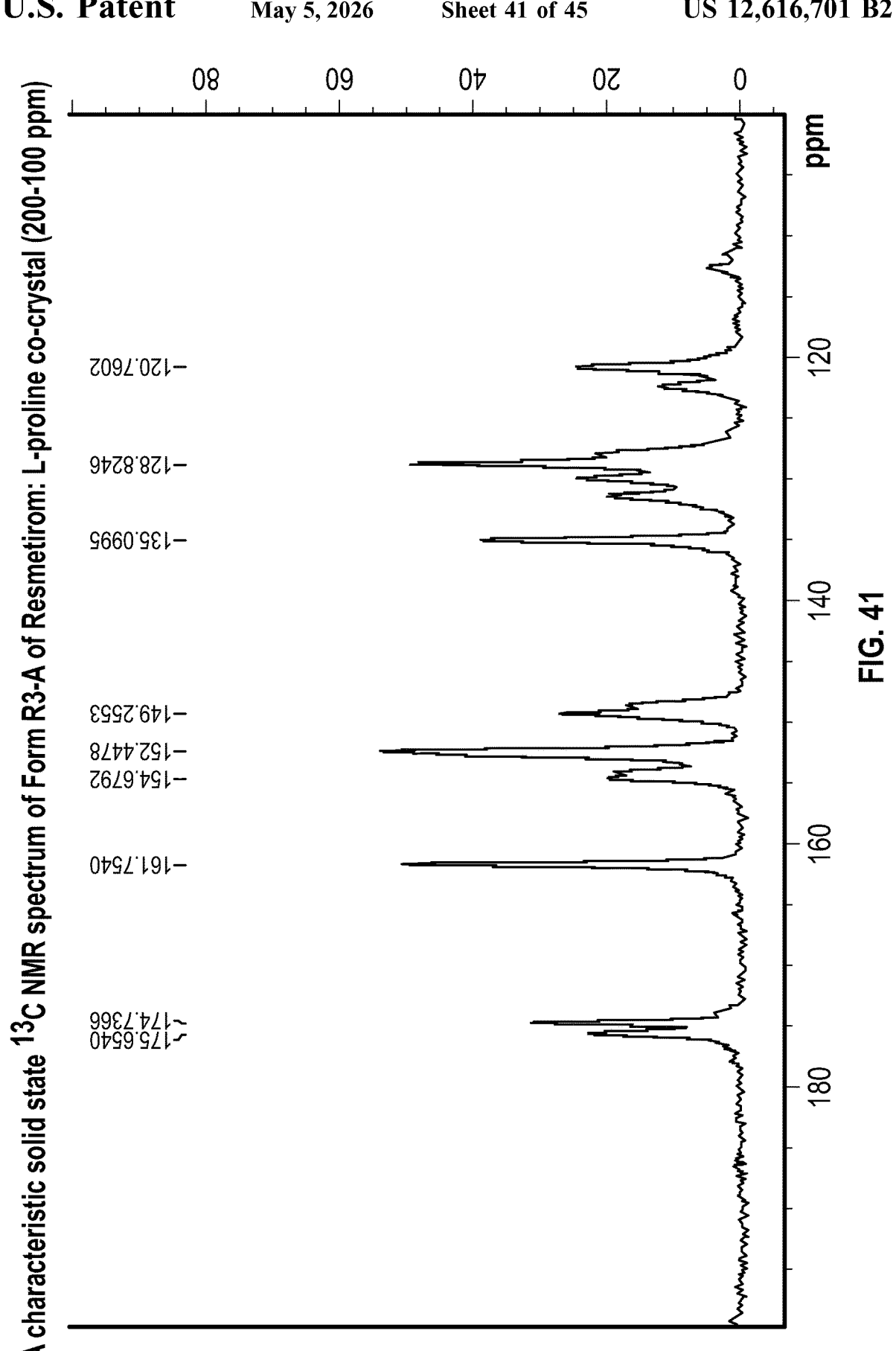
FIG. 41 shows a characteristic solid state $^{13}$C NMR spectrum of Form R3-A of Resmetirom:L-proline co-crystal (200-100 ppm).
Figure 42:
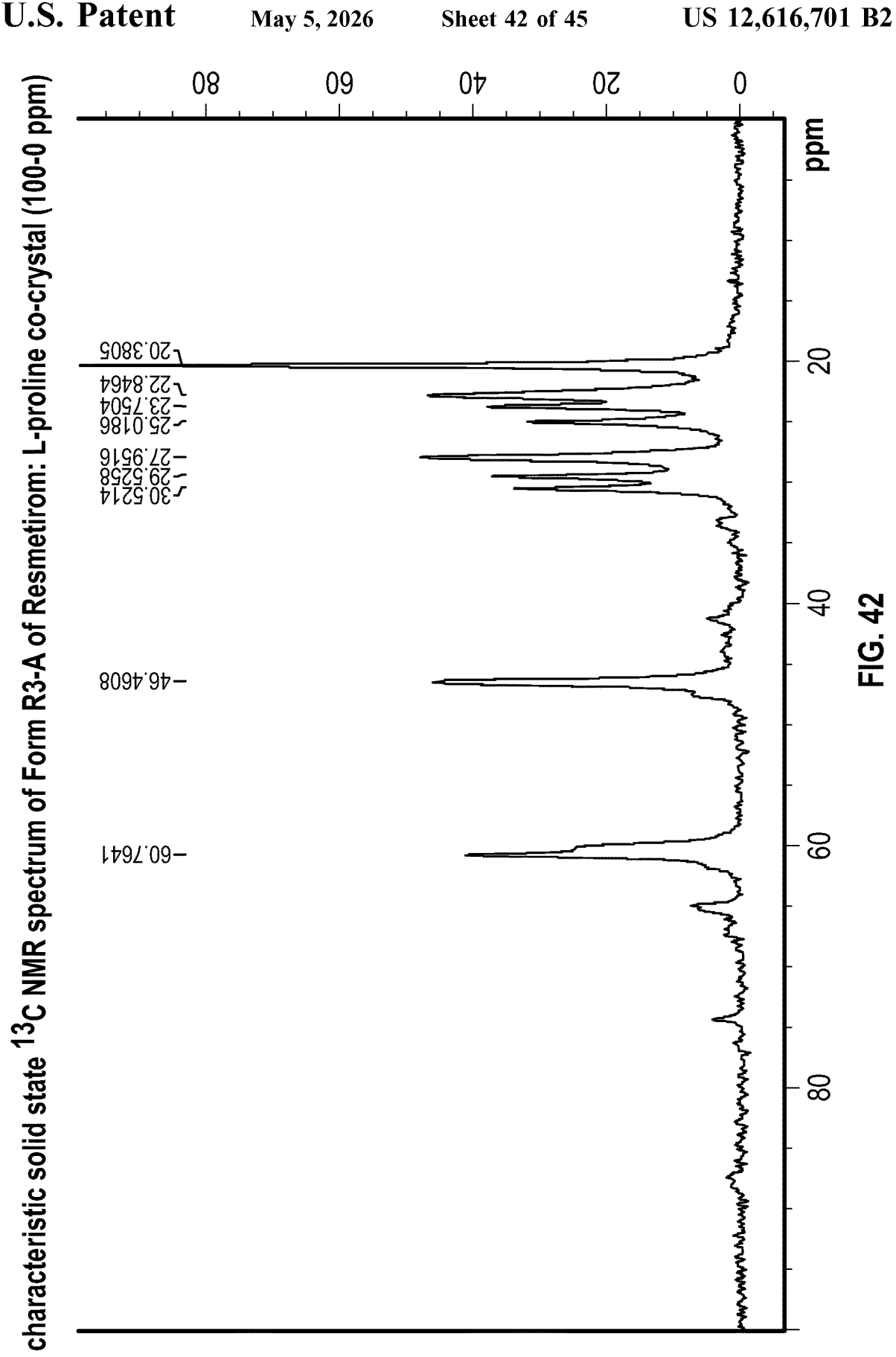
FIG. 42 shows a characteristic solid state $^{13}$C NMR spectrum of Form R3-A of Resmetirom:L-proline co-crystal (100-0 ppm).

The crystalline Form R3-A of Resmetirom L-proline salt or cocrystal may be characterized by data selected from one or more of the following: an X-ray powder diffraction pattern substantially as depicted in FIG. 21; an X-ray powder diffraction pattern having peaks at 8.6, 9.3, 10.3, 16.9 and 18.3 degrees 2-theta±0.2 degrees 2-theta; a solid state $^{13}$C NMR spectrum with characteristic peaks at 161.7, 152.4, 135.1, 60.8 and 46.5 ppm±0.2 ppm; a solid state $^{13}$C NMR spectrum having the following chemical shift absolute differences from reference peak at 174.7 ppm±1 ppm: 13.0, 22.3, 39.6, 114.0 and 128.3 ppm±0.1 ppm; a solid state 13C NMR spectrum substantially as depicted in FIG. 40, 41 or 42; and combinations of these data.

Crystalline Form R3-A of Resmetirom L-proline salt or co-crystal may be further characterized by an X-ray powder diffraction pattern having peaks at 8.6, 9.3, 10.3, 16.9 and 18.3 degrees 2-theta±0.2 degrees 2-theta, and also having any one, two, three, four or five additional peaks selected from 16.4, 20.1, 21.9, 24.8 and 25.8 degrees 2-theta±0.2 degrees 2-theta.

Crystalline form R3-A of Resmetirom L-proline salt or co-crystal may be alternatively characterized by an X-ray powder diffraction pattern having peaks at 8.6, 9.3, 10.3, 16.4, 16.9, 18.3, 20.1, 21.9, 24.8 and 25.8 degrees 2-theta±0.2 degrees 2-theta.

In one embodiment of the present disclosure, crystalline Form R3-A of Resmetirom L-proline salt or co-crystal is isolated. Particularly, crystalline form R3-A of Resmetirom L-proline salt or co-crystal according to any aspect or embodiment of the disclosure may be isolated.

Crystalline form R3-A of Resmetirom L-proline salt or co-crystal according to any aspect or embodiment of the disclosure may be anhydrous.

In any aspect or embodiment of the present disclosure, crystalline Form R3-A of Resmetirom L-proline salt or co-crystal is non-hygroscopic. Particularly, Form R3-A of Resmetirom L-proline salt or co-crystal according to any aspect or embodiment is polymorphically stable at up to 80% relative humidity at room temperature for at least 7 days.

Crystalline Form R3-A of Resmetirom:L-proline salt or co-crystal may be characterized by each of the above characteristics alone/or by all possible combinations, e.g., an XRPD pattern having peaks at 8.6, 9.3, 10.3, 16.9 and 18.3 degrees 2-theta±0.2 degrees 2-theta; an XRPD pattern as depicted in FIG. 21, and combinations thereof.

Figure 22:
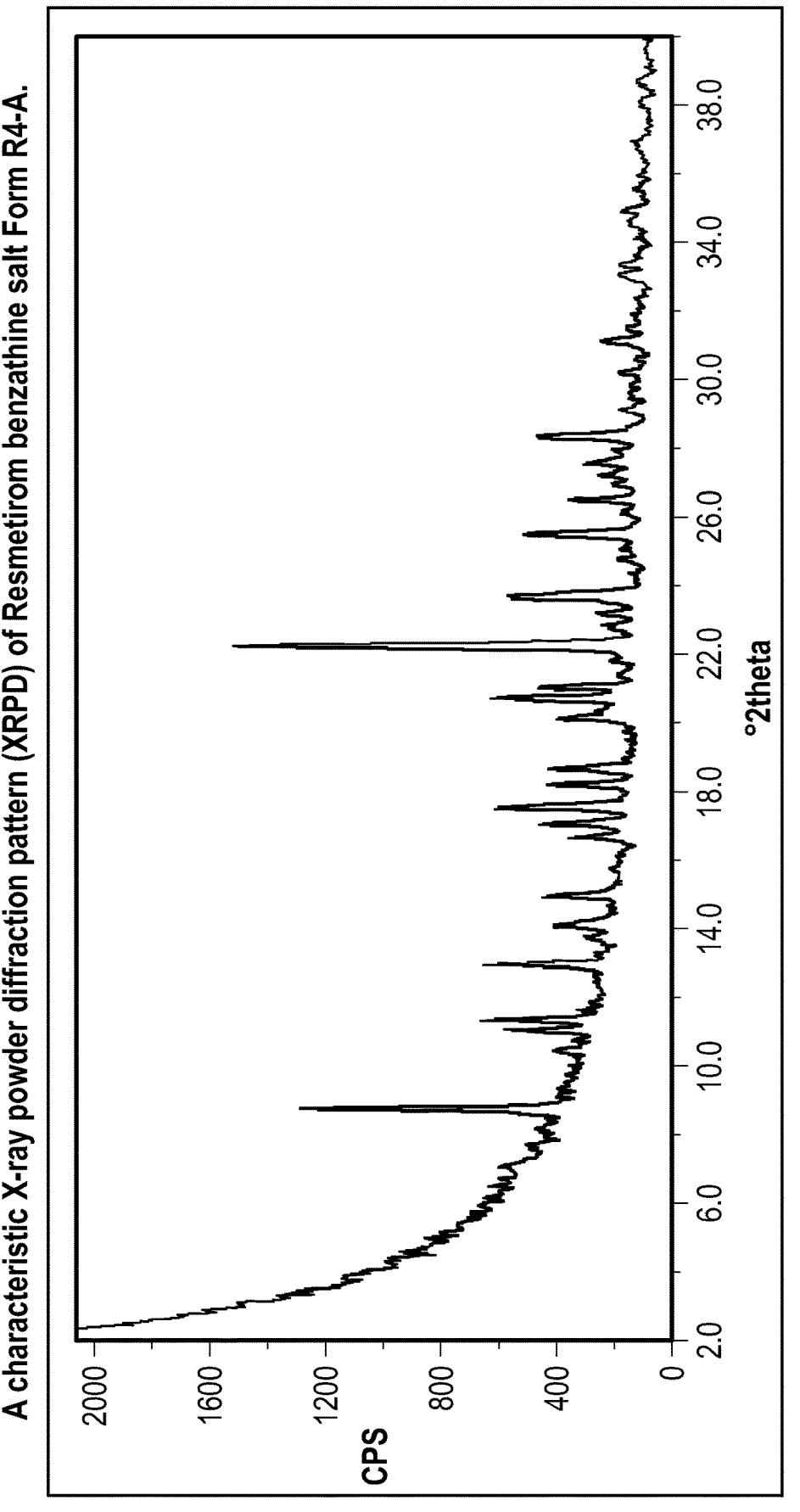
FIG. 22 shows a characteristic X-ray powder diffraction pattern (XRPD) of Resmetirom benzathine salt Form R4-A.

The present disclosure includes a crystalline polymorph Resmetirom benzathine salt designated Form R4-A. The crystalline Form R4-A of Resmetirom benzathine salt may be characterized by data selected from one or more of the following: an X-ray powder diffraction pattern substantially as depicted in FIG. 22; an X-ray powder diffraction pattern having peaks at 8.8, 13.0, 17.6, 20.7, 22.3 degrees 2-theta±0.2 degrees 2-theta; and combinations of these data.

Crystalline Form R4-A of Resmetirom benzathine salt may be further characterized by an X-ray powder diffraction pattern having peaks at 8.8, 13.0, 17.6, 20.7, 22.3 degrees 2-theta±0.2 degrees 2-theta, and also having any one, two, three, four or five additional peaks selected from 11.1, 11.4, 17.1, 18.7 and 23.7 degrees 2-theta±0.2 degrees 2-theta.

Crystalline form R4-A of Resmetirom benzathine salt may be alternatively characterized by an X-ray powder diffraction pattern having peaks at 8.8, 11.1, 11.4, 13.0, 17.1, 17.6, 18.7, 20.7, 22.3 and 23.7 degrees 2-theta±0.2 degrees 2-theta.

In one embodiment of the present disclosure, crystalline Form R4-A of Resmetirom benzathine salt is isolated.

Crystalline Form R4-A of Resmetirom benzathine salt may be characterized by each of the above characteristics alone/or by all possible combinations, e.g., an XRPD pattern having peaks at 8.8, 13.0, 17.6, 20.7, 22.3 degrees 2-theta±0.2 degrees 2-theta; an XRPD pattern as depicted in FIG. 22, and combinations thereof.

The present disclosure relates to Resmetirom:nicotinamide. The Resmetirom:nicotinamide may be a cocrystal.

The present disclosure includes a crystalline polymorph of Resmetirom:nicotinamide co-crystal, designated RC1-A. In any embodiment the molar ratio of nicotinamide and Resmetirom is typically about 1:1.

Figure 23:
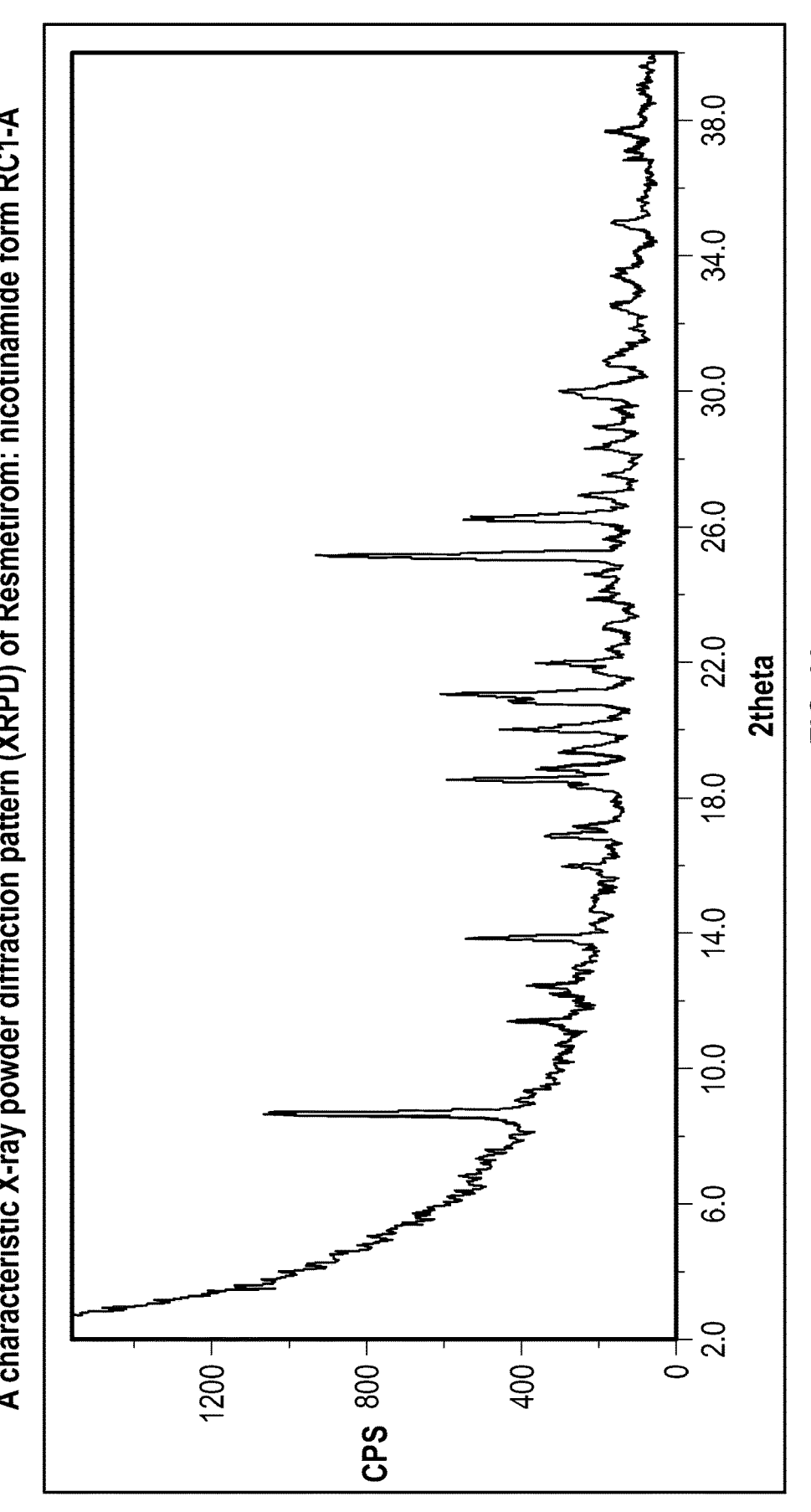
FIG. 23 shows a characteristic X-ray powder diffraction pattern (XRPD) of Resmetirom:nicotinamide Form RC1-A.
Figure 31:
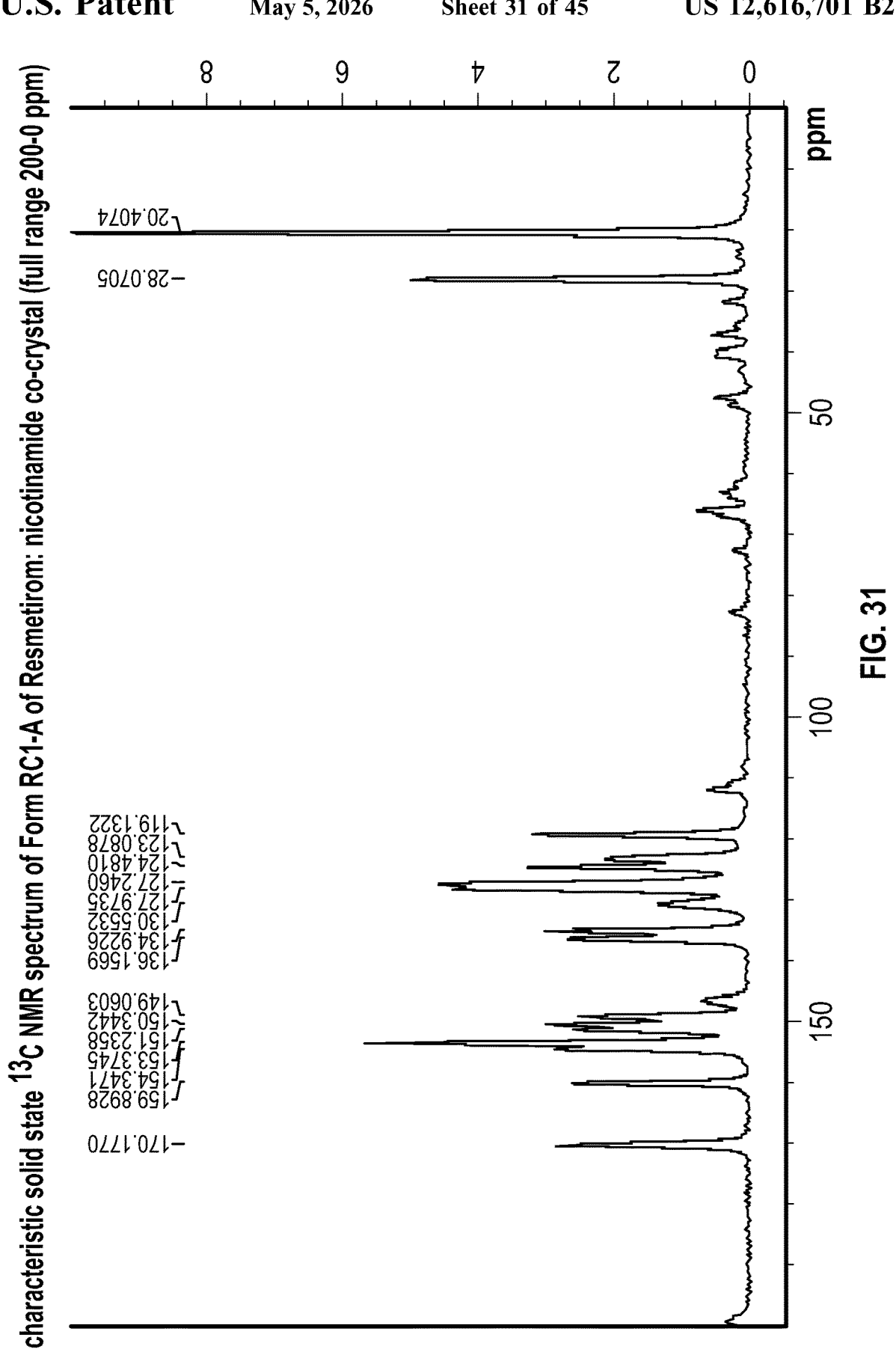
FIG. 31 shows a characteristic solid state $^{13}$C NMR spectrum of Form RC1-A of Resmetirom:nicotinamide co-crystal (full range 200-0 ppm).
Figure 32:
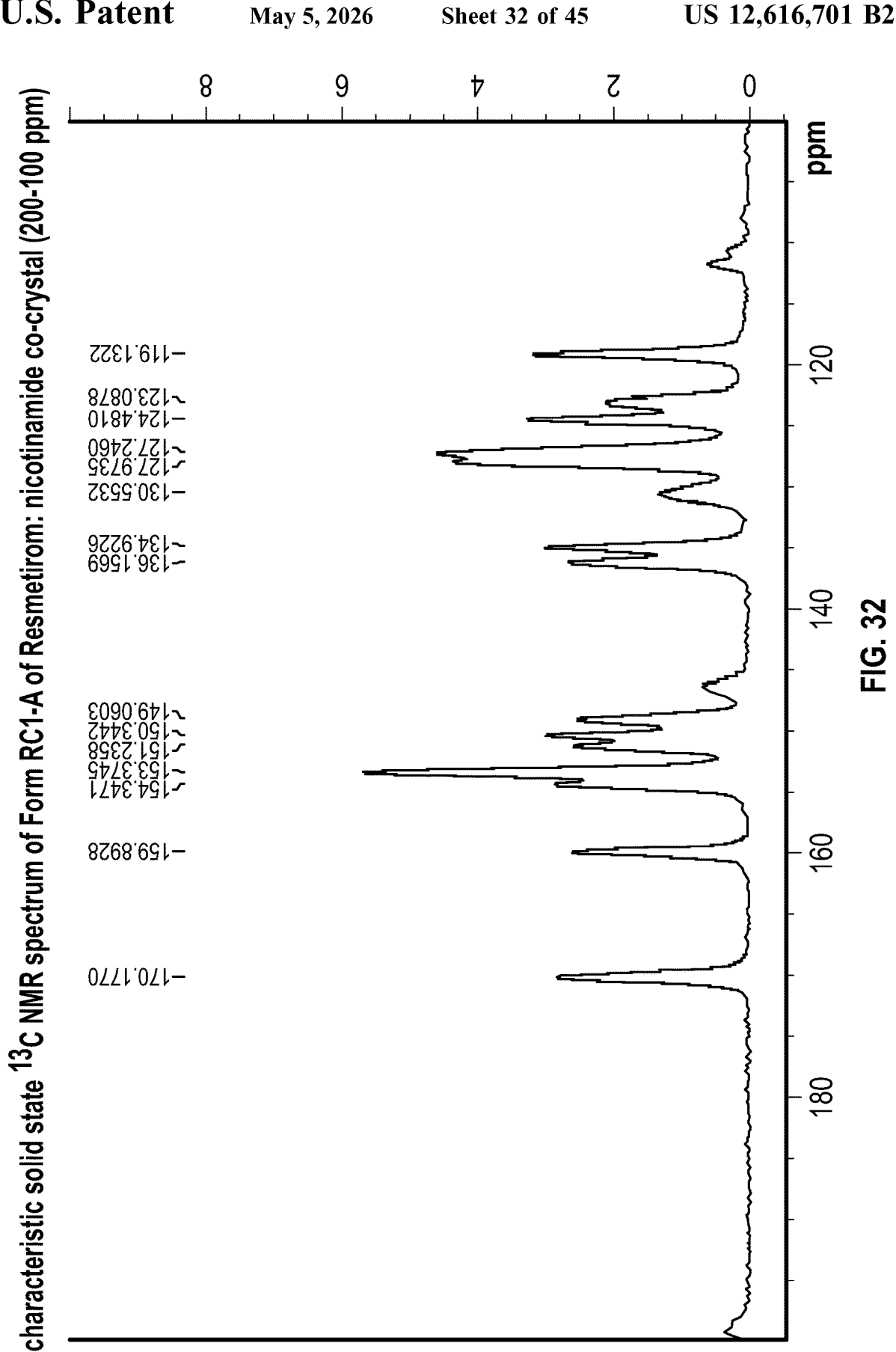
FIG. 32 shows a characteristic solid state $^{13}$C NMR spectrum of Form RC1-A of Resmetirom:nicotinamide co-crystal (200-100 ppm).
Figure 33:
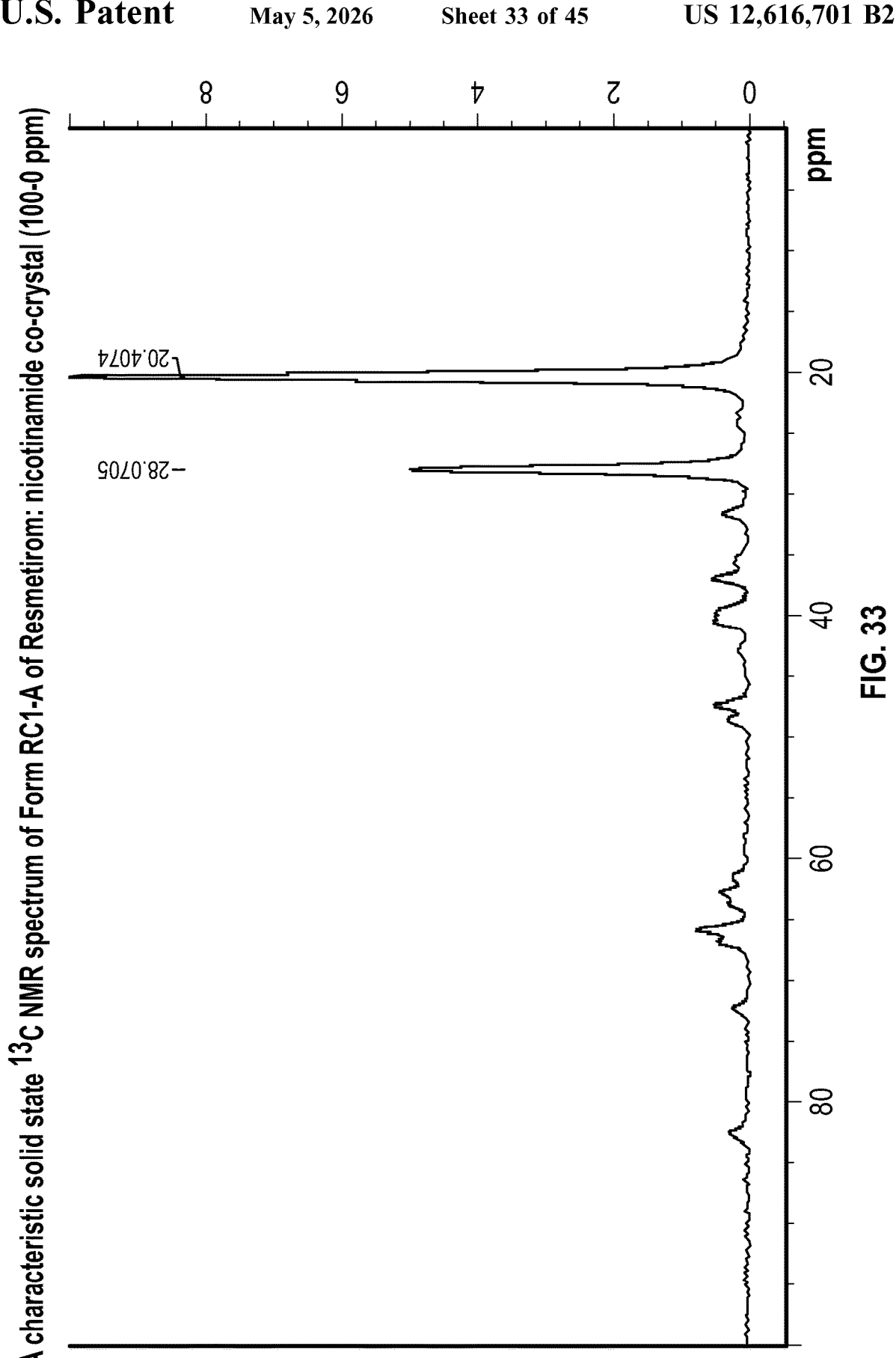
FIG. 33 shows a characteristic solid state $^{13}$C NMR spectrum of Form RC1-A of Resmetirom:nicotinamide co-crystal (100-0 ppm).

The crystalline Form RC1-A of Resmetirom:nicotinamide may be characterized by data selected from one or more of the following: an X-ray powder diffraction pattern substantially as depicted in FIG. 23; an X-ray powder diffraction pattern having peaks at 8.7, 18.6, 21.1, 25.3 and 26.4 degrees 2-theta±0.2 degrees 2-theta; a solid state $^{13}$C NMR spectrum with characteristic peaks at 159.9, 153.4, 136.2, 134.9 and 119.1 ppm±0.2 ppm; a solid state 13C NMR spectrum having the following chemical shift absolute differences from reference peak at 170.2 ppm±1 ppm: 10.3, 16.8, 34.0, 35.3 and 51.0 ppm±0.1 ppm; a solid state $^{13}$C NMR spectrum substantially as depicted in FIG. 31, 32 or 33; and combinations of these data.

Crystalline Form RC1-A of Resmetirom:nicotinamide may be further characterized by an X-ray powder diffraction pattern having peaks at 8.7, 18.6, 21.1, 25.3 and 26.4 degrees 2-theta±0.2 degrees 2-theta, and also having any one, two, three, four or five additional peaks selected from 11.5, 12.6, 13.9, 20.1 and 22.0 degrees 2-theta±0.2 degrees 2-theta.

Crystalline form RC1-A of Resmetirom:nicotinamide co-crystal may be alternatively characterized by an X-ray powder diffraction pattern having peaks at 8.7, 11.5, 12.6, 13.9, 18.6, 20.1, 21.1, 22.0, 25.3 and 26.4 degrees 2-theta±0.2 degrees 2-theta.

In one embodiment of the present disclosure, crystalline Form RC1-A of Resmetirom:nicotinamide is isolated. Particularly, crystalline form RC1-A of Resmetirom:nicotinamide co-crystal according to any aspect or embodiment of the disclosure may be isolated.

Crystalline Form RC1-A of Resmetirom:nicotinamide co crystal according to any aspect or embodiment of the disclosure may be anhydrous.

In any aspect or embodiment of the present disclosure, crystalline RC1-A of Resmetirom:nicotinamide co crystal is non-hygroscopic. Particularly, Form RC1-A of Resmetirom: nicotinamide co crystal according to any aspect or embodiment is polymorphically stable at up to 80% relative humidity at room temperature for at least 7 days.

Crystalline Form RC1-A of Resmetirom:nicotinamide may be characterized by each of the above characteristics alone or by all possible combinations, e.g., an XRPD pattern having peaks at 8.7, 18.6, 21.1, 25.3 and 26.4 degrees 2-theta±0.2 degrees 2-theta; an XRPD pattern as depicted in FIG. 23, and combinations thereof.

The present disclosure relates to Resmetirom:caffeine co crystal.

The present disclosure includes a crystalline polymorph of Resmetirom:caffeine co-crystal, designated RC2-A. In any embodiment the molar ratio of caffeine and Resmetirom in form RC2-A is typically about 1:1.

Figure 24:
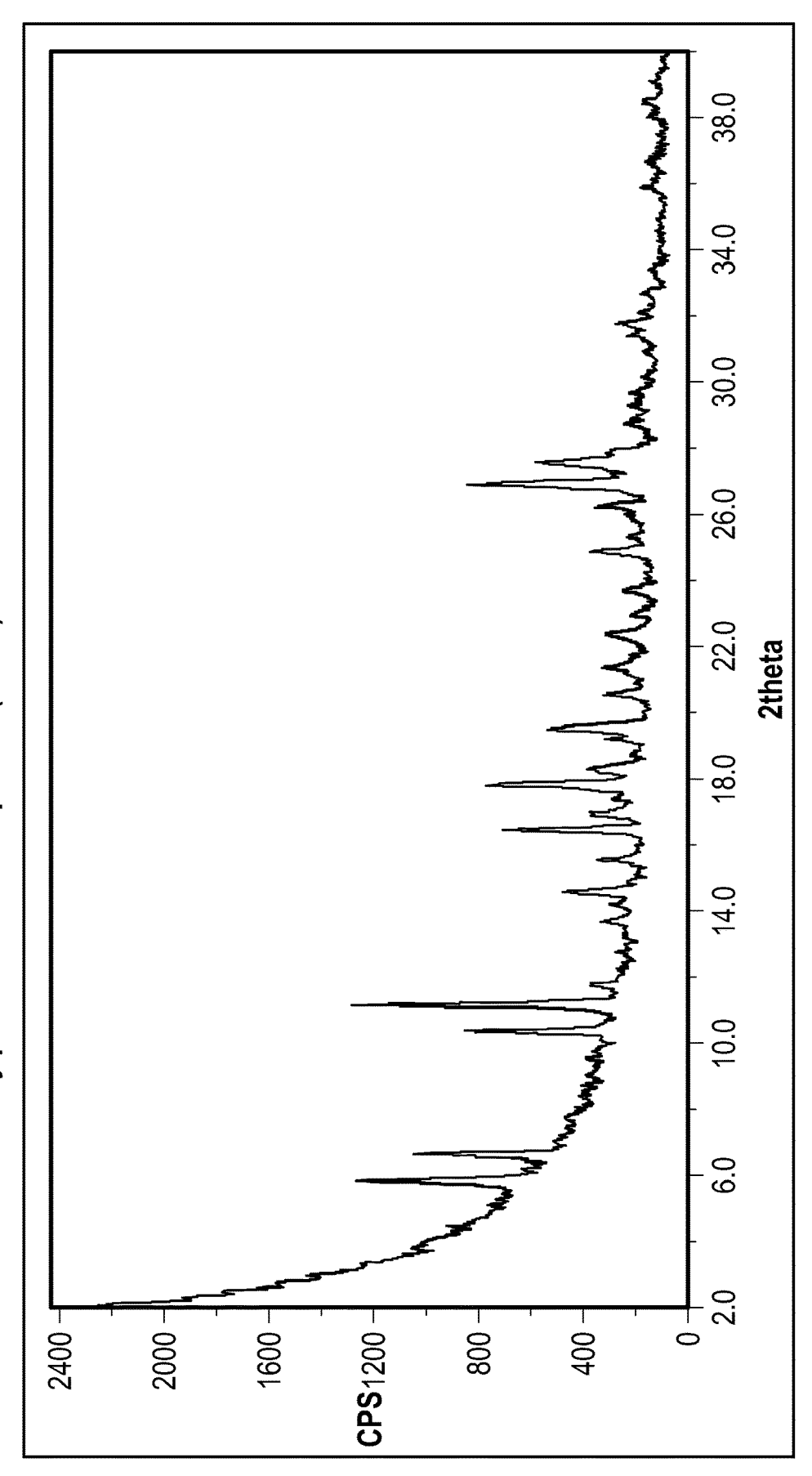
FIG. 24 shows a characteristic X-ray powder diffraction pattern (XRPD) of Resmetirom:caffeine Form RC2-A.
Figure 34:
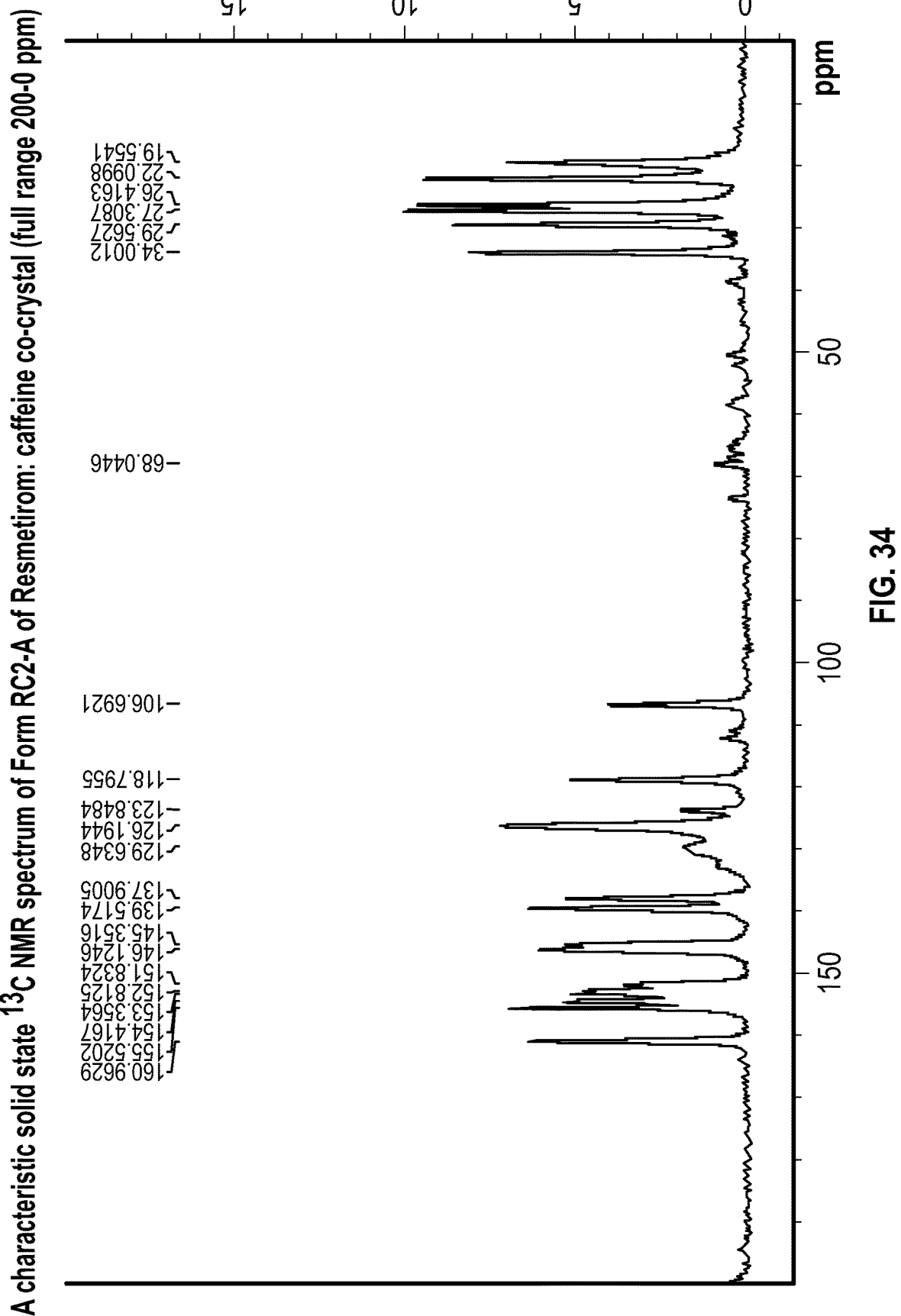
FIG. 34 shows a characteristic solid state $^{13}$C NMR spectrum of Form RC2-A of Resmetirom:caffeine co-crystal (full range 200-0 ppm).
Figure 35:
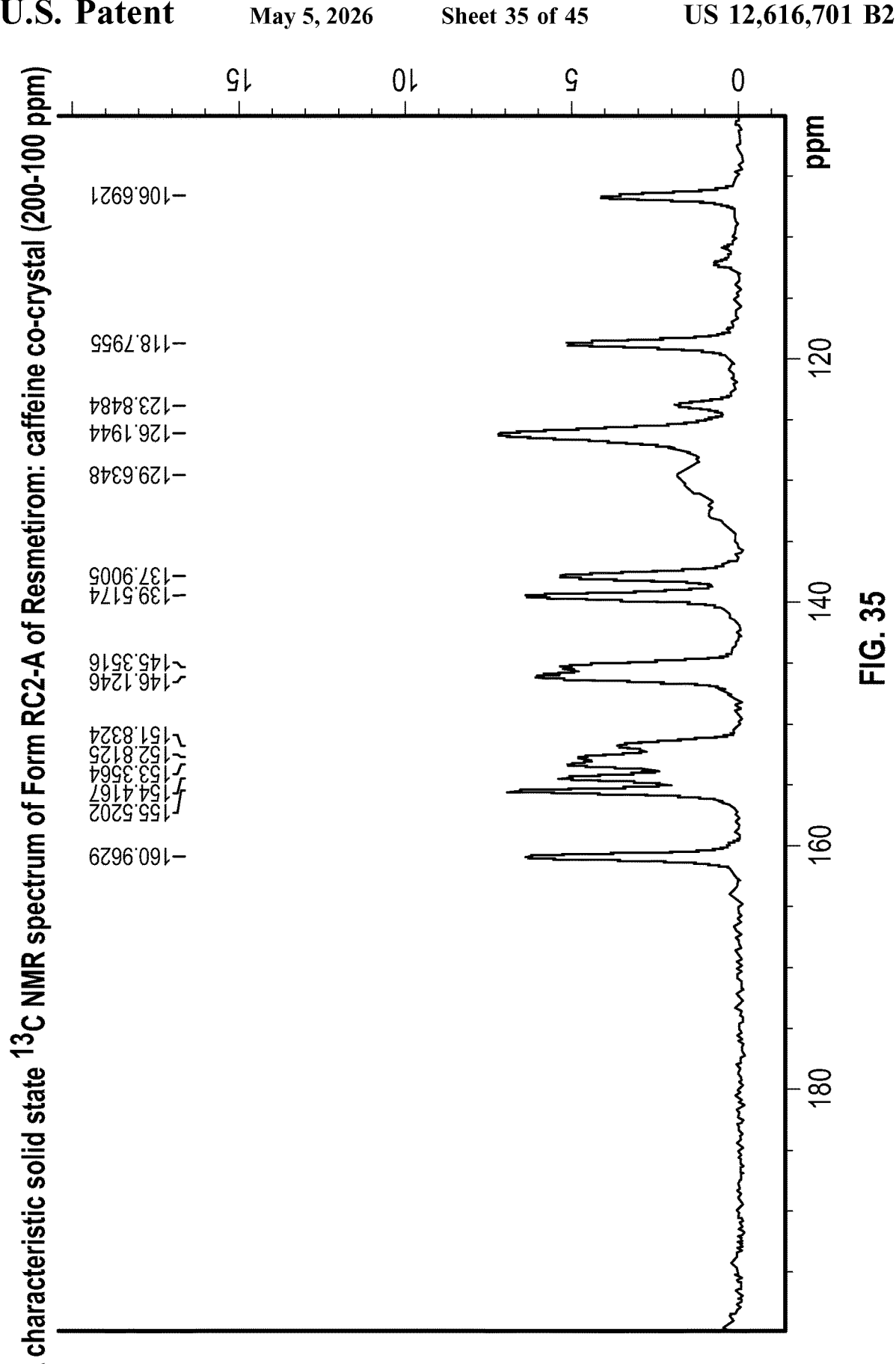
FIG. 35 shows a characteristic solid state $^{13}$C NMR spectrum of Form RC2-A of Resmetirom:caffeine co-crystal (200-100 ppm).
Figure 36:
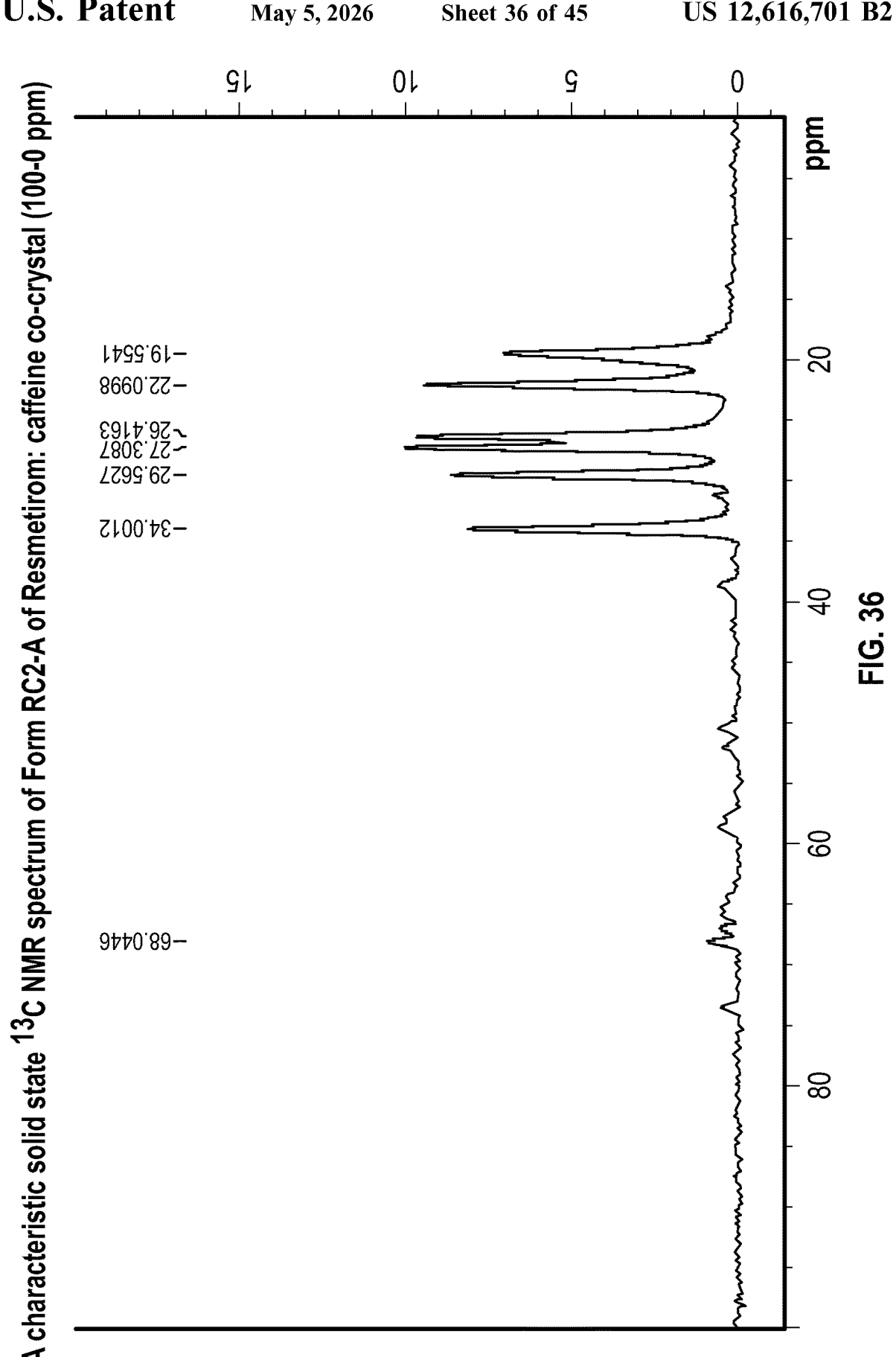
FIG. 36 shows a characteristic solid state $^{13}$C NMR spectrum of Form RC2-A of Resmetirom:caffeine co-crystal (100-0 ppm).

The crystalline Form RC2-A of Resmetirom:caffeine may be characterized by data selected from one or more of the following: an X-ray powder diffraction pattern substantially as depicted in FIG. 24; an X-ray powder diffraction pattern having peaks at 6.0, 6.8, 10.4, 11.2 and 16.4 degrees 2-theta±0.2 degrees 2-theta; a solid state $^{13}$C NMR spectrum with characteristic peaks at 139.5, 118.8, 106.7, 34.0 and 29.6 ppm±0.2 ppm; a solid state $^{13}$C NMR spectrum having the following chemical shift absolute differences from reference peak at 161.0 ppm±1 ppm: 21.4, 42.2, 54.3, 127.0 and 131.4 ppm±0.1 ppm; a solid state $^{13}$C NMR spectrum substantially as depicted in FIG. 34, 35 or 36; and combinations of these data.

Crystalline Form RC2-A of Resmetirom:caffeine may be further characterized by an X-ray powder diffraction pattern having peaks at 6.0, 6.8, 10.4, 11.2 and 16.4 degrees 2-theta±0.2 degrees 2-theta, and also having any one, two, three, four or five additional peaks selected from 14.6, 15.6, 17.8, 19.5 and 26.9 degrees 2-theta±0.2 degrees 2-theta.

Crystalline form RC2-A of Resmetirom:caffeine co-crystal may be alternatively characterized by an X-ray powder diffraction pattern having peaks at 6.0, 6.8, 10.4, 11.2, 14.6, 15.6, 16.4, 17.8, 19.5 and 26.9 degrees 2-theta±0.2 degrees 2-theta.

In one embodiment of the present disclosure, crystalline Form RC2-A of Resmetirom:caffeine is isolated. Particularly, crystalline form RC2-A of Resmetirom:caffeine co-crystal according to any aspect or embodiment of the disclosure may be isolated.

Crystalline Form RC2-A of Resmetirom:caffeine co-crystal according to any aspect or embodiment of the disclosure may be anhydrous.

In any aspect or embodiment of the present disclosure, crystalline RC2-A of Resmetirom:caffeine co crystal is non-hygroscopic. Particularly, Form RC2-A of Resmetirom: caffeine co crystal according to any aspect or embodiment is polymorphically stable at up to 100% relative humidity at room temperature for at least 7 days.

Crystalline Form RC2-A of Resmetirom:caffeine may be characterized by each of the above characteristics alone or by all possible combinations, e.g., an XRPD pattern having peaks at 6.0, 6.8, 10.4, 11.2 and 16.4 degrees 2-theta±0.2 degrees 2-theta; an XRPD pattern as depicted in FIG. 24, and combinations thereof.

The present disclosure includes a crystalline polymorph of Resmetirom:caffeine co-crystal, designated RC2-B. In any embodiment the molar ratio of caffeine and Resmetirom in form RC2-B is typically about 1:1.

Figure 25:
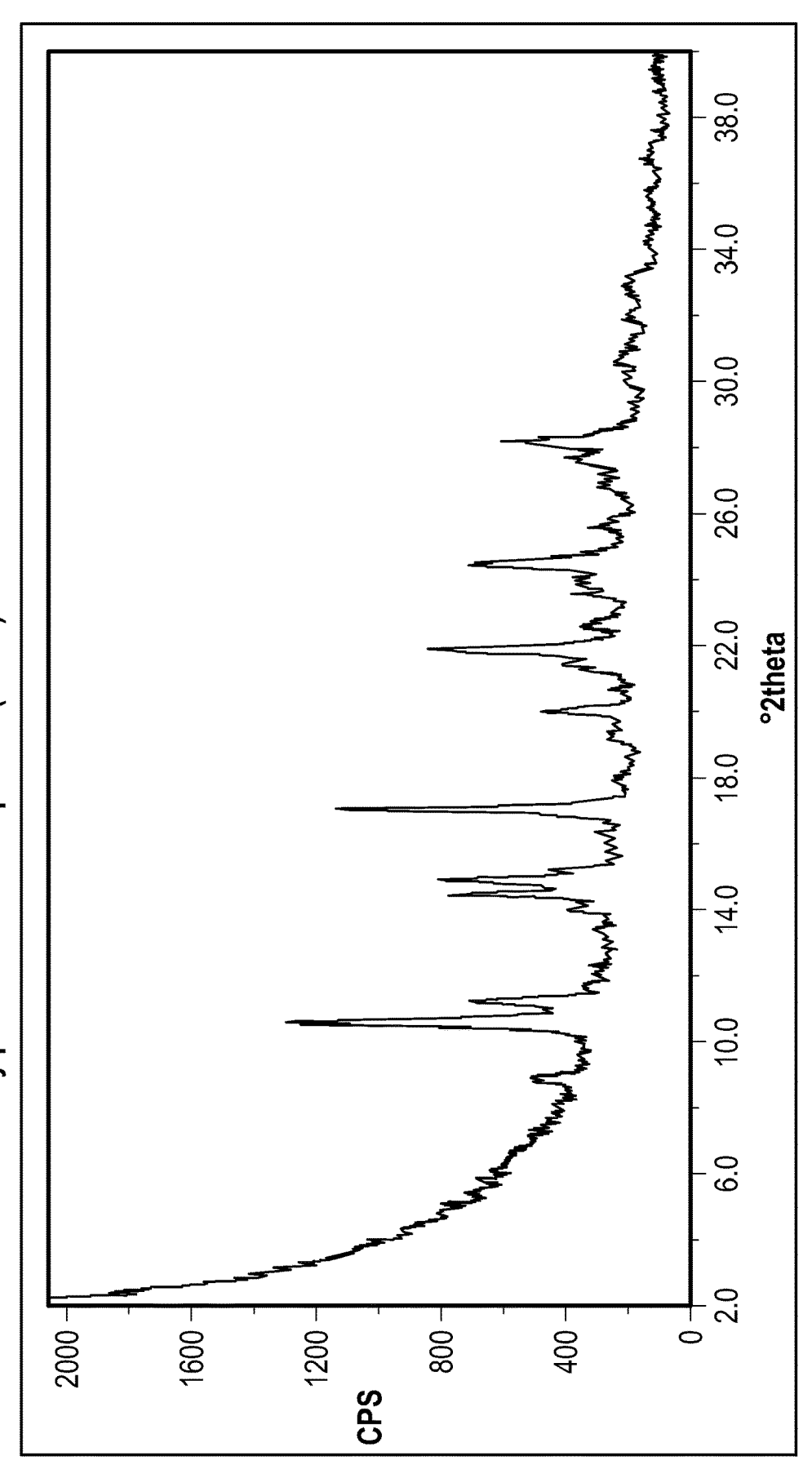
FIG. 25 shows a characteristic X-ray powder diffraction pattern (XRPD) of Resmetirom:caffeine Form RC2-B.
Figure 37:
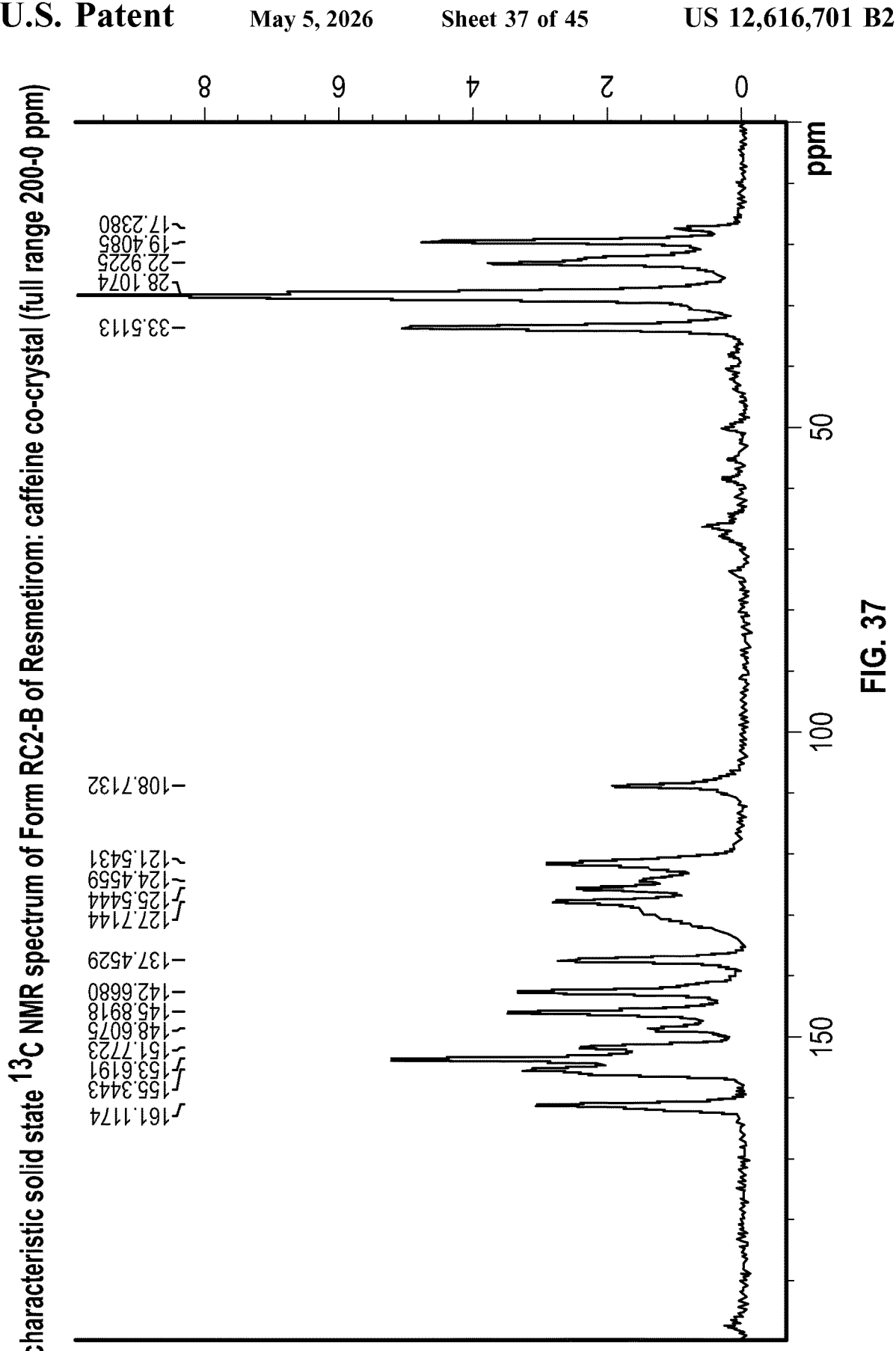
FIG. 37 shows a characteristic solid state $^{13}$C NMR spectrum of Form RC2-B of Resmetirom:caffeine co-crystal (full range 200-0 ppm).
Figure 38:
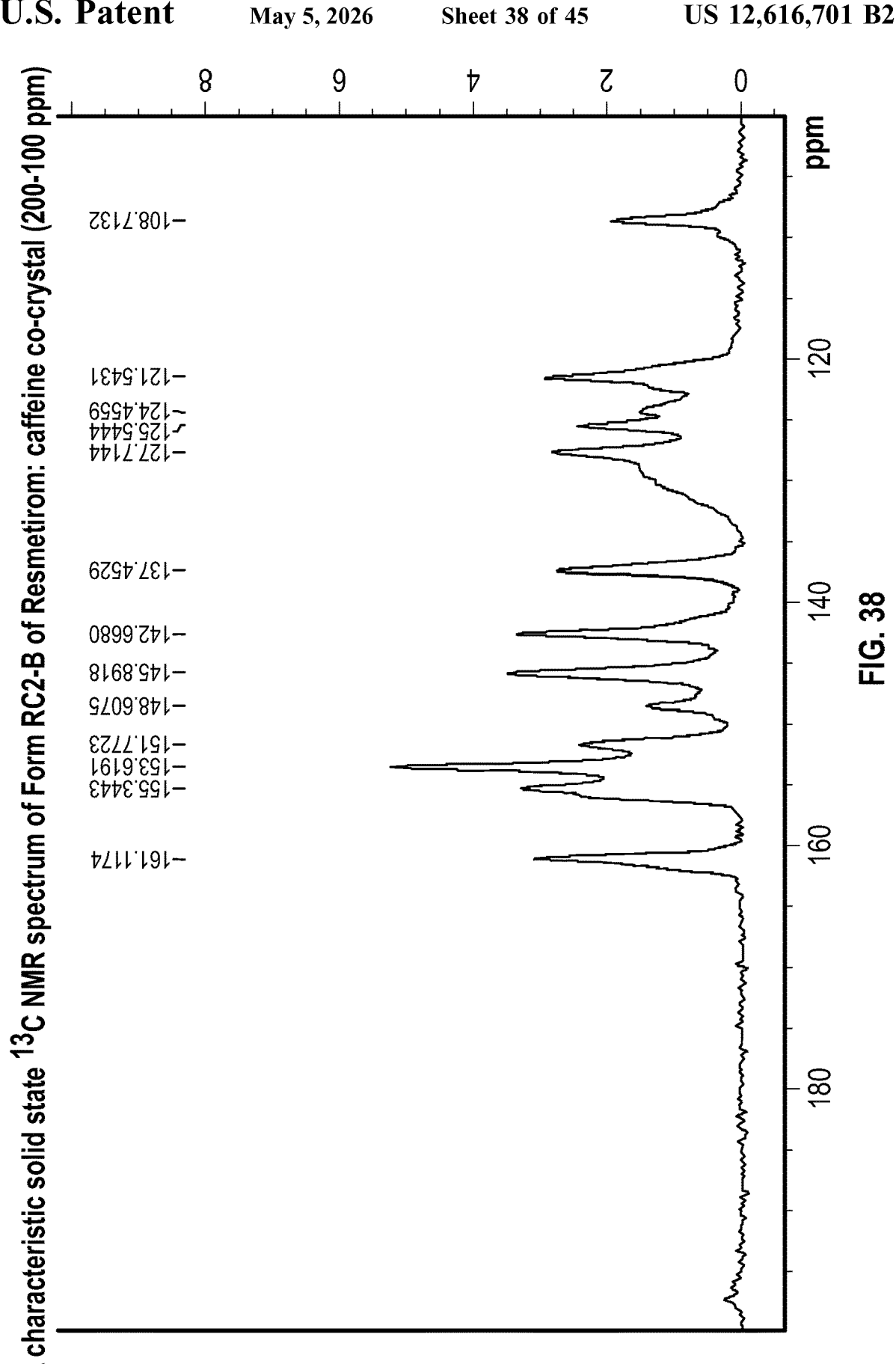
FIG. 38 shows a characteristic solid state $^{13}$C NMR spectrum of Form RC2-B of Resmetirom:caffeine co-crystal (200-100 ppm).
Figure 39:
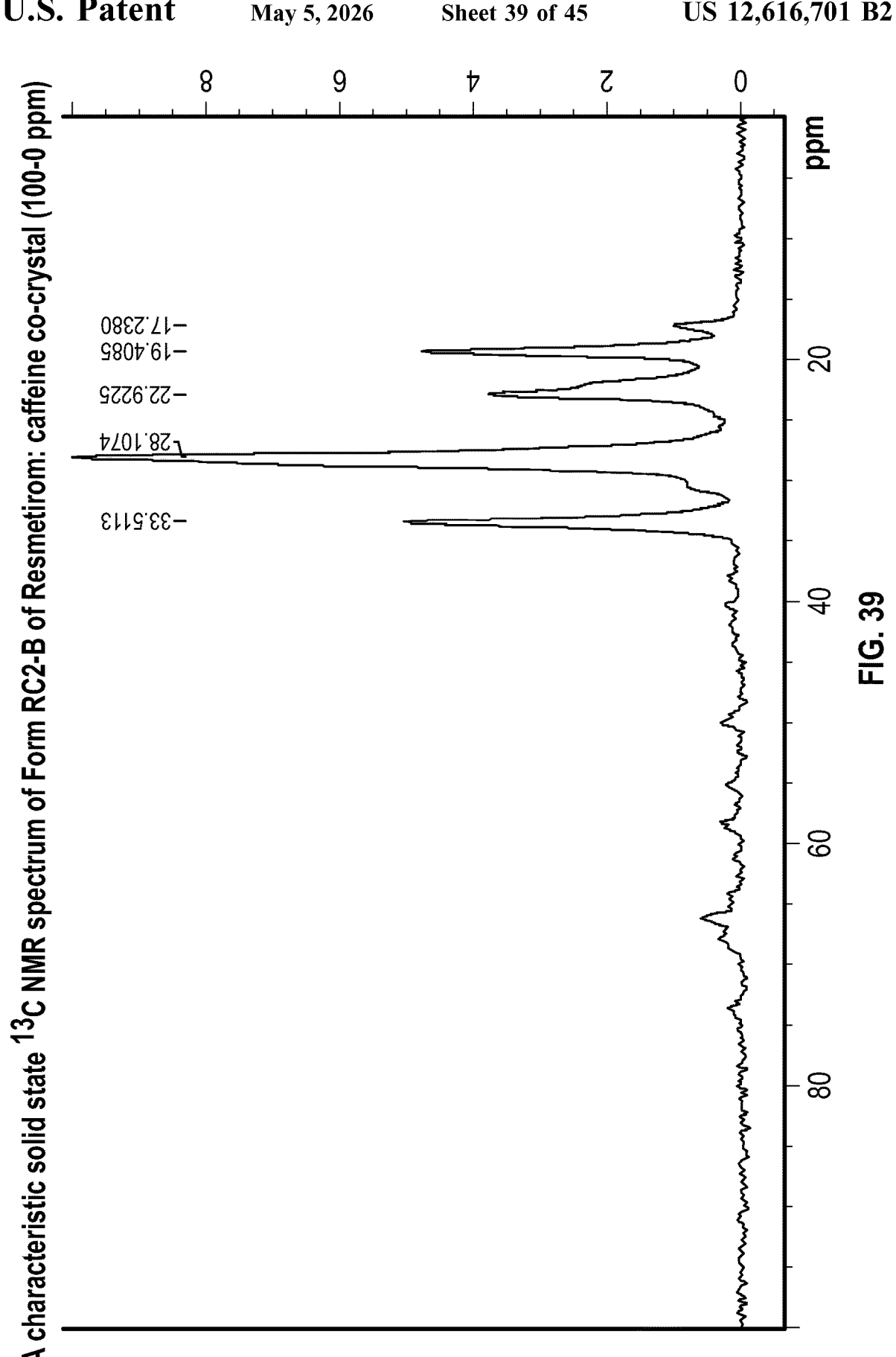
FIG. 39 shows a characteristic solid state $^{13}$C NMR spectrum of Form RC2-B of Resmetirom:caffeine co-crystal (100-0 ppm).

The crystalline Form RC2-B of Resmetirom:caffeine may be characterized by data selected from one or more of the following: an X-ray powder diffraction pattern substantially as depicted in FIG. 25; an X-ray powder diffraction pattern having peaks at 8.9, 10.6, 11.2, 14.5 and 17.1 degrees 2-theta±0.2 degrees 2-theta; a solid state $^{13}$C NMR spectrum with characteristic peaks at 145.9, 142.7, 108.7, 33.5 and 28.1 ppm±0.2 ppm; a solid state $^{13}$C NMR spectrum having the following chemical shift absolute differences from reference peak at 161.1 ppm±1 ppm: 15.2, 18.45, 52.4, 127.6 and 133.0 ppm±0.1 ppm; a solid state $^{13}$C NMR spectrum substantially as depicted in FIG. 37, 38 or 39; and combinations of these data.

Crystalline Form RC2-B of Resmetirom:caffeine may be further characterized by an X-ray powder diffraction pattern having peaks at 8.9, 10.6, 11.2, 14.5 and 17.1 degrees 2-theta±0.2 degrees 2-theta, and also having any one, two, three, four or five additional peaks selected from 14.9, 20.0, 21.9, 24.5 and 28.2 degrees 2-theta±0.2 degrees 2-theta.

Crystalline form RC2-B of Resmetirom:caffeine co-crystal may be alternatively characterized by an X-ray powder diffraction pattern having peaks at 8.9, 10.6, 11.2, 14.5, 14.9, 17.1, 20.0, 21.9, 24.5 and 28.2 degrees 2-theta±0.2 degrees 2-theta.

In one embodiment of the present disclosure, crystalline Form RC2-B of Resmetirom:caffeine co-crystal is isolated. Particularly, crystalline form RC2-B of Resmetirom:caffeine co-crystal according to any aspect or embodiment of the disclosure may be isolated. Crystalline Form RC2-B of Resmetirom:caffeine co-crystal according to any aspect or embodiment of the disclosure may be anhydrous.

In any aspect or embodiment of the present disclosure, crystalline RC2-B of Resmetirom:caffeine co crystal is non-hygroscopic. Particularly, Form RC2-B of Resmetirom: caffeine co crystal according to any aspect or embodiment is polymorphically stable at up to 80% relative humidity at room temperature for at least 7 days.

Crystalline Form RC2-B of Resmetirom:caffeine may be characterized by each of the above characteristics alone or by all possible combinations, e.g., an XRPD pattern having peaks at 8.9, 10.6, 11.2, 14.5 and 17.1 degrees 2-theta±0.2 degrees 2-theta; an XRPD pattern as depicted in FIG. 25, and combinations thereof.

The present disclosure includes a crystalline polymorph of Resmetirom: 2-picolinic acid, designated RC3-A. In any aspect or embodiment of the disclosure, Resmetirom: 2-picolinic acid Form RC3-A may be Resmetirom 2-picolinic acid salt, optionally, wherein the molar ratio of Resmetirom to 2-picolinic acid is about 1:1. Preferably, in any aspect or embodiment of the disclosure, the Resmetirom: 2-picolinic acid Form RC3-A may be a cocrystal of Resmetirom with 2-picolinic acid, optionally wherein the molar ratio of 2-picolinic acid to Resmetirom in form RC3-A is typically about 1:1.

Figure 26:
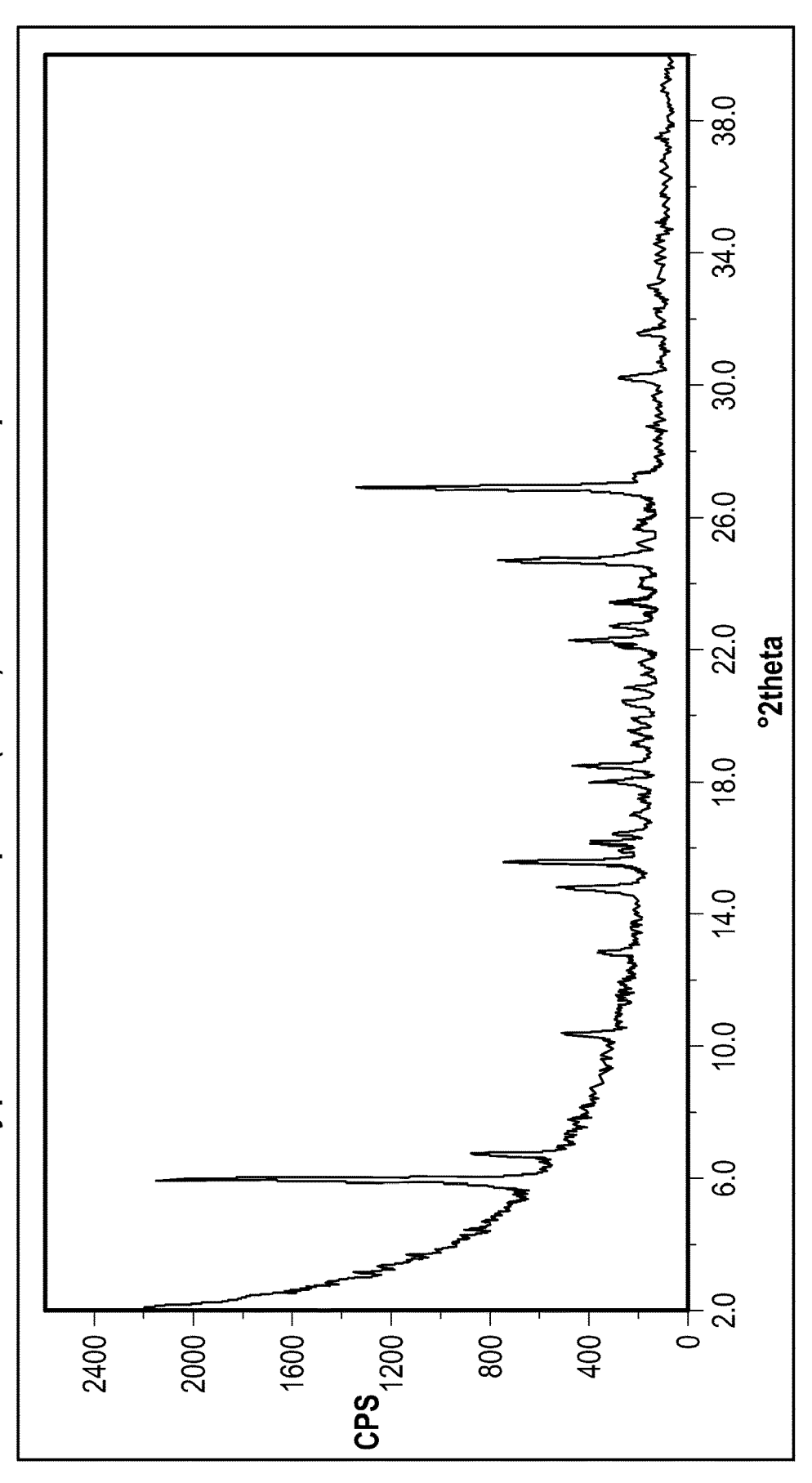
FIG. 26 shows a characteristic X-ray powder diffraction pattern (XRPD) of Resmetirom: 2-picolinic acid Form RC3-A.

The crystalline Form RC3-A of Resmetirom: 2-picolinic acid may be characterized by data selected from one or more of the following: an X-ray powder diffraction pattern substantially as depicted in FIG. 26; an X-ray powder diffraction pattern having peaks at 6.0, 6.8, 12.9, 15.6 and 26.9 degrees 2-theta±0.2 degrees 2-theta; and combinations of these data.

Crystalline Form RC3-A of Resmetirom: 2-picolinic acid may be further characterized by an X-ray powder diffraction pattern having peaks at 6.0, 6.8, 12.9, 15.6 and 26.9 degrees 2-theta±0.2 degrees 2-theta, and also having any one, two, three, four or five additional peaks selected from 10.4, 14.8, 18.0, 18.5 and 24.7 degrees 2-theta±0.2 degrees 2-theta.

In one embodiment of the present disclosure, crystalline Form RC3-A of Resmetirom: 2-picolinic acid is isolated.

Crystalline Form RC3-A of Resmetirom: 2-picolinic acid may be anhydrous.

Crystalline Form RC3-A of Resmetirom: 2-picolinic acid may be characterized by each of the above characteristics alone or by all possible combinations, e.g., an XRPD pattern having peaks at 6.0, 6.8, 12.9, 15.6 and 26.9 degrees 2-theta±0.2 degrees 2-theta; an XRPD pattern as depicted in FIG. 26, and combinations thereof.

Figure 27:
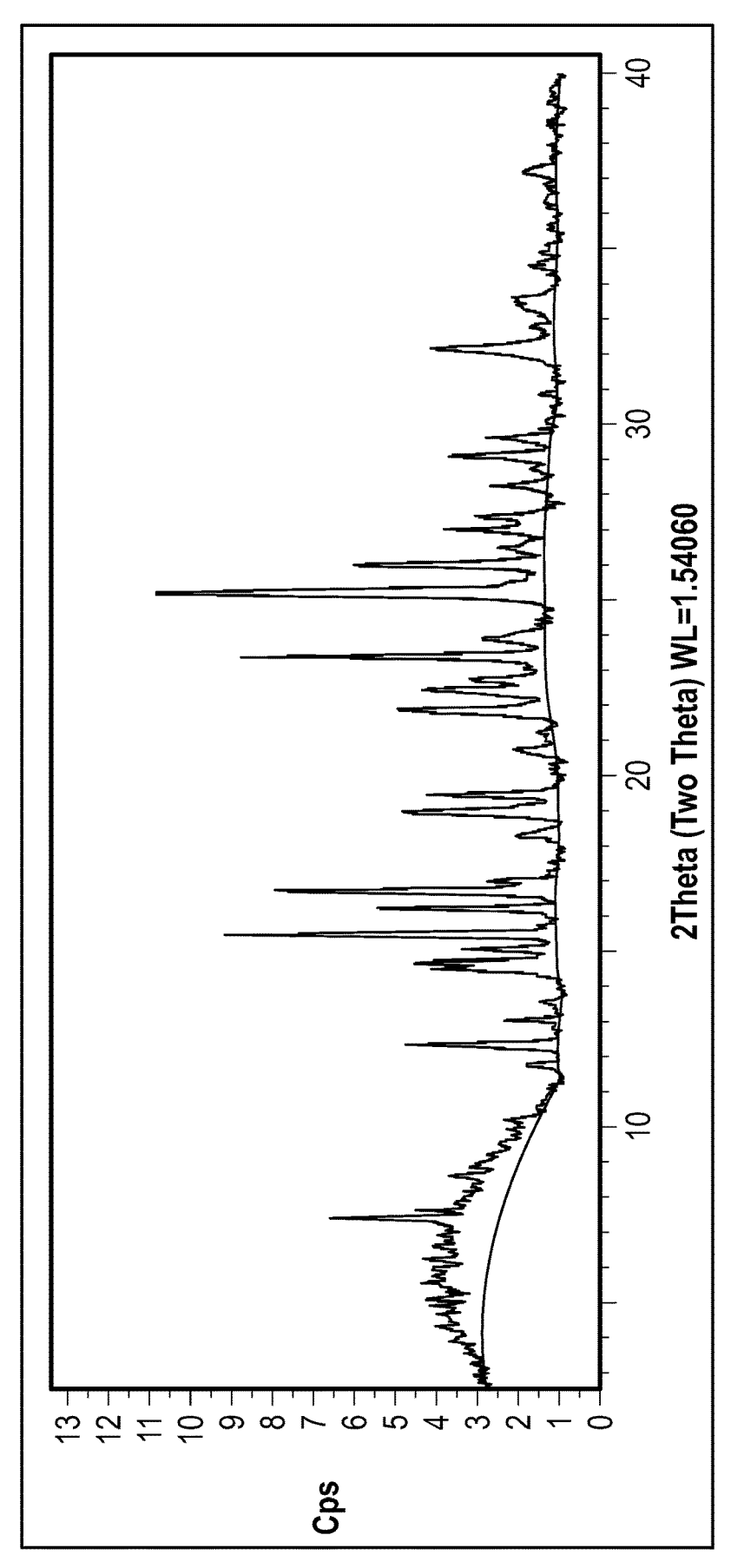
FIG. 27 shows a characteristic X-ray powder diffraction pattern (XRPD) of Resmetirom:Urea form RC4-A.

The present disclosure includes a crystalline polymorph of Resmetirom:Urea, designated RC4-A. The crystalline Form RC4-A of Resmetirom:Urea may be characterized by data selected from one or more of the following: an X-ray powder diffraction pattern substantially as depicted in FIG. 27; an X-ray powder diffraction pattern having peaks at 7.6, 12.6, 15.7, 16.4 and 16.9 degrees 2-theta±0.2 degrees 2-theta; and combinations of these data.

Crystalline Form RC4-A of Resmetirom:Urea may be further characterized by an X-ray powder diffraction pattern having peaks at 7.6, 12.6, 15.7, 16.4 and 16.9 degrees 2-theta±0.2 degrees 2-theta, and also having any one, two, three, four or five additional peaks selected from 15.2, 19.1, 19.6, 22.0 and 23.6 degrees 2-theta±0.2 degrees 2-theta.

In one embodiment of the present disclosure, crystalline Form RC4-A of Resmetirom: 2-picolinic acid is isolated.

Crystalline Form RC4-A of Resmetirom:Urea may be anhydrous.

In any aspect or embodiment of the disclosure, Resmetirom:Urea Form RC4-A may be Resmetirom:Urea salt, optionally, wherein the molar ratio of Resmetirom to Urea is about 1:1. Preferably, in any aspect or embodiment of the disclosure, the Resmetirom:Urea Form RC4-A may be a cocrystal of Resmetirom with Urea, optionally wherein the molar ratio of Urea to Resmetirom in form RC4-A is typically about 1:1.

Crystalline Form RC4-A of Resmetirom:Urea may be characterized by each of the above characteristics alone or by all possible combinations, e.g., an XRPD pattern having peaks at 7.6, 12.6, 15.7, 16.4 and 16.9 degrees 2-theta±0.2 degrees 2-theta; an XRPD pattern as depicted in FIG. 27, and combinations thereof.

In any aspect or embodiment of the present disclosure, any of the solid state forms of Resmetirom, Resmetirom salts or Resmetirom cocrystals, described herein may be polymorphically pure or may be substantially free of any other solid state forms of the subject Resmetirom, Resmetirom salts or Resmetirom cocrystals, respectively (for example a crystalline form of a Resmetirom salt which is polymorphically pure, may be substantially free of any other solid state forms of the Resmetirom salt; a crystalline form of Resmetirom which is polymorphically pure, may be substantially free of any other solid state forms of the Resmetirom; and likewise, a crystalline form of a Resmetirom cocrystal which is polymorphically pure, may be substantially free of any other solid state forms of the Resmetirom cocrystal). In any aspect or embodiment of the present disclosure, any of the solid state forms of Resmetirom, Resmetirom salts or Resmetirom cocrystals described in any aspect or embodiment disclosed herein, may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of the subject compound (i.e. Resmetirom, Resmetirom salts or Resmetirom cocrystals, respectively), preferably as measured by XRPD. Thus, any of the disclosed crystalline forms of Resmetirom, Resmetirom salts or Resmetirom cocrystals, described herein may be substantially free of any other solid state forms of the subject Resmetirom, Resmetirom salts or Resmetirom cocrystals respectively, and may contain greater than about 80% (w/w), greater than about 90% (w/w), greater than about 95% (w/w), greater than about 98% (w/w), greater than about 99% (w/w), or about 100% of the subject solid state form of the Resmetirom, Resmetirom salts or Resmetirom cocrystals respectively.

The above crystalline polymorphs can be used to prepare other crystalline polymorphs of Resmetirom, Resmetirom salts and their solid state forms.

The present disclosure encompasses a process for preparing other solid state forms of Resmetirom, Resmetirom salts and their solid state forms thereof. The process includes preparing any one of the solid state forms of Resmetirom or of the salts thereof or of the Resmetirom co-crystals thereof, by the processes of the present disclosure, and converting that form or salt to a different form of Resmetirom or another salt. The conversion of one salt to another salt can be done, for example, by a process including acidifying any one or a combination of the above described salts such as Resmetirom N-methylmorpholine, Resmetirom piperazine, Resmetirom benzathine and/or solid state forms thereof, and reacting the obtained Resmetirom base with an appropriate base, to obtain the corresponding salt. Alternatively, the conversion can be done by salt switching, i.e., reacting a Resmetirom base addition salt, with a base having a pKa which is higher than the pKa of the base of the first Resmetirom base addition salt.

The present disclosure encompasses a process for preparing other solid state forms of Resmetirom, Resmetirom salts, co-crystals and solid state forms thereof. The process includes preparing any one of Resmetirom:nicotinamide, Resmetirom:caffeine, Resmetirom: 2-picolinic acid and/or Resmetirom:Urea. or Resmetirom N-methyl-morpholine salt, Resmetirom piperazine salt, Resmetirom benzathine salt, Resmetirom:L-proline, and crystalline forms thereof, of the present disclosure or any one of the solid state forms thereof by the processes of the present disclosure, and converting the said Resmetirom:nicotinamide, Resmetirom: caffeine, Resmetirom: 2-picolinic acid and/or Resmetirom: Urea or forms thereof, or Resmetirom N-methyl-morpholine salt, Resmetirom piperazine salt, Resmetirom benzathine salt, Resmetirom:L-proline, and crystalline forms thereof, to said other Resmetirom base, salt or co-crystal.

The present disclosure provides the above described crystalline polymorphs of Resmetirom or salts thereof or any one of the above described crystalline polymorphs of Resmetirom:nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom:L-proline, and crystalline forms thereof, for use in the preparation of pharmaceutical compositions comprising Resmetirom, Resmetirom salts and/or crystalline polymorphs thereof.

The present disclosure also encompasses the use of crystalline polymorphs of Resmetirom or salts thereof or any one of the above described crystalline polymorphs of Resmetirom:nicotinamide, Resmetirom:caffeine, Resmetirom: 2-picolinic acid and/or Resmetirom:Urea, or Resmetirom N-methyl-morpholine salt, Resmetirom piperazine salt, Resmetirom benzathine salt, Resmetirom:L-proline, and crystalline forms thereof, of the present disclosure for the preparation of pharmaceutical compositions of crystalline polymorph Resmetirom and/or crystalline polymorphs thereof.

The present disclosure further encompasses processes for purification of Resmetirom.

The process may comprise treating a solution of Resmetirom in a solvent comprising methanol, and/or 2-methoxy-ethanol, with active carbon, removing the active carbon and the solvent, to obtain pure Resmetirom.

In embodiments, the present disclosure encompasses a process for purification of Resmetirom wherein the process comprises:

a) providing a solution of Resmetirom in a solvent selected from methanol, 2-methoxy ethanol, or a mixture thereof, optionally at an elevated temperature;
b) adding active carbon;
c) optionally stirring;
d) removing the active carbon by filtration under vacuum;
e) concentrating the solution to obtain pure Resmetirom.

In a particular embodiment the present disclosure encompasses a process for purification of Resmetirom wherein the process comprises:

a) providing a solution of Resmetirom in a solvent selected from methanol, 2-methoxy ethanol, or a mixture thereof, at a temperature of about 70° C. to about 90° C.;
b) adding active carbon to the hot solution;
c) optionally stirring;
d) removing the active carbon by hot filtration under vacuum;
e) concentrating the solution to obtain pure Resmetirom.

Concentration of the solution can be performed by any method known in the art, for example by concentration under reduced pressure or by distillation. The process may comprise further drying steps.

The present disclosure further encompasses processes for preparation of form 14 of Resmetirom.

In one aspect, the process comprises crystallising Resmetirom from a reaction mixture comprising methyl tetrahydrofuran to obtain form 14.

In embodiments, the present disclosure encompasses a process for preparation of form 14 of Resmetirom wherein the process includes:

a) providing a solution or a slurry of Resmetirom in methyl THF, optionally at an elevated temperature;
b) optionally cooling and optionally stirring; and
c) optionally isolating form 14 of Resmetirom.

According to any aspect or embodiment of the process for preparing Form 14 of Resmetirom, the solution or slurry in step (a) may be heated, optionally to a temperature of: about 40° C. to about 95° C. about 50° C. to about 90° C., about 55° C. to about 80° C., or about 60° C. to about 75° C. The heated mixture may be a solution or a slurry.

Optionally when the mixture in step (a) is a solution, the solution may be filtered, preferably at the elevated temperature range. In any embodiment, the solution may be cooled. The cooling may be to a temperature of: about –10° C. to about 20° C., about –5° C. to about 10° C., about 0° C. to about 8° C., or about 2° C. to about 5° C. The mixture may be stirred at this temperature for a suitable period of time. Particularly, the mixture may be stirred for about 4 hours to about 30 hours, about 10 hours to about 25 hours, about 14 hours to about 20 hours, or about 18 hours.

Optionally, when the mixture in step (a) is a slurry, the slurry may be stirred at the elevated temperature for a suitable period of time. Particularly, the mixture may be stirred for about 18 to about 96 hours, about 24 to about 65 hours, about 30 to about 54 hours, or about 48 hours. The mixture is preferably cooled, optionally to a temperature of: about 10° C. to about 40° C., about 15° C. to about 30° C., about 20° C. to about 28° C., or about 20° C. to about 25° C.

Crystalline form 14 of Resmetirom can be isolated from the mixture or the cooled mixture by methods known in the art. For example, crystalline form 14 can be separated by filtering the slurry or decanting the solvent from the slurry or by separating the solid by centrifugation. The isolating method can further comprise washing and drying steps.

According to any embodiment of the process for preparing Form 14 of Resmetirom, the product may be dried under reduced pressure, preferably at a temperature of: about 18° C. to about 40° C., about 20° C. to about 30° C. or about 25° C. for a suitable period of time. For example, the drying may be carried out over a period of about 30 minutes to about 8 hours, about 1 hour to about 6 hours, about 2 hours to about 4 hours, or about 3 hours.

The present disclosure further encompasses processes for preparation of form 17 of Resmetirom.

In one aspect, the process comprises crystallising Resmetirom from a reaction mixture comprising methyl ethyl ketone to obtain form 17.

In embodiments, the present disclosure encompasses a process for preparation of form 17 of Resmetirom wherein the process includes:

a) providing a solution of Resmetirom in methyl ethyl ketone, optionally at an elevated temperature;
b) optionally cooling and optionally stirring to obtain a precipitate.
c) optionally isolating form 17 of Resmetirom.

According to any aspect or embodiment of the process for preparing Form 17 of Resmetirom, the solution step (a) may be heated, optionally to a temperature of: about 40° C. to about 85° C. about 50° C. to about 80° C., about 65° C. to about 75° C., about 68° C. to about 75° C., or about 72° C.

Optionally the solution may be filtered, preferably at the elevated temperature range. In any embodiment, the solution may be cooled to obtain a precipitate. The cooling may be to a temperature of: about −10° C. to about 20° C., about −5° C. to about 10° C., about 0° C. to about 8° C., or about 2° C. to about 5° C. The mixture may be stirred at this temperature for a suitable period of time. Particularly, the mixture may be stirred for about 4 hours to about 30 hours, about 10 hours to about 25 hours, about 14 hours to about 20 hours, or about 18 hours.

Alternatively, the solution in step (a) may be concentrated under reduced pressure to obtain a solid.

The crystalline form 17 of Resmetirom can be isolated by methods known in the art. For example, crystalline form 17 can be separated by filtering the slurry or decanting the solvent from the slurry or by separating the solid by centrifugation. The isolating method can further comprise washing and drying steps.

According to any embodiment of the process for preparing Form 17 of Resmetirom, the product may be dried under reduced pressure, preferably at a temperature of: about 18° C. to about 40° C., about 20° C. to about 30° C. or about 25° C. for a suitable period of time. For example, the drying may be carried out over a period of about 30 minutes to about 28 hours, about 45 minutes to about 24 hours, about 1 hour to about 20 hours.

The present disclosure further encompasses processes for preparation of form 20 of Resmetirom.

In one aspect, the process comprises crystallising Resmetirom from a reaction mixture comprising acetonitrile to obtain form 20.

In embodiments, the present disclosure encompasses a process for preparation of form 20 of Resmetirom wherein the process includes:
a) providing a solution of Resmetirom in acetonitrile, optionally at an elevated temperature;
b) optionally cooling and optionally stirring to obtain a precipitate.
c) optionally isolating form 20 of Resmetirom.

According to any aspect or embodiment of the process for preparing Form 20 of Resmetirom, the solution step (a) may be heated, optionally to a temperature of: about 40° C. to about 90° C. about 60° C. to about 88° C., about 70° C. to about 85° C., about 75° C. to about 82° C., or about 80° C.

Optionally the solution may be filtered, preferably at the elevated temperature range. In any embodiment, the solution may be cooled to obtain a precipitate. The cooling may be to a temperature of: about 10° C. to about 40° C., about 15° C. to about 30° C., about 20° C. to about 28° C., or about 20° C. to about 25° C. The mixture may be stirred at this temperature for a suitable period of time. Particularly, the mixture may be stirred for about 4 hours to about 30 hours, about 10 hours to about 25 hours, about 14 hours to about 20 hours, or about 18 hours.

Crystalline form 20 of Resmetirom can be isolated by methods known in the art. For example, crystalline form 20 can be separated by filtering the slurry or decanting the solvent from the slurry or by separating the solid by centrifugation. The isolating method can further comprise washing and drying steps.

According to any embodiment of the process for preparing Form 20 of Resmetirom, the product may be dried under reduced pressure, preferably at a temperature of: about 20° C. to about 60° C., about 30° C. to about 55° C., or about 40° C. to about 55° C., or about 45° C. for a suitable period of time. For example, the drying may be carried out over a period of about 30 minutes to about 10 hours to about 96 hours, about 20 hours to about 90 hours, about 40 hours to about 80 hours, about 60 hours to about 75 hours, or about 72 hours.

The present disclosure further encompasses processes for preparation of form RC1-A of Resmetirom:nicotinamide.

In one aspect, the process comprises crystallising Resmetirom:nicotinamide from a mixture comprising Resmetirom and nicotinamide optionally in one or more organic solvents, optionally by cooling and/or addition of an antisolvent.

In embodiments, the mixture of Resmetirom and nicotinamide does not include a solvent. In other embodiments the mixture includes Resmetirom and nicotinamide in a slurry, preferably wherein the solvent is dichloromethane and wherein the process comprises seeding with seeds of form RC1-A.

The process for preparing Resmetirom Form RC1-A may comprise slurrying a mixture of Resmetirom and nicotinamide or Resmetirom:nicotinamide (preferably about 1 mole equivalents of nicotinamide), in an antisolvent (optionally dichloromethane, optionally containing seeds of Resmetirom:nicotinamide Form RC1-A, stirring the mixture for a suitable period of time, and optionally isolating the Resmetirom:nicotinamide. The slurrying may be carried out at a temperature of about 10° C. to about 40° C., about 15° C. to about 30° C., about 20° C. to about 28° C., or about 20° C. to about 25° C. The mixture may be stirred for about 4 hours to about 30 hours, about 10 hours to about 25 hours, about 14 hours to about 20 hours, or about 18 hours.

Crystalline form RC1-A of Resmetirom can be isolated by methods known in the art, for example by filtering the slurry or decanting the solvent from the slurry or by separating the solid by centrifugation. The isolating method can further comprise washing and drying steps.

According to any embodiment of the process for preparing Form RC1-A of Resmetirom, the product may be dried under reduced pressure, preferably at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours.

In any embodiment of the above process for preparing Resmetirom Form RC1-A, the Resmetirom:nicotinamide or mixture of Resmetirom and nicotinamide to be slurried in the antisolvent may be prepared by grinding Resmetirom and nicotinamide (preferably about 1 mole equivalent of nicotinamide).

In any embodiment of the above process for preparing Resmetirom Form RC1-A, the Resmetirom:nicotinamide or mixture of Resmetirom and nicotinamide may be prepared by adding nicotinamide (preferably about 1 equivalent) to a solution of Resmetirom in a solvent (preferably 2-methoxyethanol). Preferably, the solution of Resmetirom in the solvent is at elevated temperature. Preferably, the solution is heated to a temperature of: about 40° C. to about 120° C., about 60° C. to about 100° C., about 70° C. to about 90° C., about 75° C. to about 85° C., or about 80° C. The nicotinamide may be added to the hot solution. The mixture may be stirred at the elevated temperature range for a suitable time, optionally for about 10 to about 60 minutes, about 20 to about 40 minutes, or about 30 minutes. The Resmetirom:nicotinamide or mixture of Resmetirom and nicotinamide may be isolated by evaporation of the solvent and drying, for example under reduced pressure. The evaporation may be carried out rapidly, for example in a vacuum oven. Preferably the evaporation and drying is carried out at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours.

Form RC1-A of Resmetirom may alternatively be prepared by grinding Resmetirom with nicotinamide, and heating the ground solid. The grinding may be for any suitable period of time. The heating may be carried out at a temperature of about 100° C. to about 170° C., about 120° C. to about 160° C., about 130° C. to about 150° C., or about 140° C. The heating may be for any suitable period of time to prepare Form RC1-A or Resmetirom. Preferably the heating is carried out over a period of: about 30 minutes to about 6 hours, about 45 minutes to about 4 hours, about 1 hour to about 3 hours, or about 2 hours. The solid may further heated, optionally to a temperature of: about 90° C. to about 150° C., about 100° C. to about 140° C., about 110° C. to about 130° C., or about 120° C. The further heating may be carried out over a period of: about 30 minutes to about 3 hours, about 45 minutes to about 90 minutes, or about 60 minutes. The product may be cooled, or allowed to cool to room temperature.

In another aspect, the present disclosure further encompasses a process for preparation of form RC1-A of Resmetirom:nicotinamide wherein the process includes:

a) providing a mixture of Resmetirom and nicotinamide in dichloromethane;

b) seeding with form RC1-A;

c) optionally stirring the mixture; and d) optionally isolating form RC1-A of Resmetirom:nicotinamide.

In embodiments, the mixture in step a) is preferably a slurry. Preferably, the Resmetirom starting material is form 14 or form 17. The reaction is preferably carried out at room temperature. The mixture either before or after the optional seeding step, may be stirred at room temperature for a suitable period of time, optionally for: about 1 to about 6 days, about 2 to about 4 days, or about 3 days. Crystalline form RC1-A of Resmetirom can be isolated by methods known in the art, for example by filtering the slurry or decanting the solvent from the slurry or by separating the solid by centrifugation. The isolating method can further comprise washing and drying steps. Particularly, the product may be dried under reduced pressure, preferably at a temperature of: about 20° C. to about 60° C., about 30° C. to about 55° C., or about 40° C. to about 55° C., or about 45° C. for a suitable period of time. Optionally, the drying may be carried out over a period of about 4 hours to about 30 hours, about 10 hours to about 25 hours, about 14 hours to about 20 hours, or about 18 hours.

In another aspect, the present disclosure further encompasses a process for preparation of form RC1-A of Resmetirom:nicotinamide wherein the process includes:

i) providing a solution of Resmetirom and nicotinamide in one or more organic solvents;

ii) performing a fast removal of the solvents to obtain a solid;

iii) adding a solvent, preferably dichloromethane to obtain a slurry;

iv) optionally mixing the slurry; and v) optionally isolating form RC1-A of Resmetirom:nicotinamide.

In embodiments, the solvent in step i) is 2-methoxy ethanol.

In embodiments the solution in step i) is prepared by a process comprising:

A) providing Resmetirom in a solution, optionally at elevated temperature;

B) adding nicotinamide and optionally adding another solvent to obtain a solution, optionally at elevated temperature.

In embodiments the solvent in step A) is 2-methoxy ethanol.

In embodiments, fast removal of the solvent/solvents in step ii) is performed by evaporation or by drying in a vacuum oven.

In another aspect, the present disclosure further encompasses a process for preparation of form RC1-A of Resmetirom:nicotinamide wherein the process includes:

a) providing Resmetirom in a solution, optionally at elevated temperature;

b) adding nicotinamide to obtain a solution, optionally at elevated temperature;

c) performing fast removal of the solvent to obtain a solid;

d) optionally mixing the slurry; and e) optionally isolating form RC1-A of Resmetirom:nicotinamide.

In embodiments, the solvent in step a) is 2-methoxy ethanol.

Crystalline form RC1-A of Resmetirom:nicotinamide can be isolated by methods known in the art. For example, crystalline form RC1-A can be separated by filtering the slurry or decanting the solvent from the slurry or by separating the solid by centrifugation. The isolating method can further comprise washing and drying steps.

The present disclosure further encompasses processes for preparation of Resmetirom:caffeine .

The process for preparing Resmetirom Form RC2-A may comprise slurrying a mixture of Resmetirom and caffeine, or Resmetirom:caffeine in an antisolvent (optionally isopropanol), stirring the mixture for a suitable period of time, and optionally isolating the Resmetirom:caffeine. The slurrying may be carried out at a temperature of about 10° C. to about 40° C., about 15° C. to about 30° C., about 20° C. to about 28° C., or about 20° C. to about 25° C. The mixture may be stirred for about 4 hours to about 30 hours, about 10 hours to about 25 hours, about 14 hours to about 20 hours, or about 18 hours. The crystalline form RC2-A of Resmetirom can be isolated by methods known in the art, for example by filtering the slurry or decanting the solvent from the slurry or by separating the solid by centrifugation. The isolating method can further comprise washing and drying steps.

According to any embodiment of the process for preparing Form RC2-A of Resmetirom, the product may be dried under reduced pressure, preferably at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours.

In any embodiment of the above process for preparing Resmetirom Form RC2-A, the Resmetirom:caffeine or mixture of Resmetirom and caffeine may be prepared by adding caffeine (preferably about 1 equivalent) to a solution of Resmetirom in a solvent (preferably 2-methoxyethanol). Preferably, the solution of Resmetirom in the solvent is at elevated temperature. Preferably, the solution is heated to a temperature of: about 40° C. to about 120° C. about 60° C. to about 100° C., about 70° C. to about 90° C., about 75° C. to about 85° C., or about 80° C. The caffeine may be added to the hot solution. A second solvent (preferably ethanol) may be added to the mixture. The mixture may stirred at the elevated temperature range for a suitable time, optionally for about 10 to about 60 minutes, about 20 to about 40 minutes, or about 30 minutes. The Resmetirom:caffeine or mixture of Resmetirom and caffeine may be isolated by evaporation of the solvent, for example under reduced pressure. The evaporation may be carried out rapidly for example in a vacuum oven. Preferably the evaporation and drying is carried out at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours.

Crystalline form RC2-A of Resmetirom can be isolated by methods known in the art, for example by filtering the slurry or decanting the solvent from the slurry or by separating the solid by centrifugation. The isolating method can further comprise washing and drying steps.

According to any embodiment of the process for preparing Form RC2-A of Resmetirom, the product may be dried under reduced pressure, preferably at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours.

In one aspect, the process comprises crystallising Resmetirom:caffeine from a mixture comprising Resmetirom and caffeine optionally in one or more organic solvents, optionally by cooling and/or addition of an antisolvent.

In embodiments, the process includes crystallization of form RC2-A from a mixture that includes Resmetirom and caffeine in a slurry, preferably wherein the solvent is isopropanol and wherein the process comprises seeding with seeds of form RC2-A.

The process for preparing Resmetirom Form RC2-A may comprise slurrying a mixture of Resmetirom and caffeine (preferably about 1 to about 1.1 mole equivalents), or Resmetirom:caffeine an antisolvent (optionally isopropyl ethanol, optionally containing seeds of Resmetirom:caffeine Form RC2-A, stirring the mixture for a suitable period of time, and optionally isolating the Resmetirom:caffeine. The slurrying may be carried out at a temperature of about 10° C. to about 40° C., about 15° C. to about 30° C., about 20° C. to about 28° C., or about 20° C. to about 25° C. The mixture may be stirred for any suitable period of time, preferably about 12 hours to about 7 days, about 1 day to about 5 days, about 2 days to about 6 days, or about 3 to about 4 days. Crystalline form RC2-A of Resmetirom can be isolated by methods known in the art, for example by filtering the slurry or decanting the solvent from the slurry or by separating the solid by centrifugation. The isolating method can further comprise washing and drying steps. Particularly, the product may be dried under reduced pressure, preferably at a temperature of: about 20° C. to about 60° C., about 30° C. to about 55° C., or about 40° C. to about 55° C., or about 45° C. for a suitable period of time. Optionally, the drying may be carried out over a period of about 4 hours to about 30 hours, about 10 hours to about 25 hours, about 14 hours to about 20 hours, or about 18 hours.

In another aspect, the present disclosure further encompasses a process for preparation of form RC2-A of Resmetirom:caffeine wherein the process includes:

i) providing a solution of Resmetirom and caffeine in one or more organic solvents;

ii) performing a fast removal of the solvents to obtain a solid;

iii) adding a solvent, preferably isopropanol to obtain a slurry;

iv) optionally mixing the slurry; and v) optionally isolating form RC2-A of Resmetirom:caffeine.

In embodiments, the solvent in step i) is 2-methoxy ethanol.

In embodiments, the solution in step i) is prepared by a process comprising:

A) providing Resmetirom in a solution, optionally at elevated temperature;

B) adding caffeine and optionally adding another solvent to obtain a solution, optionally at elevated temperature.

In embodiments, the solvent in step A) is 2-methoxy ethanol.

In embodiments, the other solvent in step B) is ethanol.

In embodiments, fast removal of the solvent/solvents in step ii) is performed by evaporation or by drying in a vacuum oven.

In another aspect, the present disclosure further encompasses a process for preparation of form RC2-A of Resmetirom:caffeine wherein the process includes:

a) providing Resmetirom in a solution, optionally at elevated temperature;

b) adding caffeine;

c) ding ethanol and optionally stirring, optionally at elevated temperature until dissolution;

d) performing fast removal of the solvent to obtain a solid;

e) adding isopropanol to provide a slurry;

f) optionally mixing the slurry; and g) optionally isolating form RC2-A of Resmetirom:caffeine.

In embodiments, the solvent in step a) is 2-methoxy ethanol.

In another aspect, the present disclosure further encompasses a process for preparation of form RC2-A of Resmetirom:caffeine wherein the process includes:

a) providing a mixture of Resmetirom and caffeine in isopropanol;

b) seeding with form RC2-A;

c) optionally mixing the slurry; and d) optionally isolating form RC2-A of Resmetirom:caffeine.

In embodiments, the mixture in step a) is preferably a slurry. Preferably, Resmetirom used in step a) is form 14 or form 17.

Crystalline form RC2-A of Resmetirom:caffeine can be isolated by methods known in the art. For example, crystalline form RC2-A can be separated by filtering the slurry or decanting the solvent from the slurry or by or by separating the solid by centrifugation. The isolating method can further comprise washing and drying steps.

In another aspect, the present invention provides a process for preparing Form RC2-B.

The process for preparing Resmetirom Form RC2-B may comprise slurrying a mixture of Resmetirom and caffeine, or Resmetirom:caffeine in an antisolvent (optionally toluene), stirring the mixture for a suitable period of time, and optionally isolating the Resmetirom:caffeine. The slurrying may be carried out at a temperature of about 10° C. to about 40° C., about 15° C. to about 30° C., about 20° C. to about 28° C., or about 20° C. to about 25° C. The mixture may be stirred for about 4 hours to about 30 hours, about 10 hours to about 25 hours, about 14 hours to about 28 hours. The crystalline form RC2-B of Resmetirom can be isolated by methods known in the art, for example by filtering the slurry or decanting the solvent from the slurry or by separating the solid by centrifugation. The isolating method can further comprise washing and drying steps.

According to any embodiment of the process for preparing Form RC2-B of Resmetirom, the product may be dried under reduced pressure, preferably at a temperature of: about 20° C. to about 60° C., about 30° C. to about 55° C., or about 40° C. to about 55° C., or about 45° C. for a suitable period of time. For example, the drying may be carried out over a period of about 4 hours to about 96 hours, about 10 hours to about 90 hours, or about 16 hours to about 80 hours.

In any embodiment of the above process for preparing Resmetirom Form RC2-B, the Resmetirom:caffeine or mixture of Resmetirom and caffeine may be prepared by adding caffeine (preferably about 1 equivalent) to a solution of Resmetirom in a solvent (preferably 2-methoxyethanol). Preferably, the solution of Resmetirom in the solvent is at elevated temperature. Preferably, the solution is heated to a temperature of: about 40° C. to about 120° C. about 60° C. to about 100° C., about 70° C. to about 90° C., about 75° C. to about 85° C., or about 80° C. The caffeine may be added to the hot solution. A second solvent (preferably ethanol) may be added to the mixture. The mixture may stirred at the elevated temperature range for a suitable time, optionally for about 10 to about 60 minutes, about 20 to about 40 minutes, or about 30 minutes. The Resmetirom:caffeine or mixture of Resmetirom and caffeine may be isolated by evaporation of the solvent, for example under reduced pressure. The evaporation may be carried out rapidly for example in a vacuum oven. Preferably the evaporation and drying is carried out at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours.

In any embodiment of the above process for preparing Resmetirom Form RC2-B, the Resmetirom:caffeine or mixture of Resmetirom and caffeine to be slurried in the antisolvent may be prepared by grinding Resmetirom and caffeine (preferably about 1 mole equivalent of caffeine).

In embodiments, the process includes crystallization of form RC2-B from a mixture that includes Resmetirom and caffeine in a slurry, preferably wherein the solvent is toluene and wherein the process comprises seeding with form RC2-B.

In another aspect, the present disclosure further encompasses a process for preparation of form RC2-B of Resmetirom:caffeine wherein the process includes:

i) providing a solution of Resmetirom and caffeine in one or more organic solvents;

ii) performing a fast removal of the solvents to obtain a solid;

iii) adding a solvent, preferably toluene to obtain a slurry;

iv) optionally mixing the slurry; and v) optionally isolating form RC2-B of Resmetirom:caffeine.

In embodiments, the solvent in step i) is 2-methoxy ethanol.

In embodiments the solution in step i) is prepared by a process comprising:

A) providing Resmetirom in a solution with a solvent, optionally at elevated temperature;

B) adding caffeine and optionally adding another solvent to obtain a solution, optionally at elevated temperature.

In embodiments, the solvent in step A) is 2-methoxy ethanol.

In embodiments, the other solvent in step B) is ethanol.

In embodiments, fast removal of the solvent/solvents in step ii) is performed by evaporation or by drying in a vacuum oven.

In another aspect, the present disclosure further encompasses a process for preparation of form RC2-B of Resmetirom:caffeine wherein the process includes:

a) providing Resmetirom in a solution, optionally at elevated temperature;

b) adding caffeine;

c) adding ethanol and optionally stirring, optionally at elevated temperature until dissolution;

d) performing fast removal of the solvent to obtain a solid;

e) adding toluene to provide a slurry;

f) optionally mixing the slurry; and g) optionally isolating form RC2-B of Resmetirom:caffeine.

In embodiments, the solvent in step a) is 2-methoxy ethanol.

In another aspect, the present disclosure further encompasses a process for preparation of form RC2-B of Resmetirom:caffeine wherein the process includes:

a) providing a mixture of Resmetirom and caffeine in toluene;

b) seeding with form RC2-B;

c) optionally mixing the slurry; and d) optionally isolating form RC2-B of Resmetirom:caffeine.

In embodiments, the mixture in step a) is preferably a slurry. Preferably, Resmetirom used in step a) is form 14 or form 17. The reaction is preferably carried out at room temperature. The mixture either before or after the optional seeding step, may be stirred at room temperature for a suitable period of time, optionally for: about 1 to about 6 days, about 2 to about 5 days, or about 3 to about 5 days. Crystalline form RC2-B of Resmetirom can be isolated by methods known in the art, for example by filtering the slurry or decanting the solvent from the slurry or by separating the solid by centrifugation. The isolating method can further comprise washing and drying steps. Particularly, the product may be dried under reduced pressure, preferably at a temperature of: about 20° C. to about 60° C., about 30° C. to about 55° C., or about 40° C. to about 55° C., or about 45° C. for a suitable period of time. Optionally, the drying may be carried out over a period of about 4 hours to about 30 hours, about 10 hours to about 25 hours, about 14 hours to about 20 hours, or about 18 hours.

Crystalline form RC2-B of Resmetirom:caffeine can be isolated by methods known in the art. For example, crystalline form RC2-B can be separated by filtering the slurry or decanting the solvent from the slurry or by or by separating the solid by centrifugation. The isolating method can further comprise washing and drying steps.

The present disclosure further encompasses processes for preparation of Resmetirom: 2-picolinic acid.

The process for preparing Resmetirom Form RC3-A, may comprise evaporation of the solvent from a solution of Resmetirom: 2-picolinic acid in a solvent (preferably 2-methoxyethanol), for example under reduced pressure. The evaporation may be carried out rapidly for example in a vacuum oven, optionally at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours. The solution of Resmetirom: 2-picolinic acid may be prepared by adding 2-picolinic acid (preferably about 1 equivalent) to a solution of Resmetirom in a solvent (preferably 2-methoxyethanol). Preferably, the solution of Resmetirom in the solvent is at elevated temperature. Preferably, the solution is heated to a temperature of: about 40° C. to about 120° C., about 60° C. to about 100° C., about 70° C. to about 90° C., about 75° C. to about 85° C., or about 80° C. The 2-picolinic acid may be added to the hot solution. The mixture may stirred at the elevated temperature range for a suitable time, optionally for about 10 to about 60 minutes, about 20 to about 40 minutes, or about 30 minutes. This mixture is then subjected to evaporation as described above.

In one aspect, the process comprises crystallising Resmetirom: 2-picolinic acid from a mixture comprising Resmetirom and 2-picolinic acid optionally in one or more organic solvents, optionally by cooling and/or addition of an antisolvent.

In another aspect, the present disclosure further encompasses a process for preparation of form RC3-A of Resmetirom: 2-picolinic acid wherein the process includes:

i) providing a solution of Resmetirom and 2-picolinic acid in one or more organic solvents;

ii) performing a fast removal of the solvents to obtain a solid;

iii) optionally adding a solvent to afford a slurry;

iv) optionally mixing the slurry; and v) optionally isolating form RC3-A of Resmetirom: 2-picolinic acid.

In embodiments, the solvent in step i) is 2-methoxy ethanol.

In embodiments, the solution in step i) is prepared by a process comprising:

C) providing Resmetirom in a solution, optionally at elevated temperature;

D) adding 2-picolinic acid and optionally adding another solvent to obtain a solution, optionally at elevated temperature;

In embodiments, the solvent in step E) is 2-methoxy ethanol.

In embodiments, fast removal of the solvent/solvents in step ii) is performed by evaporation or by drying in a vacuum oven.

In another aspect, the present disclosure further encompasses a process for preparation of form RC3-A of Resmetirom: 2-picolinic acid wherein the process includes:

a) providing Resmetirom in a solution, optionally at elevated temperature;

b) adding 2-picolinic acid, to obtain a solution, optionally at elevated temperature;

c) performing fast removal of the solvent to obtain a solid;

d) optionally mixing the slurry; and e) optionally isolating form RC3-A of Resmetirom: 2-picolinic acid.

In embodiments, the solvent in step a) is 2-methoxy ethanol.

Crystalline form RC3-A of Resmetirom: 2-picolinic acid can be isolated by methods known in the art. For example, crystalline form RC3-A can be separated by filtering the slurry or decanting the solvent from the slurry or by or by separating the solid by centrifugation. The isolating method can further comprise washing and drying steps.

In another aspect, the present disclosure further encompasses a process for preparation of form RC3-A of Resmetirom: 2-picolinic acid wherein the process includes:

a) providing a mixture of Resmetirom and 2-picolinic acid in dichloromethane;

b) optionally seeding with form RC3-A;

c) optionally stirring the mixture; and d) optionally isolating form RC3-A of Resmetirom: 2-picolinic acid.

In embodiments, the mixture in step a) is preferably a slurry. Preferably, the Resmetirom starting material is form 14 or form 17. The reaction is preferably carried out at room temperature. The mixture either before or after the optional seeding step, may be stirred at room temperature for a suitable period of time, optionally for: about 1 to about 6 days, about 2 to about 5 days, or about 3 to about 4 days. Crystalline form RC3-A of Resmetirom can be isolated by methods known in the art, for example by filtering the slurry or decanting the solvent from the slurry or by separating the solid by centrifugation. The isolating method can further comprise washing and drying steps. Particularly, the product may be dried under reduced pressure, preferably at a temperature of: about 20° C. to about 60° C., about 30° C. to about 55° C., or about 40° C. to about 55° C., or about 45° C. for a suitable period of time. Optionally, the drying may be carried out over a period of about 4 hours to about 30 hours, about 10 hours to about 25 hours, about 14 hours to about 20 hours, or about 18 hours.

The present disclosure further encompasses processes for preparation of Resmetirom:urea.

The process for preparing Resmetirom Form RC4-A, may comprise evaporation of the solvent from a solution of Resmetirom:urea in a solvent (preferably 2-methoxyethanol), for example under reduced pressure. The evaporation may be carried out rapidly for example in a vacuum oven, optionally at a temperature of: about 20° C. to about 60° C., about 30° C. to about 55° C., or about 40° C. to about 55° C., or about 50° C. for a suitable period of time. For example, the drying may be carried out over a period of about 4 hours to about 30 hours, about 10 hours to about 25 hours, about 14 hours to about 20 hours, or about 18 hours. The solution of Resmetirom:urea may be prepared by adding urea (preferably about 1 equivalent) to a solution of Resmetirom in a solvent (preferably 2-methoxyethanol). Preferably, the solution of Resmetirom in the solvent is at elevated temperature. Preferably, the solution is heated to a temperature of: about 40° C. to about 120° C., about 60° C. to about 100° C., about 70° C. to about 90° C., about 75° C. to about 85° C., or about 80° C. The urea may be added to the hot solution. The mixture may stirred at the elevated temperature range for a suitable time, optionally for about 10 to about 60 minutes, about 20 to about 40 minutes, or about 30 minutes. This mixture is then subjected to evaporation as described above.

In one aspect, the process comprises crystallising Resmetirom:Urea from a mixture comprising Resmetirom and Urea optionally in one or more organic solvents, optionally by cooling and/or addition of an antisolvent.

In another aspect, the present disclosure further encompasses a process for preparation of form RC4-A of Resmetirom:Urea wherein the process includes:

i) providing a solution of Resmetirom and Urea in one or more organic solvents;

ii) performing a fast removal of the solvents to obtain a solid;

iii) optionally adding a solvent to afford a slurry;

iv) optionally mixing the slurry; and v) optionally isolating form RC4-A of Resmetirom:Urea.

In embodiments, the solvent in step i) is 2-methoxy ethanol.

In embodiments, the solution in step i) is prepared by a process comprising:

A) providing Resmetirom in a solution, optionally at elevated temperature;

B) adding urea and optionally adding another solvent to obtain a solution, optionally at elevated temperature;

In embodiments, the solvent in step A) and/or B) is 2-methoxy ethanol

In embodiments, fast removal of the solvent/solvents in step ii) is performed by evaporation or by drying in a vacuum oven.

In another aspect, the present disclosure further encompasses a process for preparation of form RC4-A of Resmetirom:Urea wherein the process includes:

a) providing Resmetirom in a solution, optionally at elevated temperature;

b) adding urea, to obtain a solution, optionally at elevated temperature;

c) performing fast removal of the solvent to obtain a solid;

d) optionally mixing the slurry; and e) optionally isolating form RC4-A of Resmetirom:Urea.

In embodiments, the solvent in step a) is 2-methoxy ethanol.

Crystalline form RC4-A of Resmetirom:Urea can be isolated by methods known in the art. For example, crystalline form RC4-A can be separated by filtering the slurry or decanting the solvent from the slurry or by or by separating the solid by centrifugation. The isolating method can further comprise washing and drying steps.

In another aspect, the present disclosure further encompasses a process for preparation of form RC4-A of Resmetirom:urea wherein the process includes:

a) providing a mixture of Resmetirom and urea in dichloromethane;

b) seeding with form RC4-A;

c) optionally stirring the mixture; and d) optionally isolating form RC4-A of Resmetirom:nicotinamide.

In embodiments, the mixture in step a) is preferably a slurry. Preferably, the Resmetirom starting material is form 14 or form 17. The reaction is preferably carried out at room temperature. The mixture either before or after the optional seeding step, may be stirred at room temperature for a suitable period of time, optionally for: about 1 to about 6 days, about 2 to about 5 days, or about 3 to about 4 days. Crystalline form RC4-A of Resmetirom can be isolated by methods known in the art, for example by filtering the slurry or decanting the solvent from the slurry or by separating the solid by centrifugation. The isolating method can further comprise washing and drying steps. Particularly, the product may be dried under reduced pressure, preferably at a temperature of: about 20° C. to about 60° C., about 30° C. to about 55° C., or about 40° C. to about 55° C., or about 45° C. for a suitable period of time. Optionally, the drying may be carried out over a period of about 4 hours to about 30 hours, about 10 hours to about 25 hours, about 14 hours to about 20 hours, or about 18 hours.

The present disclosure further encompasses processes for preparation of form R3-A of Resmetirom:L-proline, preferably co-crystal.

In one aspect, the process comprises crystallising Resmetirom:L-proline from a mixture comprising Resmetirom and L-proline optionally in one or more organic solvents, optionally by cooling and/or addition of an antisolvent.

In embodiments, the process comprises crystallizing Resmetirom:L-proline from 2-methoxy ethanol.

In embodiments, the process for preparing Form R3-A of Resmetirom:L-proline comprises stirring a mixture of Resmetirom and L-proline in 2-methoxyethanol, preferably at elevated temperature, and cooling. Preferably, the mixture is at a temperature of: about 40° C. to about 120° C., about 60°

C. to about 100° C., about 70° C. to about 90° C., about 75° C. to about 85° C., or about 80° C. The mixture may be cooled to about 10° C. to about 40° C., about 15° C. to about 30° C., about 20° C. to about 28° C., or about 20° C. to about 25° C. The mixture may be stirred at the cooling temperature range for any suitable period of time, preferably about 4 hours to about 30 hours, about 10 hours to about 25 hours, about 14 hours to about 20 hours, or about 18 hours. Form R3-A of Resmetirom:L-proline may be separated by filtering the slurry or decanting the solvent from the slurry or by centrifugation. The isolating method can further comprise washing and drying steps. Preferably the drying is carried out at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours.

Alternatively, the process for preparing Form R3-A of Resmetirom:L-proline comprises stirring a mixture of Resmetirom and L-proline in 2-methoxyethanol, preferably at elevated temperature, and removing the solvent by evaporation, preferably under reduced pressure. Preferably, the mixture is stirred at a temperature of: about 40° C. to about 120° C., about 60° C. to about 100° C., about 70° C. to about 90° C., about 75° C. to about 85° C., or about 80° C. The mixture may be concentrated by evaporation under reduced pressure, e.g. on a rotary evaporator.

In another aspect, the present disclosure further encompasses a process for preparation of form R3-A of Resmetirom:L-proline wherein the process includes:

a) providing a mixture of Resmetirom and L-proline in 2-methoxyethanol;

b) optionally stirring the mixture; and c) optionally isolating form R3-A of Resmetirom:L-proline.

In another aspect, the present disclosure further encompasses a process for preparation of form R3-A of Resmetirom:L-proline wherein the process includes:

i) providing a solution of Resmetirom and L-proline in one or more organic solvents, optionally at an elevated temperature;

ii) optionally stirring the solution until precipitation occurs;

iii) optionally cooling the reaction mixture to room temperature;

iv) optionally stirring; and v) optionally isolating form R3-A of Resmetirom:L-proline.

In embodiments, the solvent in step i) is 2-methoxy ethanol.

In embodiments the solution in step i) is prepared by a process comprising:

A) providing L-proline, optionally in solution, optionally at elevated temperature;

B) adding Resmetirom, optionally in solution, optionally at elevated temperature.

wherein steps A) and B) may be interchangeable.

In embodiments the solvent in step A) is 2-methoxy ethanol.

In embodiments the solvent in step B) is 2-methoxy ethanol.

In another aspect, the present disclosure further encompasses a process for preparation of form R3-A of Resmetirom:L-proline wherein the process includes:

a) providing a solution of Resmetirom and L-proline in 2-methoxy ethanol, optionally at an elevated temperature;
ii) optionally stirring the solution until precipitation occurs;
iii) optionally cooling the reaction mixture to room temperature;
iv) optionally stirring; and
v) optionally isolating form R3-A of Resmetirom:L-proline.

In a particular embodiment the present disclosure encompasses a process for preparation of form R3-A of Resmetirom:L-proline wherein the process includes:

a) Providing a solution of Resmetirom and L-proline in 2-methoxy ethanol at a temperature of about 70° C. to about 100° C.;
b) optionally stirring the solution until precipitation occurs;
c) Optionally cooling the reaction mixture to room temperature;
d) optionally stirring; and
e) Optionally isolating form R3-A of Resmetirom:L-proline.

Crystalline form R3-A of Resmetirom:L-proline can be isolated by methods known in the art. For example, crystalline form R3-A can be separated by filtering the slurry or decanting the solvent from the slurry or by separating the solid by centrifugation. The isolating method can further comprise washing and drying steps.

The present disclosure further encompasses processes for preparation of form R2-A of Resmetirom:piperazine salt.

In embodiments, the process comprises crystallizing Resmetirom:piperazine from 2-methoxy ethanol.

In embodiments, the process for preparing Form R2-A of Resmetirom:piperazine comprises stirring a mixture of Resmetirom and piperazine in 2-methoxyethanol, preferably at elevated temperature, and cooling. Preferably, the mixture is at a temperature of: about 40° C. to about 120° C., about 60° C. to about 100° C., about 70° C. to about 90° C., about 75° C. to about 85° C., or about 80° C. The mixture may be cooled to about 10° C. to about 40° C., about 15° C. to about 30° C., about 20° C. to about 28° C., or about 20° C. to about 25° C. The mixture may be stirred at the cooling temperature range for any suitable period of time, preferably about 4 hours to about 30 hours, about 10 hours to about 25 hours, about 14 hours to about 20 hours, or about 18 hours. Form R2-A of Resmetirom:piperazine may be separated by filtering the slurry or decanting the solvent from the slurry or by centrifugation. The isolating method can further comprise washing and drying steps. Preferably the drying is carried out at a temperature of: about 20° C. to about 60° C., about 30° C. to about 55° C., or about 40° C. to about 55° C., or about 45° C. for a suitable period of time. For example, the drying may be carried out over a period of about 4 hours to about 30 hours, about 10 hours to about 25 hours, about 14 hours to about 20 hours, or about 18 hours.

Alternatively, the process for preparing Form R2-A of Resmetirom:piperazine comprises stirring a mixture of Resmetirom and piperazine in 2-methoxyethanol, preferably at elevated temperature, and removing the solvent by evaporation, preferably under reduced pressure. Preferably, the mixture is stirred at a temperature of: about 40° C. to about 120° C., about 60° C. to about 100° C., about 70° C. to about 90° C., about 75° C. to about 85° C., or about 80° C. The mixture may be concentrated by evaporation under reduced pressure, e.g. in a vacuum oven. The product may be dried. Preferably the evaporation and drying is carried out at a temperature of: about 20° C. to about 60° C., about 30° C. to about 55° C., or about 40° C. to about 55° C., or about 45° C. for a suitable period of time. For example, the evaporation and drying may be carried out over a period of about 10 hours to about 36 hours, about 15 hours to about 30 hours, about 18 hours to about 26 hours, or about 24 hours.

In one aspect, the process comprises crystallising Resmetirom:piperazine salt from a mixture comprising Resmetirom and piperazine optionally in one or more organic solvents, optionally by cooling and/or addition of an anti-solvent.

In embodiments, the process comprises crystallizing Resmetirom piperazine salt from 2-methoxy ethanol.

In another aspect, the present disclosure further encompasses a process for preparation of form R2-A of Resmetirom piperazine salt wherein the process includes:

a) providing a mixture of Resmetirom and piperazine in 2-methoxy ethanol;
b) optionally seeding with form R2-A;
c) optionally mixing the mixture; and
d) optionally isolating form R2-A of Resmetirom piperazine salt In another aspect, the present disclosure further encompasses a process for preparation of form R2-A of Resmetirom piperazine salt wherein the process includes:

i) providing a solution of Resmetirom and piperazine in one or more organic solvents, optionally at an elevated temperature;
ii) optionally stirring the solution until precipitation occurs;
iii) optionally cooling the reaction mixture to room temperature;
iv) optionally stirring; and
v) optionally isolating form R2-A of Resmetirom piperazine salt.

In embodiments, the solvent in step i) is 2-methoxy ethanol.

In embodiments the solution in step i) is prepared by a process comprising:

A) providing piperazine, optionally in solution, optionally at elevated temperature;
B) adding Resmetirom, optionally in solution, optionally at elevated temperature.
wherein steps A) and B) may be interchangeable.

In embodiments the solvent in step A) is 2-methoxy ethanol.

In embodiments the solvent in step B) is 2-methoxy ethanol.

In any of the disclosed processes for preparing form R3-A of Resmetirom piperazine salt, the molar ratio of piperazine to Resmetirom may be from about 0.5:1 to about 1:1, optionally about 1:1.

In another aspect, the present disclosure further encompasses a process for preparation of form R2-A of Resmetirom piperazine salt wherein the process includes:

a) providing a solution of Resmetirom and L-proline in 2-methoxy ethanol, optionally at an elevated temperature;
ii) optionally stirring the solution until precipitation occurs;
iii) optionally cooling the reaction mixture to room temperature;
iv) optionally stirring; and
v) optionally isolating form R3-A of Resmetirom:L-proline.

In a particular embodiment the present disclosure encompasses a process for preparation of form R2-A of Resmetirom piperazine salt wherein the process includes:

a) Providing a solution of Resmetirom and piperazine in 2-methoxy ethanol at a temperature of about 70° C. to about 100° C.;

b) optionally stirring the solution until precipitation occurs;

c) optionally cooling the reaction mixture to room temperature;

d) optionally stirring; and e) optionally isolating form R3-A of Resmetirom:L-proline.

Crystalline form R3-A of Resmetirom:L-proline can be isolated by methods known in the art. For example, crystalline form R3-A can be separated by filtering the slurry or decanting the solvent from the slurry or by separating the solid by centrifugation. The isolating method can further comprise washing and drying steps.

The present disclosure also encompasses any one of the crystalline forms of the present disclosure, or cocrystals, or salts thereof, or the crystalline forms RC1-A of Resmetirom:nicotinamide, crystalline form RC2-A and RC2-B of Resmetirom:caffeine, crystalline form RC3-A of Resmetirom:2-picolinic acid, form R2-A of Resmetirom:piperazine salt, form R3-A of Resmetirom:L-proline, and crystalline form RC4-A of Resmetirom:Urea produced by any one of the processes of the present disclosure.

The present disclosure includes processes for preparing the above mentioned pharmaceutical compositions. The processes include combining any one or a combination of the crystalline polymorphs of Resmetirom, or cocrystals, or the salts thereof, or any one of the above described crystalline polymorphs of Resmetirom:nicotinamide, Resmetirom:caffeine, Resmetirom: 2-picolinic acid, Resmetirom:Urea, Resmetirom:piperazine and/or Resmetirom:L-proline of the present disclosure with at least one pharmaceutically acceptable excipient.

Pharmaceutical combinations or formulations of the present disclosure contain any one or a combination of the solid state forms of Resmetirom, or cocrystals, or the salts thereof or any one of the above described crystalline polymorphs of Resmetirom:nicotinamide, Resmetirom:caffeine, Resmetirom: 2-picolinic acid, Resmetirom:Urea Resmetirom:piperazine and/or Resmetirom:L-proline of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Resmetirom and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Resmetirom can be administered. Resmetirom may be formulated for administration to a mammal, in embodiments to a human, by injection. Resmetirom can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Resmetirom and the pharmaceutical compositions and/or formulations of Resmetirom of the present disclosure can be used as medicaments, in embodiments in the treatment of non-alcoholic steatohepatitis (NASH), non-alcoholic fatty liver disease (NAFLD) and associated dyslipidemias.

The present disclosure also provides methods of treating non-alcoholic steatohepatitis (NASH), non-alcoholic fatty liver disease (NAFLD) and associated dyslipidemias by administering a therapeutically effective amount of any one or a combination of the crystalline polymorphs of Resmetirom of the present disclosure, or at least one of the above pharmaceutical compositions and/or formulations, to a subject in need of the treatment.

Further aspects and embodiments of the present disclosure are set out in the numbered clauses below:

A1. Crystalline Resmetirom:nicotinamide.

A2. Crystalline Resmetirom:nicotinamide according to Clause A1 which is a co-crystal.

A3. Crystalline Resmetirom:nicotinamide according to Clause A1 which is a salt.

A4. A crystalline product according to any of Clauses A1, A2, or A3, designated form RC1-A, which is characterized by data selected from one or more of the following:

i) an XRPD pattern having peaks at 8.7, 18.6, 21.1, 25.3 and 26.4 degrees 2-theta±0.2 degrees 2-theta;

ii) an XRPD pattern as depicted in FIG. 23;

iii) a solid state $^{13}$C NMR spectrum with characteristic peaks at 159.9, 153.4, 136.2, 134.9 and 119.1 ppm±0.2 ppm iv) a solid state $^{13}$C NMR spectrum having the following chemical shift absolute differences from reference peak at 170.2 ppm±1 ppm: 10.3, 16.8, 34.0, 35.3 and 51.0 ppm±0.1 ppm v) a solid state $^{13}$C NMR spectrum substantially as depicted in FIG. 31, 32 or 33; and vi) combinations of these data.

A5. A crystalline product according to Clause A4, characterized by the XRPD pattern having peaks at 8.7, 18.6, 21.1, 25.3 and 26.4 degrees 2-theta±0.2 degrees 2-theta, and also having one, two, three or four additional peaks selected from 11.5, 12.6, 13.9, 20.1 and 22.0 degrees two theta±0.2 degrees two theta.

A6. A crystalline product according to any one of clauses A1-A5 which is characterized by an X-ray powder diffraction pattern having peaks at 8.7, 11.5, 12.6, 13.9, 18.6, 20.1, 21.1, 22.0, 25.3 and 26.4 degrees 2-theta±0.2 degrees 2-theta.

A7. A crystalline product according to any of clauses A1-A6, wherein the molar ratio of Resmetirom to nicotinamide is 1:1.

A8. A crystalline product according to any of Clauses A4-A7, which is an anhydrous form.

A9. A crystalline product according to any of Clauses A4-A8, which contains: no more than about 20%, no more than about 10%, no more than about 5%, no more than about 2%, no more than about 1% or about 0% of any other crystalline forms of Resmetirom:nicotinamide or crystalline Resmetirom:nicotinamide salt.

A10. A crystalline product according to any of Clauses A4-A9, designated form RC1-A which contains: no more than about 20%, no more than about 10%, no more than about 5%, no more than about 2%, no more than about 1% or about 0% of amorphous Resmetirom: nicotinamide or Resmetirom:nicotinamide salt.

A11. A process for the preparation of a product according to any of clauses A1-A10 comprising crystallising Resmetirom:nicotinamide from a mixture comprising Resmetirom and nicotinamide optionally in one or more organic solvents, optionally by cooling and/or addition of an anti solvent.

A12. A process according to clause A11 wherein the mixture of Resmetirom and nicotinamide does not include a solvent.

A13. process according to Clause A12, comprising grinding Resmetirom with nicotinamide, and heating the ground solid.

A14. A process according to Clause A13, wherein the heating is carried out at a temperature of about 100° C. to about 170° C., about 120° C. to about 160° C., about 130° C. to about 150° C., or about 140° C.

A15. A process according to Clause A14, wherein the heating is carried out over a period of: about 30 minutes to about 6 hours, about 45 minutes to about 4 hours, about 1 hour to about 3 hours, or about 2 hours.

A16. A process according to any of Clauses A14 or A15, wherein the mixture is further heated, optionally to a temperature of: about 90° C. to about 150° C., about 100° C. to about 140° C., about 110° C. to about 130° C., or about 120° C.

A17. A process according to Clause A16, wherein the further heating is carried out over a period of: about 30 minutes to about 3 hours, about 45 minutes to about 90 minutes, or about 60 minutes.

A18. A process according to Clause A17, wherein the product is cooled, or allowed to cool to room temperature.

A19. A process according to clause A11, comprising slurrying a mixture of Resmetirom and nicotinamide or Resmetirom:nicotinamide in an antisolvent, preferably dichloromethane, optionally in the presence of seeds of form RC1-A.

A20. A process according to Clause A19, wherein the slurrying is carried out by stirring at a temperature of about 10° C. to about 40° C., about 15° C. to about 30° C., about 20° C. to about 28° C., or about 20° C. to about 25° C.

A21. A process according to any of Clauses A19 or A20, wherein crystalline form RC1-A of Resmetirom is isolated by filtering the slurry or decanting the solvent from the slurry or by separating the solid by centrifugation, and optionally further comprising washing and drying steps.

A22. A process according to Clause A21, wherein the product is dried under reduced pressure, preferably at a temperature of: about 20° C. to about 60° C., about 30° C. to about 55° C., or about 40° C. to about 55° C., or about 45° C.

A23. A process according to Clause A22, wherein the drying is carried out over a period of about 4 hours to about 30 hours, about 10 hours to about 25 hours, about 14 hours to about 20 hours, or about 18 hours.

A24. A process according to any of Clauses A19-A23, wherein the Resmetirom:nicotinamide or mixture of Resmetirom and nicotinamide to be slurried in the antisolvent is prepared by grinding Resmetirom and nicotinamide, preferably about 1 mole equivalent of nicotinamide.

A25. A process according to any of Clauses A20-A24, wherein the slurrying takes place in the presence of seeds of Form RC1-A.

A26. A process according to any of Clauses A20-A25, wherein the mixture is slurried for about 4 hours to about 30 hours, about 10 hours to about 25 hours, about 14 hours to about 20 hours, or about 18 hours.

A27. A process according to Clause A19-A23, wherein the Resmetirom:nicotinamide or mixture of Resmetirom and nicotinamide is prepared by adding nicotinamide, preferably about 1 equivalent, to a solution of Resmetirom in a solvent.

A28. A process according to Clause A27 wherein the solvent is 2-methoxyethanol.

A29. A process according to Clause A27 or Clause A28, wherein the solution of Resmetirom in the solvent is at elevated temperature, preferably at temperature of: about 40° C. to about 120° C., about 60° C. to about 100° C., about 70° C. to about 90° C., about 75° C. to about 85° C., or about 80° C.

A30. A process according to any of clauses A27-A29, wherein the nicotinamide is added to the hot solution.

A31. A process according to Clause A29 or Clause A30, wherein the mixture is stirred at the elevated temperature range for: about 10 to about 60 minutes, about 20 to about 40 minutes, or about 30 minutes.

A32. A process according to any of Clauses A27-A31, wherein Resmetirom:nicotinamide or mixture of Resmetirom and nicotinamide is isolated by evaporation of the solvent, preferably under reduced pressure and at elevated temperature, and optionally drying, preferably under reduced pressure and at elevated temperature.

A33. A process according to Clause A32, wherein the evaporation is carried out rapidly under reduced pressure and elevated temperature, optionally in a vacuum oven, and optionally wherein the product is further dried.

A34. A process according to Clause A33, wherein the evaporation and drying is carried out at a temperature of: about 20° C. to about 60° C., about 30° C. to about 55° C., or about 40° C. to about 55° C., or about 45° C.

A35. A process according to Clause A34 wherein the drying is carried out over a period of about 4 hours to about 30 hours, about 10 hours to about 25 hours, about 14 hours to about 20 hours, or about 18 hours.

A36. A process according to any of Clauses A19-A23 or A26-A34, wherein the slurrying in the antisolvent is carried out without seeds.

A37. A process according to any of Clause A19-A23, wherein the Resmetirom starting material is Form 14 or Form 17.

A38. A process according to Clause A37, wherein the Resmetirom:nicotinamide or mixture of Resmetirom and nicotinamide is prepared by adding nicotinamide, preferably about 1 equivalent, to a mixture of Resmetirom in the antisolvent, preferably dichloromethane.

A39. A process according to Clause A37 or A38, wherein the slurrying in the antisolvent is carried out in the presence of seeds of Resmetirom Form RC1-A.

A40. A process according to any of Clauses A37-A39, wherein the slurry is stirred for: about 1 day to about 6 days, about 2 days to about 5 days, or about 2 days to about 4 days.

A41. A process for preparation of form RC1-A of Resmetirom:nicotinamide according to Clause
   a) providing a mixture of Resmetirom, optionally wherein the Resmetirom is crystalline Form 14 or Form 17, and nicotinamide in dichloromethane;
   b) seeding with form RC1-A;
   c) optionally mixing the mixture; and
   d) optionally isolating form RC1-A of Resmetirom: nicotinamide.

A42. A process for preparation of form RC1-A of Resmetirom:nicotinamide according to Clause A11, wherein the process includes:
   i) providing a solution of Resmetirom and nicotinamide in one or more organic solvents;
   ii) performing a fast removal of the solvents to obtain a solid;
   iii) adding a solvent, preferably dichloromethane to obtain a slurry;
   iv) optionally mixing the slurry; and
   v) optionally isolating form RC1-A of Resmetirom: nicotinamide.

A43. The process according to clause A42 wherein the solvent in step i) is 2-methoxy ethanol.

A44. The process according to any one of clauses A41, A42 or A43, wherein the solution in step i) is prepared by a process comprising:
   A) providing Resmetirom in a solution, optionally at elevated temperature;
   B) adding nicotinamide and optionally adding another solvent to obtain a solution, optionally at elevated temperature.

A45. The process according to clause A44 wherein the solvent in step A) is 2-methoxy ethanol.

A46. The process according to any one of clauses A42-A45 wherein fast removal of the solvent/solvents in step ii) is performed by evaporation, under reduced pressure and elevated temperature, or by drying in a vacuum oven, preferably at elevated temperature.

A47. A process for preparation of form RC1-A of Resmetirom:nicotinamide according to Clause
   a) providing Resmetirom in a solution, optionally at elevated temperature;
   b) adding nicotinamide to obtain a solution, optionally at elevated temperature;
   c) performing fast removal of the solvent to obtain a solid;
   d) optionally mixing the slurry; and
   e) optionally isolating form RC1-A of Resmetirom: nicotinamide.

A48. The process according to clause A47 wherein the solvent in step a) is 2-methoxy ethanol.

A49. The process according to any one of clauses A47-A48 wherein fast removal of the solvent/solvents in step c) is performed by evaporation, preferably under reduced pressure and at elevated temperature, or by drying in a vacuum oven, preferably at elevated temperature.

A50. A crystalline product obtainable by a process according to any of clauses A11-A42.

B1. Crystalline Resmetirom:caffeine.

B2. Crystalline Resmetirom:caffeine according to Clause B1, which is a co-crystal. B3. Crystalline Resmetirom: caffeine according to Clause B1, which is a salt.

B4. A crystalline product according to any of Clauses B1, B2 or B3, designated form RC2-A, which is characterized by data selected from one or more of the following:
   i) an XRPD pattern having peaks at 6.0, 6.8, 10.4, 11.2 and 16.4 degrees 2-theta±0.2 degrees 2-theta;
   ii) an XRPD pattern as depicted in FIG. 24;
   iii) a solid state $^{13}$C NMR spectrum with characteristic peaks at 139.5, 118.8, 106.7, 34.0 and 29.6 ppm±0.2 ppm;
   iv) a solid state $^{13}$C NMR spectrum having the following chemical shift absolute differences from reference peak at 161.0 ppm±1 ppm: 21.4, 42.2, 54.3, 127.0 and 131.4 ppm±0.1 ppm;
   v) a solid state $^{13}$C NMR spectrum substantially as depicted in FIG. 34, 35 or 36; and
   vi) combinations of these data.

B5. A crystalline product according to Clause B4, designated form RC2-A, characterized by the XRPD pattern having peaks at 6.0, 6.8, 10.4, 11.2 and 16.4 degrees 2-theta±0.2 degrees 2-theta, and also having one, two, three or four additional peaks selected from 14.6, 15.6, 17.8, 19.5 and 26.9 degrees two theta±0.2 degrees two theta.

B6. A crystalline product according to any one of clauses B1-B5 which is characterized by an X-ray powder diffraction pattern having peaks at 6.0, 6.8, 10.4, 11.2, 14.6, 15.6, 16.4, 17.8, 19.5 and 26.9 degrees 2-theta±0.2 degrees 2-theta.

B7. A crystalline product according to any of clauses B1-B6, wherein the molar ratio of Resmetirom and caffeine is 1:1.

B8. A crystalline product according to any of Clauses B4-B7, which is an anhydrous form.

B9. A crystalline product according to any of Clauses B4-B8, which contains: no more than about 20%, no more than about 10%, no more than about 5%, no more than about 2%, no more than about 1% or about 0% of any other crystalline forms of Resmetirom:caffeine or crystalline Resmetirom:caffeine salt.

B10. A crystalline product according to any of Clauses B4-B9, designated form RC2-A which contains: no more than about 20%, no more than about 10%, no more than about 5%, no more than about 2%, no more than about 1% or about 0% of amorphous Resmetirom: caffeine or Resmetirom:caffeine salt.

B11. A process for preparation of Resmetirom:caffeine according to any one of clauses B1-B10 wherein the process comprises crystallising Resmetirom:caffeine from a mixture comprising Resmetirom and caffeine optionally in one or more organic solvents, optionally by cooling and/or addition of an antisolvent.

B12. A process for preparation of form RC2-A of Resmetirom:caffeine according to Clause B11, wherein the process comprises crystallising form RC2-A of Resmetirom:caffeine from a mixture comprising Resmetirom, preferably wherein the Resmetirom is crystalline form 14 or form 17, and caffeine in a slurry, preferably wherein the solvent is isopropanol and wherein the process comprises seeding with seeds of form RC2-A.

B13. A process for preparation of form RC2-A of Resmetirom:caffeine according to Clause B11, wherein the process includes:
   i) providing a solution of Resmetirom and caffeine in one or more organic solvents;
   ii) performing a fast removal of the solvents to obtain a solid;
   iii) adding a solvent, preferably isopropanol to obtain a slurry;
   iv) optionally mixing the slurry; and
   v) optionally isolating form RC2-A of Resmetirom: caffeine.

B14. A process according to clause B13 wherein the solvent in step i) is 2-methoxy ethanol.

B15. A process according to any one of clauses B13-B14 wherein the solution in step i) is prepared by a process comprising:
   A) providing Resmetirom in a solution in a solvent, optionally at elevated temperature;
   B) adding caffeine and optionally adding a second solvent to obtain a solution, optionally at elevated temperature.

B16. A process according to clause B15 wherein the solvent in step A) is 2-methoxy ethanol.

B17. A process according to any one of clauses B15-B16 wherein the second solvent in step B) is ethanol.

B18. The process according to any one of clauses B13-B17 wherein fast removal of the solvent/solvents in step ii) is performed by evaporation, preferably under reduced pressure and at elevated temperature, or in a vacuum oven, preferably at elevated temperature, and optionally further drying the product.

B19. A process for preparation of form RC2-A of Resmetirom:caffeine according to Clause B11, wherein the process includes:
   a) providing Resmetirom in a solution, optionally at elevated temperature;
   b) adding caffeine;
   c) adding ethanol and optionally stirring, optionally at elevated temperature until dissolution;
   d) performing fast removal of the solvent to obtain a solid;
   e) adding isopropanol to provide a slurry;
   f) optionally mixing the slurry; and
   g) optionally isolating form RC2-A of Resmetirom: caffeine.

B20. The process according to clause B19 wherein the solvent in step a) is 2-methoxy ethanol.

B21. The process according to any one of clauses B19-B20 wherein fast removal of the solvent/solvents in step d) is performed by evaporation, preferably under reduced pressure and at elevated temperature, or by drying in a vacuum oven, preferably at elevated temperature.

B22. A process for preparation of RC2-A according to Clause B11, comprising slurrying a mixture of Resmetirom and caffeine or Resmetirom:caffeine in an antisolvent, optionally in the presence of seeds of form RC2-A.

B23. The process according to clause B22 wherein the antisolvent is isopropanol.

B24. A process according to any of Clauses B22 or B23, wherein crystalline form RC1-A of Resmetirom is isolated by filtering the slurry or decanting the solvent from the slurry or by separating the solid by centrifugation, and optionally further comprising washing and drying steps.

B25. A process according to Clause B24, wherein the product is dried under reduced pressure, preferably at a temperature of: about 20° C. to about 60° C., about 30° C. to about 55° C., or about 40° C. to about 55° C., or about 45° C.

B26. A process according to Clause B25, wherein the drying is carried out over a period of about 4 hours to about 30 hours, about 10 hours to about 25 hours, about 14 hours to about 20 hours, or about 18 hours.

B27. A process according to any of Clauses B22-B26, wherein the slurrying takes place in the presence of seeds of Form RC2-A.

B28. A process according to any of Clauses B22-B27, wherein the slurrying is for a period of about 4 hours to about 30 hours, about 10 hours to about 25 hours, about 14 hours to about 20 hours, or about 18 hours.

B29. A process according to any one of clauses B22-B26 wherein the Resmetirom:caffeine or mixture of Resmetirom and caffeine is prepared by adding caffeine, preferably about 1 equivalent, to a solution of Resmetirom in a solvent.

B30. A process according to Clause B29, wherein the solvent is 2-methoxy ethanol.

B31. The process according to Clause B29 or B30 wherein the solution is heated to a temperature of: about 40° C. to about 120° C., about 60° C. to about 100° C., about 70° C. to about 90° C., about 75° C. to about 85° C., or about 80° C.

B32. The process according to any one of clauses B31 wherein caffeine and optionally another solvent is added.

B33. The process according to clause B34 wherein the other solvent added is ethanol.

B34. A process according to Clause B32 or Clause B33, wherein the mixture is stirred at the elevated temperature range for: about 10 to about 60 minutes, about 20 to about 40 minutes, or about 30 minutes.

B35. A process according to any of Clauses B27-B34, wherein Resmetirom:nicotinamide or mixture of Resmetirom and nicotinamide is isolated by evaporation of the solvent, preferably under reduced pressure and at elevated temperature, and optionally drying, preferably under reduced pressure and at elevated temperature.

B36. A process according to Clause B35, wherein the evaporation is carried out rapidly under reduced pressure and elevated temperature, optionally in a vacuum oven, and optionally wherein the product is further dried.

B37. A process according to Clause B36, wherein the evaporation and drying is carried out at a temperature of: about 20° C. to about 60° C., about 30° C. to about 55° C., or about 40° C. to about 55° C., or about 45° C.

B38. A process according to any of Clauses B35-B37 wherein the drying is carried out over a period of about 4 hours to about 30 hours, about 10 hours to about 25 hours, about 14 hours to about 20 hours, or about 18 hours.

B39. A process according to any of Clauses B22-B26, wherein the Resmetirom starting material is Form 14 or Form 17.

B40. A process according to Clause B39, wherein the Resmetirom:nicotinamide or mixture of Resmetirom and nicotinamide is prepared by adding nicotinamide, preferably about 1 equivalent, to a mixture of Resmetirom in the antisolvent, preferably isopropanol.

B41. A process according to Clause B39 or B40, wherein the slurrying in the antisolvent is carried out in the presence of seeds of Resmetirom Form RC2-A.

B42. A process according to any of Clauses B39-B41, wherein the slurry is stirred for: about 1 day to about 6 days, about 2 days to about 5 days, or about 2 days to about 4 days.

B43. A crystalline product obtainable by a process according to any of Clauses B11-B42.

C1. A crystalline product according to Clause B1, B2 or B3, designated form RC2-B, which is characterized by data selected from one or more of the following:
  i) an XRPD pattern having peaks at 8.9, 10.6, 11.2, 14.5 and 17.1 degrees 2-theta±0.2 degrees 2-theta;
  ii) an XRPD pattern as depicted in FIG. 25;
  iii) a solid state $^{13}$C NMR spectrum with characteristic peaks at 145.9, 142.7, 108.7, 33.5 and 28.1 ppm±0.2 ppm;
  iv) a solid state $^{13}$C NMR spectrum having the following chemical shift absolute differences from reference peak at 161.1 ppm±1 ppm: 15.2, 18.45, 52.4, 127.6 and 133.0 ppm±0.1 ppm;
  v) a solid state $^{13}$C NMR spectrum substantially as depicted in FIG. 37, 38 or 39; and
  vi) combinations of these data.

C2. A crystalline product according to Clause C1, designated form RC2-B, characterized by the XRPD pattern having peaks at 8.9, 10.6, 11.2, 14.5 and 17.1 degrees 2-theta±0.2 degrees 2-theta, and also having one, two, three or four additional peaks selected from 14.9, 20.0, 21.9, 24.5 and 28.2 degrees two theta±0.2 degrees two theta.

C3. A crystalline product according to any one of clauses C1-C2 which is characterized by an X-ray powder diffraction pattern having peaks at 8.9, 10.6, 11.2, 14.5, 14.9, 17.1, 20.0, 21.9, 24.5 and 28.2 degrees 2-theta±0.2 degrees 2-theta.

C4. A crystalline product according to any of clauses C1-C3, wherein the molar ratio of Resmetirom and caffeine is 1:1.

C5. A crystalline product according to any of Clauses C1-C4, wherein the crystalline form is an anhydrous form.

C6. A crystalline product according to any of Clauses C1-05, which contains: no more than about 20%, no more than about 10%, no more than about 5%, no more than about 2%, no more than about 1% or about 0% of any other crystalline forms of Resmetirom:caffeine or crystalline Resmetirom:caffeine salt.

C7. A crystalline product according to any of Clauses C1-C6, which contains: no more than about 20%, no more than about 10%, no more than about 5%, no more than about 2%, no more than about 1% or about 0% of amorphous Resmetirom:caffeine or Resmetirom:caffeine salt.

C8. A process for preparation of form RC2-B of Resmetirom:caffeine according to any one of clauses C1-C7 wherein the process comprises crystallising form RC2-B of Resmetirom:caffeine from a mixture comprising Resmetirom, preferably wherein the Resmetirom is crystalline form 14 or form 17, and caffeine in a slurry, preferably wherein the solvent is toluene and wherein the process comprises seeding with seeds of form RC2-B.

C9. A process for preparation of form RC2-B of Resmetirom:caffeine according to any one of clauses C1-C7 wherein the process includes:
  i) providing a solution of Resmetirom and caffeine in one or more organic solvents;
  ii) performing a fast removal of the solvents to obtain a solid;
  iii) adding a solvent, preferably toluene to obtain a slurry;
  iv) optionally mixing the slurry; and
  v) optionally isolating form RC2-B of Resmetirom:caffeine.

C10. A process according to clause C9 wherein the solvent in step i) is 2-methoxy ethanol.

C11. A process according to any one of clauses C9-C10 wherein the solution in step i) is prepared by a process comprising:
  A) providing Resmetirom in a solvent to form a solution, optionally at elevated temperature;
  B) adding caffeine and optionally adding a second solvent to obtain a solution, optionally at elevated temperature.

C12. A process according to clause C11 wherein the solvent in step A) is 2-methoxy ethanol.

C13. A process according to any one of clauses C11-C12 wherein the second solvent in step B) is ethanol.

C14. The process according to any one of clauses C9-C13 wherein fast removal of the solvent/solvents in step ii) is performed by evaporation or by drying in a vacuum oven.

C15. A process for preparation of form RC2-B of Resmetirom:caffeine according to any one of clauses C1-C7 wherein the process includes:
  a) providing Resmetirom in a solution, optionally at elevated temperature;
  b) adding caffeine;
  c) adding ethanol and optionally stirring, optionally at elevated temperature until dissolution;
  d) performing fast removal of the solvent to obtain a solid;
  e) adding isopropanol to provide a slurry;
  f) optionally mixing the slurry; and
  g) optionally isolating form RC2-B of Resmetirom:caffeine.

C16. The process according to clause C15 wherein, the solvent in step a) is 2-methoxy ethanol.

C17. The process according to any one of clauses C15-C16 wherein fast removal of the solvent/solvents in step d) is performed by evaporation or by drying in a vacuum oven.

C18. A process for preparation of RC2-B according to any one of clauses C1-C7 comprising slurrying a mixture of Resmetirom and caffeine or Resmetirom:caffeine in an antisolvent, optionally in the presence of seeds of form RC2-B.

C19. The process according to clause C18 wherein the antisolvent is toluene.

C20. A process according to any of Clauses C18 or C19, wherein crystalline form RC2-B of Resmetirom is isolated by filtering the slurry or decanting the solvent from the slurry or by separating the solid by centrifugation, and optionally further comprising washing and drying steps.

C21. A process according to Clause C20, wherein the product is dried under reduced pressure, preferably at a temperature of: about 20° C. to about 60° C., about 30° C. to about 55° C., or about 40° C. to about 55° C., or about 45° C.

C22. A process according to Clause 20 or Clause 21, wherein the drying is carried out over a period of about 4 hours to about 30 hours, about 10 hours to about 25 hours, about 14 hours to about 20 hours, or about 18 hours.

C23. The process according to any one of clauses C18-C22 wherein the Resmetirom:caffeine or mixture of Resmetirom and caffeine is prepared by a process comprising adding caffeine, preferably about 1 equivalent, to a solution of Resmetirom in a solvent.

C24. A process according to Clause C23, wherein the solvent is 2-methoxyethanol.

C25. The process according to Clause C23 or Clause C24, wherein the solution is heated to a temperature of: about 40° C. to about 120° C., about 60° C. to about 100° C., about 70° C. to about 90° C., about 75° C. to about 85° C., or about 80° C.

C26. The process according to clause C25, wherein caffeine is added to the hot solution and optionally another solvent is added.

C27. The process according to clause C26 wherein the other solvent added is ethanol.

C28. A process according to any of Clauses C18-C27, wherein the mixture is stirred at the elevated temperature range for: about 10 to about 60 minutes, about 20 to about 40 minutes, or about 30 minutes.

C29. A process according to any of Clauses C18-C28, wherein Resmetirom:nicotinamide or mixture of Resmetirom and nicotinamide is isolated by evaporation of the solvent, preferably under reduced pressure and at elevated temperature, and drying, preferably under reduced pressure and at elevated temperature.

C30. A process according to Clause C29, wherein the evaporation is carried out rapidly under reduced pressure and elevated temperature, optionally in a vacuum oven, and optionally wherein the product is further dried.

C31. A process according to Clause C30, wherein the evaporation and drying is carried out at a temperature of: about 20° C. to about 60° C., about 30° C. to about 55° C., or about 40° C. to about 55° C., or about 45° C.

C32. A process according to any of Clauses C20-C31 wherein the drying is carried out over a period of about 4 hours to about 30 hours, about 10 hours to about 25 hours, about 14 hours to about 20 hours, or about 18 hours.

C33. A process according to any of Clauses C18-C32, wherein mixture of Resmetirom and caffeine or Resmetirom:caffeine in the antisolvent, is slurried for about 4 hours to about 30 hours, about 10 hours to about 25 hours, about 14 hours to about 20 hours, or about 18 hours.

C34. A process according to any of Clauses C18-C22, wherein the Resmetirom:caffeine or mixture of Resmetirom and caffeine to be slurried in the antisolvent is prepared by grinding Resmetirom and caffeine, preferably about 1 mole equivalent of caffeine.

C35. A process according to any of Clauses C18-C22 or C34, wherein the slurrying takes place in the presence of seeds of Form RC2-B.

C36. A process according to any of Clauses C34-C35, wherein the mixture is slurried for about 10 hours to about 72 hours, about 20 hours to about 60 hours, about 35 hours to about 50 hours, or about 48 hours.

C37. A process according to Clause C34-C36, wherein the slurrying is carried out by stirring at a temperature of about 10° C. to about 40° C., about 15° C. to about 30° C., about 20° C. to about 28° C., or about 20° C. to about 25° C.

C38. A process according to any of Clauses C18-C22, wherein the Resmetirom starting material is Form 14 or Form 17.

C39. A process according to Clause C38, wherein the Resmetirom:caffeine or mixture of Resmetirom and caffeine is prepared by adding caffeine, preferably about 1 equivalent, to a mixture of Resmetirom in the antisolvent, preferably toluene.

C40. A process according to Clause C38-C39, wherein the slurrying in the antisolvent is carried out in the presence of seeds of Resmetirom Form RC2-B.

C41. A process according to any of Clauses C38-C40, wherein the slurry is stirred for: about 1 day to about 6 days, about 2 days to about 5 days, or about 2 days to about 4 days.

C42. A product obtainable by a process according to any of Clauses C11-C41.

D1. Crystalline Resmetirom: 2-picolinic acid.

D2. Crystalline Resmetirom: 2-picolinic acid according to Clause D1, which is a co-crystal.

D3. Crystalline Resmetirom: 2-picolinic acid according to Clause D1, which is a salt.

D4. A crystalline product according to Clause D1, D2 or D3, designated form RC3-A, which is characterized by data selected from one or more of the following:
   i) an XRPD pattern having peaks at 6.0, 6.8, 12.9, 15.6 and 26.9 degrees 2-theta±0.2 degrees 2-theta;
   ii) an XRPD pattern as depicted in FIG. 26; and
   iii) combinations of these data.

D5. A crystalline product according to Clause D4, designated form RC3-A, characterized by the XRPD pattern having peaks at 6.0, 6.8, 12.9, 15.6 and 26.9 degrees 2-theta±0.2 degrees 2-theta, and also having one, two, three or four additional peaks selected from 10.4, 14.8, 18.0, 18.5 and 24.7 degrees two theta±0.2 degrees two theta.

D6. A crystalline product according to any of Clauses D1-D5, which is an anhydrous form.

D7. A crystalline product according to any of Clauses D1-D6, which contains: no more than about 20%, no more than about 10%, no more than about 5%, no more than about 2%, no more than about 1% or about 0% of any other crystalline forms of Resmetirom: 2-picolinic acid or crystalline Resmetirom: 2-picolinic acid salt.

D8. A crystalline product according to any of Clauses D1-D7, which contains: no more than about 20%, no more than about 10%, no more than about 5%, no more than about 2%, no more than about 1% or about 0% of amorphous Resmetirom: 2-picolinic acid or Resmetirom: 2-picolinic acid salt.

D9. A process for preparation of crystalline form RC3-A of Resmetirom: 2-picolinic acid according to any one of clauses D1-D8 wherein the process includes:
   i) providing a solution of Resmetirom and 2-picolinic acid in one or more organic solvents;
   ii) performing a fast removal of the solvents to obtain a solid;
   iii) optionally adding a solvent to afford a slurry;
   iv) optionally mixing the slurry; and v) optionally isolating form RC3-A of Resmetirom: 2-picolinic acid.

D10. The process according to clause D9 wherein the solvent in step i) is 2-methoxy ethanol.

D11. The process according to any one of clauses D9-D10 wherein, the solution in step i) is prepared by a process comprising:

A) providing Resmetirom in a solution, optionally at elevated temperature;

B) adding 2-picolinic acid and optionally adding another solvent to obtain a solution, optionally at elevated temperature.

D12. The process according to clause D11 wherein the solvent in step B) is 2-methoxy ethanol.

D13. The process according to any one of clauses D9-D12 wherein fast removal of the solvent/solvents in step ii) is performed by evaporation or by drying in a vacuum oven.

D14. A process for preparation of form RC3-A of Resmetirom: 2-picolinic acid according to any one of clauses D4-D8 wherein the process includes:

a) providing Resmetirom in a solution, optionally at elevated temperature;

b) adding 2-picolinic acid to obtain a solution, optionally at elevated temperature;

c) performing fast removal of the solvent to obtain a solid;

d) optionally mixing the slurry; and e) optionally isolating form RC3-A of Resmetirom: 2-picolinic acid.

D15. The process according to clause D14 wherein the solvent in step a) is 2-methoxy ethanol.

D16. The process according to any one of clauses D14-D15 wherein fast removal of the solvent/solvents in step c) is performed by evaporation or by drying in a vacuum Oven.

D17. A process for preparation of RC3-A according to any of Clauses D1-D8, comprising slurrying a mixture of Resmetirom and picolinic acid or Resmetirom:picolinic acid in an antisolvent, preferably dichloromethane, optionally in the presence of seeds of form RC3-A.

D18. A process according Clause D17, wherein crystalline form RC3-A of Resmetirom is isolated by filtering the slurry or decanting the solvent from the slurry or by separating the solid by centrifugation, and optionally further comprising washing and drying steps.

D19. A process according to Clause D18, wherein the product is dried under reduced pressure, preferably at a temperature of: about 20° C. to about 60° C., about 30° C. to about 55° C., or about 40° C. to about 55° C., or about 45° C.

D20. A process according to Clause D18 or Clause D19, wherein the drying is carried out over a period of about 4 hours to about 30 hours, about 10 hours to about 25 hours, about 14 hours to about 20 hours, or about 18 hours.

D21. A process according to any of Clauses D17-D20, wherein the slurrying is carried out at a temperature of about 10° C. to about 40° C., about 15° C. to about 30° C., about 20° C. to about 28° C., or about 20° C. to about 25° C.

D22. A process according to any of Clauses D17-D21, wherein the mixture is stirred for about 12 hours to about 10 days, about 1 day to about 8 days, about 2 days to about 6 days, or about 3 days to about 5 days, or about 4 days.

D23. A process according to any of Clauses D17-D22, wherein the Resmetirom:picolinic acid or mixture of Resmetirom and picolinic acid is prepared by adding picolinic acid, preferably about 1 equivalent, to a slurry of Resmetirom in the antisolvent.

D24. A process according to Clause D17-D23, wherein the slurrying in the antisolvent is carried out in the presence of seeds of Resmetirom Form RC2-A.

D25. A process for preparing Resmetirom Form RC3-A as defined in any of Clauses D1-D8, comprising evaporation of the solvent from a solution of Resmetirom: 2-picolinic acid in a solvent under reduced pressure and at elevated temperature, and optionally further drying the product.

D26. A process according to Clause D25, wherein the evaporation is carried out rapidly, optionally in a vacuum oven.

D27. A process according to Clause D26, wherein the evaporation is carried out at a temperature of: about 20° C. to about 60° C., about 30° C. to about 55° C., or about 40° C. to about 55° C., or about 45° C.

D28. A process according to Clause D26 or D27, wherein the evaporation and drying is carried out over a period of about 4 hours to about 30 hours, about 10 hours to about 25 hours, about 14 hours to about 20 hours, or about 18 hours.

D29. A process according to any of Clauses D25-D28, wherein the solution of Resmetirom: 2-picolinic acid is prepared by adding 2-picolinic acid, preferably about 1 equivalent, to a solution of Resmetirom in a solvent.

D30. A process according to any of clauses D25-D29, wherein the solvent is 2-methoxy ethanol.

D31. A process according to any of Clauses D25-D30, wherein the solution of Resmetirom in the solvent is at elevated temperature, optionally at a temperature of: about 40° C. to about 120° C., about 60° C. to about 100° C., about 70° C. to about 90° C., about 75° C. to about 85° C., or about 80° C.

D32. A process according to any of Clauses D25-D31, wherein the 2-picolinic acid is added to the hot solution.

D33. A process according to any of Clauses D25-D32, wherein the mixture is stirred at the elevated temperature range for about 10 to about 60 minutes, about 20 to about 40 minutes, or about 30 minutes prior to the evaporation.

D34. A process for preparation of form RC3-A of Resmetirom: 2-picolinic acid wherein the process comprising:

a) providing a mixture of Resmetirom and 2-picolinic acid in dichloromethane;

b) optionally seeding with form RC3-A;

c) optionally stirring the mixture; and d) optionally isolating form RC3-A of Resmetirom: 2-picolinic acid.

D35. A process according to Clause D34, wherein the mixture in step a) is a slurry.

D36. A process according to Clause D34 or D35 wherein the Resmetirom starting material is form 14 or form 17.

D37. A process according to any of Clauses D34-D36, wherein reaction is carried out at room temperature.

D38. A process according to any of Clauses D34-D37, wherein the mixture, either before or after the optional seeding step, is stirred for: about 1 to about 6 days, about 2 to about 5 days, or about 3 to about 4 days.

D39. A process according to any of Clauses D34-D38, wherein crystalline form RC3-A of Resmetirom is isolated by filtering the slurry or decanting the solvent from the slurry or by separating the solid by centrifugation, and optionally further comprising washing and drying steps.

D40. A process according to Clause D39, wherein the product is dried under reduced pressure, preferably at a temperature of: about 20° C. to about 60° C., about 30° C. to about 55° C., or about 40° C. to about 55° C., or about 45° C., optionally over a period of about 4 hours to about 30 hours, about 10 hours to about 25 hours, about 14 hours to about 20 hours, or about 18 hours.

D41. A crystalline product obtainable by a process according to any one of clauses D9-D40.

E1. Crystalline Resmetirom:Urea.

E2. Crystalline Resmetirom:Urea according to Clause E1, which is a co-crystal.

E3. Crystalline Resmetirom:Urea according to Clause E1, which is a salt.

E4. A crystalline product according to Clause E1, E2 or E3, designated form RC4-A, which is characterized by data selected from one or more of the following:
i) an XRPD pattern having peaks at 7.6, 12.6, 15.7, 16.4 and 16.9 degrees 2-theta±0.2 degrees 2-theta;
ii) an XRPD pattern as depicted in FIG. 27; and
iii) combinations of these data.

E5. A crystalline product according to Clause E4, designated form RC4-A, characterized by the XRPD pattern having peaks at 7.6, 12.6, 15.7, 16.4 and 16.9 degrees 2-theta±0.2 degrees 2-theta, and also having one, two, three or four additional peaks selected from 15.2, 19.1, 19.6, 22.0 and 23.6 degrees two theta±0.2 degrees two theta.

E6. A crystalline product according to any of Clauses E1-E5, wherein the crystalline form is an anhydrous form.

E7. A crystalline product according to any of Clauses E4-E6, which contains: no more than about 20%, no more than about 10%, no more than about 5%, no more than about 2%, no more than about 1% or about 0% of any other crystalline forms of Resmetirom:Urea or Resmetirom.

E8. A crystalline product according to any of Clauses E4-E7, which contains: no more than about 20%, no more than about 10%, no more than about 5%, no more than about 2%, no more than about 1% or about 0% of amorphous Resmetirom:Urea or Resmetirom.

E9. A process for preparation of crystalline form RC4-A of Resmetirom:Urea according to any one of clauses E1-E8 wherein the process includes:
i) providing a solution of Resmetirom and urea in one or more organic solvents;
ii) performing a fast removal of the solvents to obtain a solid;
iii) optionally adding a solvent to afford a slurry;
iv) optionally mixing the slurry; and
v) optionally isolating form RC4-A of Resmetirom: urea.

E10. The process according to clause E9 wherein the solvent in step i) is 2-methoxy ethanol.

E11. The process according to any one of clauses E9-E10, wherein the solution in step i) is prepared by a process comprising:
A) providing Resmetirom in a solution, optionally at elevated temperature;
B) adding urea and optionally adding another solvent to obtain a solution, optionally at elevated temperature.

E12. The process according to clause E11 wherein the solvent in step A) and/or B) is 2-methoxy ethanol E13. The process according to any one of clauses E9-E12 wherein fast removal of the solvent/solvents in step ii) is performed by evaporation or by drying in a vacuum oven.

E14. A process for preparation of form RC4-A of Resmetirom:Urea according to any one of clauses E4-E8 wherein the process includes:
a) providing Resmetirom in a solution, optionally at elevated temperature;
b) adding urea to obtain a solution, optionally at elevated temperature;
c) performing fast removal of the solvent to obtain a solid;
d) optionally mixing the slurry; and
e) optionally isolating form RC4-A of Resmetirom: urea.

E15. The process according to clause E14 wherein the solvent in step a) is 2-methoxy ethanol.

E16. The process according to any one of clauses E14-E15 wherein fast removal of the solvent/solvents in step c) is performed by evaporation or by drying in a vacuum oven.

E17. A process for preparation of RC4-A according to any one of clause E4-E8 comprises crystallising Resmetirom:urea from a mixture comprising Resmetirom and urea optionally in one or more organic solvents, optionally by cooling and/or addition of an antisolvent.

E18. A process according to clause E18 wherein the mixture includes Resmetirom and urea in a slurry, preferably wherein the solvent is dichloromethane and wherein the process comprises seeding with seeds of form RC4-A.

E19. A process for preparation of form RC4-A of Resmetirom:urea according to any one of clauses E1-E8 wherein the process includes:
a) providing a mixture of Resmetirom, preferably wherein the Resmetirom is crystalline form 14 or form 17, and urea in dichloromethane;
b) seeding with form RC4-A;
c) optionally mixing the mixture; and
d) optionally isolating form RC4-A of Resmetirom: urea.

E20. A process for preparing Resmetirom Form RC4-A as defined in any of Clauses E1-E8, comprising evaporation of the solvent from a solution of Resmetirom:urea in a solvent, and optionally further drying the product.

E21. A process according to Clause E20, wherein the evaporation is carried out rapidly, preferably under reduced pressure and at elevated temperature, optionally in a vacuum oven, preferably at elevated temperature.

E22 A process according to Clause E20 or E21, wherein the evaporation is carried out at a temperature of: at a temperature of: about 20° C. to about 60° C., about 30° C. to about 55° C., or about 40° C. to about 55° C., or about 50° C.

E23. A process according to any of E20, E21, and E22, wherein the evaporation and drying is carried out over a period of about 4 hours to about 30 hours, about 10 hours to about 25 hours, about 14 hours to about 20 hours, or about 18 hours.

E24. A process according to any of Clauses E20-E23, wherein the solution of Resmetirom:urea may be prepared by adding urea, preferably about 1 equivalent, to a solution of Resmetirom in a solvent.

E25. A process according to any of clauses E20-E24, wherein the solvent is 2-methoxyethanol.

E26. A process according to any of Clauses E20-E25, wherein the solution of Resmetirom in the solvent is at elevated temperature, optionally at a temperature of: about 40° C. to about 120° C., about 60° C. to about 100° C., about 70° C. to about 90° C., about 75° C. to about 85° C., or about 80° C.

E27. A process according to any of Clauses E20-E26, wherein the urea is added to the hot solution.

E28. A process according to any of Clauses E20-E27, wherein the mixture is stirred at the elevated temperature range for about 10 to about 60 minutes, about 20 to about 40 minutes, or about 30 minutes prior to the evaporation.

E29. A process for preparation of form RC4-A of Resmetirom: 2-picolinic acid wherein the process comprises:
  a) providing a mixture of Resmetirom and urea in dichloromethane;
  b) optionally seeding with form RC4-A;
  c) optionally stirring the mixture; and
  d) optionally isolating form RC4-A of Resmetirom: urea.

E30. A process according to Clause E29, wherein the mixture in step a) is a slurry.

E31. A process according to Clause E29 or E30, wherein the Resmetirom starting material is form 14 or form 17.

E32. A process according to any of Clauses E29, E30 or E31, wherein reaction is carried out at room temperature.

E33. A process according to any of Clauses E29-E32, wherein the mixture, either before or after the optional seeding step, is stirred for: about 1 to about 6 days, about 2 to about 5 days, or about 3 to about 4 days.

E34. A process according to any of Clauses E29-E33, wherein crystalline form RC3-A of Resmetirom is isolated by filtering the slurry or decanting the solvent from the slurry or by separating the solid by centrifugation, and optionally further comprising washing and drying steps.

E35. A process according to Clause E34, wherein the product is dried under reduced pressure, preferably at a temperature of: about 20° C. to about 60° C., about 30° C. to about 55° C., or about 40° C. to about 55° C., or about 45° C.

E36. A process according to Clause E34 or E35, wherein the drying is over a period of about 4 hours to about 30 hours, about 10 hours to about 25 hours, about 14 hours to about 20 hours, or about 18 hours.

E37. A crystalline product obtainable by a process according to any one of clauses E9-E36.

F1. Crystalline Resmetirom:L-proline.

F2. Crystalline Resmetirom:L-proline according to Clause F1, which is a co-crystal.

F3. Crystalline Resmetirom:L-proline according to Clause F1, which is a salt.

F4. A crystalline product according to Clause F1, F2, or F3, designated form R3-A, which is characterized by data selected from one or more of the following:
  i) an XRPD pattern having peaks at 8.6, 9.3, 10.3, 16.9 and 18.3 degrees 2-theta±0.2 degrees 2-theta;
  ii) an XRPD pattern as depicted in FIG. 21;
  iii) a solid state $^{13}$C NMR spectrum with characteristic peaks at 161.7, 152.4, 135.1, 60.8 and 46.5 ppm±0.2 ppm iv) a solid state $^{13}$C NMR spectrum having the following chemical shift absolute differences from reference peak at 174.7 ppm±1 ppm: 13.0, 22.3, 39.6, 114.0 and 128.3 ppm±0.1 ppm;
  v) a solid state $^{13}$C NMR spectrum substantially as depicted in FIG. 40, 41 or 42; and
  vi) combinations of these data.

F5. A crystalline product according to Clause F4, designated form R3-A, characterized by the XRPD pattern having peaks at 8.6, 9.3, 10.3, 16.9 and 18.3 degrees 2-theta±0.2 degrees 2-theta, and also having one, two, three or four additional peaks selected from 16.4, 20.1, 21.9, 24.8 and 25.8 degrees two theta±0.2 degrees two theta.

F6. A crystalline product according to any one of clauses F1-F5 which is characterized by an X-ray powder diffraction pattern having peaks at 8.6, 9.3, 10.3, 16.4, 16.9, 18.3, 20.1, 21.9, 24.8 and 25.8 degrees 2-theta±0.2 degrees 2-theta.

F7. A crystalline product according to any of clauses F1-F6, wherein the molar ratio of Resmetirom to L-proline is 1:1.

F8. A crystalline product according to any of Clauses F1-F7, which is an anhydrous form.

F9. A crystalline product according to any of Clauses F4-F8, which contains: no more than about 20%, no more than about 10%, no more than about 5%, no more than about 2%, no more than about 1% or about 0% of any other crystalline forms of Resmetirom:nicotinamide or crystalline Resmetirom:nicotinamide salt.

F10. A crystalline product according to any of Clauses F4-F8, which contains: no more than about 20%, no more than about 10%, no more than about 5%, no more than about 2%, no more than about 1% or about 0% of amorphous Resmetirom:nicotinamide or Resmetirom: nicotinamide salt.

F11. A process for preparation of form R3-A according to any of Clauses F1-F10, comprising crystallising Resmetirom:L-proline from a mixture comprising Resmetirom and L-proline optionally in one or more organic solvents, optionally by cooling and/or addition of an anti solvent.

F12. A process according to clause F11 wherein the solvent is 2-methoxyethanol.

F13. A process according to any one of clauses F11 or F12 wherein the process comprises stirring a mixture of Resmetirom and L-proline in 2-methoxyethanol, preferably at elevated temperature, and cooling.

F14. The process according to clause F13 wherein the mixture is stirred at a temperature of: about 40° C. to about 120° C., about 60° C. to about 100° C., about 70° C. to about 90° C., about 75° C. to about 85° C., or about 80° C., and cooled to about 10° C. to about 40° C., about 15° C. to about 30° C., about 20° C. to about 28° C., or about 20° C. to about 25° C.

F15. The process according to any one of clauses F11-F14 wherein Form R3-A of Resmetirom:L-proline is separated by filtering the slurry or decanting the solvent from the slurry or by centrifugation.

F16. A process for preparation of form R3-A according to any of clauses F1-F10, comprising stirring a mixture of Resmetirom and L-proline in 2-methoxyethanol preferably at elevated temperature, and removing the solvent by evaporation, preferably under reduced pressure.

F17. A process for preparation of form R3-A of Resmetirom:L-proline according to any one of clauses F1-F10 wherein the process includes:

a) providing a mixture of Resmetirom and L-proline in 2-methoxyethanol;

b) optionally stirring the mixture; and c) optionally isolating form R3-A of Resmetirom:L-proline.

F18. A process for preparation of form R3-A of Resmetirom:L-proline according to any one of clause F1-F10 wherein the process includes:

i) providing a solution of Resmetirom and L-proline in one or more organic solvents, optionally at an elevated temperature;

ii) optionally stirring the solution until precipitation occurs;

iii) optionally cooling the reaction mixture to room temperature;

iv) optionally stirring; and v) optionally isolating form R3-A of Resmetirom:L-proline.

F19. A process according to clause F18 wherein the solvent in step i) is 2-methoxyethanol.

F20. A process according to any one of clauses F18 or F19 wherein the solution in step i) is prepared by a process comprising:

A) providing L-proline, optionally in solution, optionally at elevated temperature;

B) adding Resmetirom, optionally in solution, optionally at elevated temperature.

wherein steps A) and B) may be interchangeable.

F21. A process according to any one of clauses F18-F20 wherein the solvent in both step A and B is 2-methoxyethanol.

F22. A process for preparation of form R3-A of Resmetirom:L-proline according to any one of clauses F1-F10 wherein the process includes:

i) providing a solution of Resmetirom and L-proline in in 2-methoxy ethanol, optionally at an elevated temperature;

ii) optionally stirring the solution until precipitation occurs;

iii) optionally cooling the reaction mixture to room temperature;

iv) optionally stirring; and v) optionally isolating form R3-A of Resmetirom:L-proline.

F23. A process for preparation of form R3-A of Resmetirom:L-proline according to any one of clauses F1-F10 wherein the process includes:

i) providing a solution of Resmetirom and L-proline in in 2-methoxy ethanol, at a temperature of about 70° C. to about 100° C.;

ii) optionally stirring the solution until precipitation occurs;

iii) optionally cooling the reaction mixture to room temperature;

iv) optionally stirring; and v) optionally isolating form R3-A of Resmetirom:L-proline.

F24. A crystalline product obtainable by a process according to any one of clauses F11-F23.

G1. Resmetirom piperazine salt.

G2. Resmetirom piperazine salt according to Clause G1, which is crystalline.

G3. A crystalline form of Resmetirom piperazine salt according to Clause G2, designated form R2-A, which is characterized by data selected from one or more of the following:

i) an XRPD pattern having peaks at 10.7, 15.7, 19.5, 22.0 and 23.9 degrees 2-theta±0.2 degrees 2-theta;

ii) an XRPD pattern as depicted in FIG. 20;

iii) a solid state $^{13}C$ NMR spectrum with characteristic peaks at 161.1, 152.0, 138.0, 40.9 and 39.9 ppm±0.2 ppm iv) a solid state $^{13}C$ NMR spectrum having the following chemical shift absolute differences from reference peak at 164.6 ppm±1 ppm: 3.5, 12.6, 26.6, 123.7 and 124.7 ppm±0.1 ppm;

v) a solid state $^{13}C$ NMR spectrum substantially as depicted in FIG. 43, 44 or 45; and combinations of these data G4. A product according to any of Clauses G1-G3, designated form R2-A, which is characterized by the XRPD pattern having peaks at 10.7, 15.7, 19.5, 22.0 and 23.9 degrees 2-theta±0.2 degrees 2-theta, and also having one, two, three or four additional peaks selected from 12.0, 12.3, 12.6, 17.1 and 21.5 degrees two theta±0.2 degrees two theta.

G5. A crystalline product according to any of clauses G2-G4, which is characterized by an X-ray powder diffraction pattern having peaks at 10.7, 12.0, 12.3, 12.6, 15.7, 17.1, 19.5, 21.5, 22.0 and 23.9 degrees 2-theta±0.2 degrees 2-theta.

G6. A crystalline product according to any of clauses G1-G5, wherein the molar ratio of Resmetirom to piperazine is 2:1.

G7. A crystalline product according to any of G1-G6, which is an anhydrous form.

G8. A crystalline product according to any of Clauses G3-G7, which contains: no more than about 20%, no more than about 10%, no more than about 5%, no more than about 2%, no more than about 1% or about 0% of any other crystalline forms of Resmetirom piperazine salt.

G9. A crystalline product according to any of Clauses G1-G8, which contains: no more than about 20%, no more than about 10%, no more than about 5%, no more than about 2%, no more than about 1% or about 0% of amorphous Resmetirom piperazine salt.

G10. A process for preparation of form R2-A according to any one of clause G1-G9 comprising crystallising Resmetirom piperazine salt from a mixture comprising Resmetirom and piperazine optionally in one or more organic solvents, optionally by cooling and/or addition of an anti solvent.

G11. A process according to clause G10 wherein the solvent is 2-methoxyethanol.

G12. A process according to any one of clauses G10 or G11 wherein the process comprises stirring a mixture of Resmetirom and piperazine in 2-methoxyethanol, preferably at elevated temperature, and cooling.

G13. The process according to clause G12 wherein the mixture is stirred at a temperature of: about 40° C. to about 120° C., about 60° C. to about 100° C., about 70° C. to about 90° C., about 75° C. to about 85° C., or about 80° C., and cooled to about 10° C. to about 40° C., about 15° C. to about 30° C., about 20° C. to about 28° C., or about 20° C. to about 25° C.

G14. The process according to any one of clauses G10-G13 wherein Form R2-A of Resmetirom piperazine salt is separated by filtering the slurry or decanting the solvent from the slurry or by centrifugation.

G15. A process for preparation of form R2-A according to any one of G1-G9 comprising stirring a mixture of Resmetirom and piperazine in 2-methoxyethanol preferably at elevated temperature, and removing the solvent by evaporation, preferably under reduced pressure.

G16. A process for preparation of form R2-A of Resmetirom piperazine salt according to any one of clause G1-G9 wherein the process includes:
  a) providing a mixture of Resmetirom and piperazine in 2-methoxy ethanol;
  b) optionally seeding with form R2-A;
  c) optionally mixing the mixture; and
  d) optionally isolating form R2-A of Resmetirom piperazine salt.

G17. A process for preparation of form R2-A of Resmetirom piperazine salt according to any one of clause G1-G9 wherein the process includes:
  i) providing a solution of Resmetirom and piperazine in one or more organic solvents, optionally at an elevated temperature;
  ii) optionally stirring the solution until precipitation occurs;
  iii) optionally cooling the reaction mixture to room temperature;
  iv) optionally stirring; and
  v) optionally isolating form R2-A of Resmetirom piperazine salt.

G18. A process according to clause G17 wherein the solvent in step i) is 2-methoxyethanol.

G19. A process according to any one of clauses G17 or G18 wherein the solution in step i) is prepared by a process comprising:
  A) providing piperazine, optionally in solution, optionally at elevated temperature;
  B) adding Resmetirom, optionally in solution, optionally at elevated temperature.
    wherein steps A) and B) may be interchangeable.

G20. A process according to clause G19 wherein the solvent in both steps A and B is 2-methoxy ethanol.

G21. A process for preparation of form R2-A of Resmetirom piperazine salt according to any one of clause G1-G9 wherein the process includes:
  i) providing a solution of Resmetirom and piperazine in in 2-methoxy ethanol, optionally at an elevated temperature;
  ii) optionally stirring the solution until precipitation occurs;
  iii) optionally cooling the reaction mixture to room temperature;
  iv) optionally stirring; and
  v) optionally isolating form R2-A of Resmetirom piperazine salt.

G22. A process for preparation of form R2-A of Resmetirom piperazine salt according to any one of clause G1-G9 wherein the process includes:
  i) providing a solution of Resmetirom and piperazine in 2-methoxy ethanol, at a temperature of about 70° C. to about 100° C.;
  ii) optionally stirring the solution until precipitation occurs;
  iii) optionally cooling the reaction mixture to room temperature;
  iv) optionally stirring; and v) optionally isolating form R2-A of Resmetirom piperazine salt.

G23. A product obtainable by a process according to any of clauses G10-G22.

H1. A crystalline form of Resmetirom, designated form 20, which is characterized by data selected from one or more of the following:
  i) an XRPD pattern having peaks at 6.5, 9.6, 10.1, 19.0 and 23.3 degrees 2-theta±0.2 degrees 2-theta;
  ii) an XRPD pattern as depicted in FIG. 16;
  iii) a solid state $^{13}$C NMR spectrum with characteristic peaks at 161.0, 155.0, 151.1, 145.3 and 121.8 ppm±0.2 ppm
  iv) a solid state $^{13}$C NMR spectrum having the following chemical shift absolute differences from reference peak at 162.4 ppm±1 ppm: 1.4, 7.5, 11.3, 17.1 and 40.6 ppm±0.1 ppm;
  v) a solid state $^{13}$C NMR spectrum substantially as depicted in FIG. 28, 29 or 30; and combinations of these data H2. A crystalline product according to Clause H1, designated form 20, characterized by the XRPD pattern having peaks at 6.5, 9.6, 10.1, 19.0 and 23.3 degrees 2-theta±0.2 degrees 2-theta, and also having one, two, three or four additional peaks selected from 11.6, 16.2, 19.5, 21.8 and 24.9 degrees two theta±0.2 degrees two theta.

H3. A crystalline product according to any one of clauses H1 or H2 which is characterized by an X-ray powder diffraction pattern having peaks at 6.5, 9.6, 10.1, 11.6, 16.2, 19.0, 19.5, 21.8, 23.3 and 24.9 degrees 2-theta±0.2 degrees 2-theta.

H4. A crystalline product according to any of clauses H1-H3, which is an anhydrous form.

H5. A crystalline product according to any of Clauses H1-H4, which contains: no more than about 20%, no more than about 10%, no more than about 5%, no more than about 2%, no more than about 1% or about 0% of any other crystalline forms of Resmetirom.

H6. A crystalline product according to any of H1-H5, which contains: no more than about 20%, no more than about 10%, no more than about 5%, no more than about 2%, no more than about 1% or about 0% of amorphous Resmetirom.

H7. A process for preparation of form 20 of Resmetirom according to any one of clauses H1-H6, wherein the process comprises crystallising Resmetirom from a reaction mixture comprising acetonitrile.

H8. The process according to clause H7 wherein the process includes:
  a) providing a solution of Resmetirom in acetonitrile, optionally at an elevated temperature;
  b) optionally cooling and optionally stirring to obtain a precipitate; and
  c) optionally isolating form 20 of Resmetirom.

H9. The process according to clause H8 wherein the solution in step (a) is heated optionally to a temperature of: about 40° C. to about 90° C., about 60° C. to about 88° C., about 70° C. to about 85° C., about 75° C. to about 82° C., or about 80° C.

H10. The process according to clause H9 wherein the solution is filtered at the elevated temperature.

H11. A process according to any of Clauses H8-H9, wherein the solution is cooled to obtain a precipitate.

H12. A process according to Clause H11, wherein the cooling is to a temperature of: about 10° C. to about 40°

C., about 15° C. to about 30° C., about 20° C. to about 28° C., or about 20° C. to about 25° C.

H13. A process according to any of Clauses H11-H12, wherein the mixture is stirred at the cooled temperature range for about 4 hours to about 30 hours, about 10 hours to about 25 hours, about 14 hours to about 20 hours, or about 18 hours.

H14. A process according to any of Clauses H8-H13, wherein crystalline form 20 of Resmetirom is isolated by filtering, decanting the solvent or by separating the solid by centrifugation, and optionally washing and drying.

H15. A process according to Clause H14, wherein the product is dried under reduced pressure, preferably at a temperature of: about 20° C. to about 60° C., about 30° C. to about 55° C., or about 40° C. to about 55° C., or about 45° C.

H16. A process according to any of Clauses H14-H15, wherein the drying is carried out over a period of about 30 minutes to about 10 hours to about 96 hours, about 20 hours to about 90 hours, about 40 hours to about 80 hours, about 60 hours to about 75 hours, or about 72 hours.

H17. A product obtainable by a process according to any of clauses H7-H16.

J1. A crystalline form of Resmetirom, designated form 14, which is characterized by data selected from one or more of the following:
   i) an XRPD pattern having peaks at 9.8, 11.1 and 23.2 degrees 2-theta±0.2 degrees 2-theta;
   ii) an XRPD pattern as depicted in FIG. 11; and combinations of these data J2. A crystalline form of Resmetirom according to Clause J1 which is a methyl THF solvate.

J3. A Crystalline form of Resmetirom according to any of Clauses J1 or J2, which is a mono methyl THF solvate, optionally containing: about 11% to about 16% of methyl THF by weight, as determined by TGA.

J4. A crystalline product according to any of Clauses J1-J3, which contains: no more than about 20%, no more than about 10%, no more than about 5%, no more than about 2%, no more than about 1% or about 0% of any other crystalline forms of Resmetirom.

J5. A crystalline product according to any of J1-J4, which contains: no more than about 20%, no more than about 10%, no more than about 5%, no more than about 2%, no more than about 1% or about 0% of amorphous Resmetirom.

J6. A process for preparation of form 14 of Resmetirom according to any of clauses J1-J5 wherein the process includes:
   a) providing a solution or a slurry of Resmetirom in methyl THF, optionally at an elevated temperature;
   b) optionally cooling and optionally stirring
   c) optionally isolating form 14 of Resmetirom.

J7. The process according to clause J6 wherein the solution in step (a) is heated optionally to a temperature of: about 40° C. to about 95° C., about 50° C. to about 90° C., about 55° C. to about 80° C., about 60° C. to about 75° C.

J8. The process according to clause J7 wherein the solution is filtered at the elevated temperature.

J9. A process according to any of Clauses J6-J8, wherein the solution is cooled to obtain a precipitate.

J10. A process according to Clause J9, wherein the cooling is to a temperature of: −10° C. to about 20° C., about −5° C. to about 10° C., about 0° C. to about 8° C., or about 2° C. to about 5° C.

J11. A process according to any of Clauses J9-J10, wherein the mixture is stirred at the cooled temperature range for about 4 hours to about 30 hours, about 10 hours to about 25 hours, about 14 hours to about 20 hours, or about 18 hours.

J12. A process according to any of Clauses J6-J11, wherein crystalline form 14 of Resmetirom is isolated by filtering, decanting the solvent or by separating the solid by centrifugation, and optionally washing and drying.

J13. A process according to Clause J12, wherein the product is dried under reduced pressure, preferably at a temperature of: about 20° C. to about 60° C., about 30° C. to about 55° C., or about 40° C. to about 55° C., or about 45° C.

J14. A process according to any of Clauses J12-J13, wherein the drying is carried out over a period of about 30 minutes to about 10 hours to about 96 hours, about 20 hours to about 90 hours, about 40 hours to about 80 hours, about 60 hours to about 75 hours, or about 72 hours.

J15. A product obtainable by a process according to any of clauses J6-J14.

K1. A crystalline form of Resmetirom, designated form 17, which is characterized by data selected from one or more of the following:
   i) an XRPD pattern having peaks at 6.8, 8.7, 11.4, 14.5 and 29.7 degrees 2-theta±0.2 degrees 2-theta;
   ii) an XRPD pattern as depicted in FIG. 14; and combinations of these data.

K2. A crystalline product according to Clause K1, designated form 17, characterized by the XRPD pattern having peaks at 6.8, 8.7, 11.4, 14.5 and 29.7 degrees 2-theta±0.2 degrees 2-theta, and also having one, two, three or four additional peaks selected from 10.1, 15.0, 15.4, 19.7 and 20.0 degrees two theta±0.2 degrees two theta.

K3. A crystalline product according to any one of clauses K1 or K2 which is characterized by an X-ray powder diffraction pattern having peaks at 6.8, 8.7, 10.1, 11.4, 14.5, 15.0, 15.4, 19.7, 20.0 and 29.7 degrees 2-theta±0.2 degrees 2-theta.

K4. A crystalline form of Resmetirom according to any of Clauses K1-K3 which is a methyl ethyl ketone solvate.

K5. A Crystalline form of Resmetirom according to any of Clauses K1-K4, which contain about 12% to about 15% of methyl ethyl ketone by weight, or about 13 to about 14% or about 13.5% to about 13.9% by weight, or about 13.7% of methyl ethyl ketone by weight, as determined by TGA K6. A crystalline product according to any of Clauses K1-K5, which contains: no more than about 20%, no more than about 10%, no more than about 5%, no more than about 2%, no more than about 1% or about 0% of any other crystalline forms of Resmetirom.

K7. A crystalline product according to any of K1-K6, which contains: no more than about 20%, no more than about 10%, no more than about 5%, no more than about 2%, no more than about 1% or about 0% of amorphous Resmetirom.

K8. A process for preparation of form 17 of Resmetirom according to any of clauses K1-K7 wherein the process includes:

a) providing a solution or a slurry of Resmetirom in methyl ethyl ketone, optionally at an elevated temperature;

b) optionally cooling and optionally stirring c) optionally isolating form 17 of Resmetirom.

K9. The process according to clause K8 wherein the solution in step (a) is heated optionally to a temperature of: about 40° C. to about 85° C., about 50° C. to about 80° C., about 65° C. to about 75° C., or about 70° C.

K10. The process according to clause K9 wherein the solution is filtered at the elevated temperature.

K11. A process according to any of Clauses K8-K10, wherein the solution is cooled to obtain a precipitate.

K12. A process according to Clause K11, wherein the cooling is to a temperature of: −10° C. to about 20° C., about −5° C. to about 10° C., about 0° C. to about 8° C., or about 2° C. to about 5° C.

K13. A process according to any of Clauses K11-K12, wherein the mixture is stirred at the cooled temperature range for about 4 hours to about 30 hours, about 10 hours to about 25 hours, about 14 hours to about 20 hours, or about 18 hours.

K14. A process according to any of Clauses K8-K13, wherein crystalline form 17 of Resmetirom is isolated by filtering, decanting the solvent or by separating the solid by centrifugation, and optionally washing and drying.

K15. A process according to Clause K14, wherein the product is dried under reduced pressure, preferably at a temperature of: about 20° C. to about 60° C., about 30° C. to about 55° C., or about 40° C. to about 55° C., or about 45° C.

K16. A process according to any of Clauses K14-K15, wherein the drying is carried out over a period of about 30 minutes to about 28 hours, about 45 minutes to about 24 hours, about 1 hour to about 20 hours.

K17. A product obtainable by a process according to any of clauses K8-K16.

L1. A pharmaceutical composition comprising a crystalline product according to any of Clauses A1-A10, A50, B1-B10, B43, C1-C7, C42, D1-D8, D41, E1-E8, E37, F1-F10, F24, G1-G9, G23, H1-H6, H17, J145, J15, K1-K7 and K17, and at least one pharmaceutically acceptable excipient.

L2. Use of a crystalline product according to any of Clauses A1-A10, A28, A50, B1-B10, B43, C1-C7, C42, D1-D8, D41, E1-E8, E37, F1-F10, F24, G1-G9, G23, H1-H6, H17, J145, J15, K1-K7 and K17, for the preparation of a pharmaceutical composition and/or formulation, preferably wherein the pharmaceutical formulation is a tablet or a capsule.

L3. A process for preparing the pharmaceutical composition according to Clause L1, comprising combining a crystalline product according to any of Clauses A1-A10, A28, A50, B1-B10, B43, C1-C7, C42, D1-D8, D41, E1-E8, E37, F1-F10, F24, G1-G9, G23, H1-H6, H17, J145, J15, K1-K7 and K17, with at least one pharmaceutically acceptable excipient.

L4. A crystalline product according to any of Clauses A1-A10, A28, A50, B1-B10, B43, C1-C7, C42, D1-D8, D41, E1-E8, E37, F1-F10, F24, G1-G9, G23, H1-H6, H17, J145, J15, K1-K7 and K17, or a pharmaceutical composition according to Clause L1, for use as a medicament.

L5. A crystalline product according to any of Clauses A1-A10, A28, A50, B1-B10, B43, C1-C7, C42, D1-D8, D41, E1-E8, E37, F1-F10, F24, G9, G23, H1-H6, H17, J145, J15, K1-K7 and K17, or a pharmaceutical composition according to Clause L1, for use in the treatment of non-alcoholic steatohepatitis (NASH), non-alcoholic fatty liver disease (NAFLD) and/or associated dyslipidemias.

L6. A method of treating non-alcoholic steatohepatitis (NASH), non-alcoholic fatty liver disease (NAFLD) and/or associated dyslipidemias comprising administering a therapeutically effective amount of a crystalline product according to any of Clauses A1-A10, A28, A50, B1-B10, B43, C1-C7, C42, D1-D8, D41, E1-E8, E37, F1-F10, F24, G9, G23, H1-H6, H17, J145, J15, K1-K7 and K17, or a pharmaceutical composition according to Clause L1, to a subject in need of the treatment.

L7. Use of a crystalline product according to any of Clauses A1-A10, A28, A50, B1-B10, B43, C1-C7, C42, D1-D8, D41, E1-E8, E37, F1-F10, F24, G9, G23, H1-H6, H17, J145, J15, K1-K7 and K17, in the preparation of another solid state form of Resmetirom or Resmetirom salt, or Resmetirom cocrystal.

Having thus described the disclosure with reference to particular preferred embodiments and illustrative examples, those in the art can appreciate modifications to the disclosure as described and illustrated that do not depart from the spirit and scope of the disclosure as disclosed in the specification. The following examples are set forth to aid in understanding the disclosure but are not intended to, and should not be construed to limit its scope in any way.

Powder X-Ray Diffraction ("XRPD") Method

XRPD analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min. The positions of the peaks were corroborated respective to the silicon theoretical peak at 28.45 degrees two theta.

For FIG. 27: XRPD analysis was performed on Bruker powder X-Ray diffractometer model D8 ADVANCE equipped with a solid state detector. Copper radiation of 1.54060 Å was used. Scanning parameters: range: 2-40 degrees two-theta; scan mode; step size: 0.05°. The positions of the peaks were corrected respective to the silicon theoretical peak at 28.45 degrees two theta.

TGA Analysis—Mettler Toledo TGA/DSC.

Scanning Parameters:

Heating between 25-250° C.

Heating rate: 10° C./min.

Purging with 40 ml/min $N_2$ flow.

Sample weight: 7-15 mg.

Crucible: 150 μL alumina Crucible with standard aluminum lid.

Solid-State NMR

Solid-state NMR spectra were measured at 11.7 T using a Bruker Avance III HD 500 US/WB NMR spectrometer (Karlsruhe, Germany, 2013). The 13C CP/MAS NMR spectra employing cross-polarization were acquired using the standard pulse scheme at spinning frequency of 18 kHz. The recycle delay was 8 s and the cross-polarization contact time was 2 ms. The strength of spin-locking fields B1(13C) expressed in frequency units $\omega_1/2\pi=\gamma$ B1 was 64 kHz.

EXAMPLES

Preparation of Starting Materials

Resmetirom can be prepared according to methods known from the literature, for example according to the disclosure in International publication no. WO 2007/009913.

Example 1: Purification of Resmetirom

Resmetirom crude (4 grams, LT about 94% purity; by TLC (Hexane:Chloroform:Ethanol:Acetic acid, 40:40:20:2), Methanol (480 ml, 120V) and 2-methoxy ethanol (40 ml, 10 V) were added to 1 L reactor at room temperature to give slurry. The slurry was heated to 75° C. to obtain clear red-orange solution. Next, active carbon (1.6 grams) was added to the hot solution. After stirring at 75° C. for 1 hour, the active carbon was removed by hot filtration under vacuum to give an off-white solution, which was evaporated under reduced pressure. The obtained precipitate was dried in a vacuum oven at 45° C. during 2 days to give pure Resmetirom (NLT 100% purity by TLC; about 90% yield).

Example 1A: Purification of Resmetirom

Resmetirom crude (24 grams, LT about 94% purity; by TLC (Hexane:Chloroform:Ethanol:Acetic acid, 40:40:20:2), Methanol (2.88 L, 120V) were added to 3 L reactor at room temperature to give a slurry. The slurry was heated to reflux to obtain clear red-orange solution. Next, active carbon (10.8 grams) was added to the hot solution. After stirring at reflux for 1 hour, the active carbon was removed by hot filtration under vacuum to give an off-white solution, which was evaporated under reduced pressure. The obtained precipitate was dried in a vacuum oven at 45° C. during 2 days to give pure Resmetirom (NLT 100% purity by TLC; about 90% yield).

Example 2: Preparation of Resmetirom Form 2

Procedure A

Methyl isopropyl ketone (MIPK) (1.25 ml, 50V) was added to Resmetirom (25 mg, 0.06 mmol) to obtain a slurry. The slurry was heated to 80° C. and magnetically stirred at 80° C. over a period of 30 minutes to obtain complete dissolution, followed by a hot mechanical filtration. Next, diethyl ether as anti-solvent (5.6 ml) was added drop-wise to the stirred clear solution at 80° C. The obtained clear solution was stirred at 80° C. during 1 hour and then cooled to room temperature. Next, the solution was magnetically stirred at RT over 48 hours to obtain a solid precipitate. The solid was then separated by centrifuge and analyzed by X-ray powder diffraction. The XRPD pattern is presented in FIG. 1.

Procedure B

Methyl isopropyl ketone (MIPK) (4.0 ml, 20V) was added to Resmetirom (as can be prepared by purification according to Example 1) (200 mg, and 0.46 mmol) to give a slurry. The obtained slurry was heated to 80° C. and stirred at 80° C. temperature for a period of 48 hours. Then the slurry was cooled to room temperature and separated by centrifuge. Next, the obtained solid was dried in a vacuum oven at 25° C. during 2 hours and was analyzed by X-ray powder diffraction and identified as Resmetirom crystal Form 2.

Example 3: Preparation of Resmetirom Form 3

Procedure A

Dioxane (1.7 ml, 57V) was added to Resmetirom (30 mg, 0.07 mmol) to obtain a slurry. The slurry was heated to 70° C. and magnetically stirred at 70° C. for a period of 30 minutes to obtain complete dissolution, followed by a hot mechanical filtration. Next, diethyl ether as anti-solvent (6.8 ml) was added drop-wise to the stirred clear solution at 80° C. to obtain a solid precipitate. The obtained slurry was magnetically stirred at 80° C. during 1 hour and then cooled to room temperature with stirring. Next, the obtained slurry was magnetically stirred at room temperature during 18 hours. The solid was then separated by centrifuge and analyzed by XRPD. The obtained XRPD pattern is presented in FIG. 2.

Procedure B

Dioxane (2.0 ml, 10V) was added to Resmetirom (as can be prepared by purification of Resmetirom crude according to Example 1), (200 mg, and 0.46 mmol) to give a slurry. The obtained slurry was heated to 80° C. and magnetically stirred at 80° C. for a period of 48 hours. Then, the slurry was cooled to room temperature and separated by centrifuge. The obtained solid was dried in a vacuum oven at 25° C. for 2 hours. The solid was analyzed by X-ray powder diffraction and identified as Resmetirom crystal Form 3.

Example 4: Preparation of Resmetirom Form 4

Procedure A

Anisole (4.0 ml, 20V) was added to Resmetirom (as can be prepared by purification of Resmetirom crude according to Example 1) (200 mg, and 0.46 mmol) to obtain a slurry. The slurry was heated to 80° C. and stirred at 80° C. for a period of 48 hours. Then, the slurry was separated by centrifuge. The obtained solid was analyzed by X-ray powder diffraction and the obtained XRPD pattern is presented in FIG. 3.

Example 5: Preparation of Resmetirom Form 6

Procedure A

N,N-Dimethylformamide (DMF) (1.3 ml, 4.3V) was added to Resmetirom (30 mg, 0.07 mmol) to obtain a slurry. The slurry was heated to 80° C. and magnetically stirred at 80° C. for a period of 30 minutes to obtain complete dissolution, followed by a hot mechanical filtration. Next, water as anti-solvent (2.6 ml) was added drop-wise to the stirred clear solution at 80° C. to obtain a solid precipitate. The obtained slurry was stirred at 80° C. during 1 hour and cooled to room temperature. Next, the slurry was magnetically stirred at room temperature during 18 hours. The solid was then separated by centrifuge and was dried in a vacuum oven at 25° C. for 18 hours. The obtained solid was analyzed by X-ray powder diffraction and the obtained XRPD pattern is presented in FIG. 4.

Example 6: Preparation of Resmetirom Form 7

Procedure A

Acetyl acetone (0.85 ml, 30V) was added to Resmetirom (30 mg, 0.07 mmol) to obtain a slurry. The slurry was heated to 80° C. and magnetically stirred at 80° C. over a period of 30 minutes to obtain complete dissolution, followed by a hot mechanical filtration. Next, hexane as anti-solvent (2.55 ml) was added drop-wise to the stirred clear solution at 80° C. to obtain a solid precipitate. The obtained slurry was stirred at 80° C. during 1 hour and cooled to room temperature. Next, the slurry was magnetically stirred at room temperature during 18 hours. The solid was then separated by centrifuge analyzed by X-ray powder diffraction and the obtained XRPD pattern is presented in FIG. 5.
Procedure B Acetyl acetone (4.0 ml, 20V) was added to Resmetirom (as can be prepared by purification of Resmetirom crude according to Example 1) (200 mg, and 0.46 mmol) to give a slurry. The obtained slurry was stirred at room temperature over a period of 48 hours. Then, the slurry was separated by centrifuge and dried in vacuum oven at 25° C. during 2 hours. The solid was analyzed by XRPD and identified as Resmetirom Form 7.

Example 7: Preparation of Resmetirom Form 8

Procedure A

Acetyl acetone (0.85 ml, 30V) was added to Resmetirom (30 mg, 0.07 mmol) to obtain a slurry. The slurry was heated to 80° C. and was magnetically stirred at 80° C. over a period of 30 minutes to obtain complete dissolution, followed by a hot mechanical filtration. Next, propionitrile as anti-solvent (3.4 ml) was added drop-wise to the stirred clear solution at 80° C. to obtain a solid precipitate. The obtained slurry was magnetically stirred at 80° C. during 1 hour and then cooled to room temperature. Next, the obtained slurry was magnetically stirred at room temperature during 18 hours. The solid was then separated by centrifuge and analyzed by X-ray powder diffraction and identified as Form 8.
Procedure B Propionitrile (0.80 ml, 20V) was added to Resmetirom (as can be prepared by purification of Resmetirom crude according to Example 1) (40 mg, and 0.09 mmol) to give a slurry. The obtained slurry was heated to 80° C. and stirred at 80° C. over a period of 48 hours. Then, the slurry was left to cool to room temperature, separated by centrifuge and dried in vacuum oven at 25° C. during 2 hours. The solid was analyzed by X-ray powder diffraction and the obtained XRPD pattern is presented in FIG. 6.

Example 8: Preparation of Resmetirom Form 9

Procedure A

Nitrobenzene (2.0 ml, 10V) was added to Resmetirom (as can be prepared purification of Resmetirom crude according to Example 1) (200 mg, and 0.46 mmol) to give a slurry. The obtained slurry was heated to 80° C. and stirred at 80° C. over a period of 48 hours. Then, the slurry was left to cool to room temperature, separated by centrifuge and dried in vacuum oven at 25° C. during 2 hours. The solid was analyzed by X-ray powder diffraction and the obtained XRPD pattern is presented in FIG. 7.

Example 9: Preparation of Resmetirom Form 10

Procedure A

Di(ethylene glycol)ethyl ether (2.0 ml, 10V) was added to Resmetirom (as can be prepared purification of Resmetirom crude according to Example 1) (200 mg, and 0.46 mmol) to give a slurry. The obtained slurry was stirred at room temperature over a period of 48 hours. Then, the slurry was separated by centrifuge, analyzed by X-ray powder diffraction and the obtained XRPD pattern is presented in FIG. 8.

Example 10: Preparation of Resmetirom Form 11

Procedure A 1,3-Dioxolane (1 ml, 33.3V) was added to Resmetirom (30 mg, 0.07 mmol) and stirred at room temperature to give a clear solution. The clear solution was mechanically filtered and was left for 4 days for slow evaporation at room temperature. The obtained solid was analyzed by X-ray powder diffraction and the obtained XRPD pattern is presented in FIG. 9.

Example 11: Preparation of Resmetirom Form 13

Procedure A

Methyl ethyl ketone (3.33 ml, 33.3V) was added to Resmetirom (100 mg, 0.23 mmol) to obtain a slurry. The slurry was heated to 60° C. and magnetically stirred at 60° C. over a period of 30 minutes to obtain a clear solution, followed by a hot mechanical filtration. Next, dichloroethane as anti-solvent (10 ml) was added drop-wise to the stirred clear solution at 60° C. to obtain a solid precipitate. The obtained slurry was stirred at 60° C. during 1 hour and cooled to room temperature. Next, the slurry was magnetically stirred at room temperature during 18 hours. The solid was then separated by centrifuge and dried in vacuum oven at 25° C. during 2 hours. The solid was analyzed by X-ray powder diffraction and the obtained XRPD pattern is presented in FIG. 10.
Procedure B 2-methoxy ethanol (0.15 ml, 5V) was added to Resmetirom (30 mg, 0.07 mmol) to obtain a slurry. The slurry was heated to 80° C. and magnetically stirred at 80° C. over a period of 30 minutes to obtain a clear solution, followed by a hot mechanical filtration. Next, dichloroethane as anti-solvent (0.6 ml) was added drop-wise to the stirred clear solution at 80° C. to obtain a solid precipitate. The obtained slurry was stirred at 80° C. during 1 hour and cooled to room temperature. Next, the slurry was magnetically stirred at room temperature during 18 hours and was then separated by centrifuge. The solid was analyzed by X-ray powder diffraction and identified as Resmetirom crystal Form 13.

Example 12: Preparation of Resmetirom Form 14

Procedure A

Methyl tetrahydrofuran (3.3 ml, 10V) was added to Resmetirom (prepared according to Example 1) (100 mg, and 0.23 mmol) to give a slurry. The obtained slurry was stirred at 75° C. for 30 minutes to full dissolution of the solid, followed by a hot mechanical filtration. Next, the filtered clear solution was magnetically stirred at 4° C. during 18 hours to obtain a solid precipitate. The solid was then separated by centrifuge and dried in vacuum oven at 25° C. for 3 hours. The solid was analyzed by X-ray powder diffraction and the obtained pattern is presented in FIG. 11.
Procedure B Methyl tetrahydrofuran (5 ml, 10V) was added to Resmetirom (prepared according to Example 1) (500 mg, and 0.15 mmol) to give a slurry. The obtained slurry was heated to 60° C. and magnetically stirred at this temperature for 48 hours. Then, the slurry was cooled to room temperature and separated by centrifuge. The solid was dried in vacuum oven at 25° C. for 3 hours. The solid was analyzed by X-ray powder diffraction and identified as Resmetirom crystal Form 14.

Example 13: Preparation of Resmetirom Form 15

Procedure A

Propionic acid (15 ml, 50V) was added to Resmetirom (300 mg, 0.7 mmol) to obtain a slurry. The slurry was magnetically stirred at 80° C. over a period of 30 minutes to obtain a clear solution, followed by a hot mechanical filtration. Next, the filtered clear solution was magnetically stirred at 4° C. for 72 hours to obtain a solid precipitate. The solid was then separated by centrifuge and dried in vacuum oven at 25° C. during 3 hours. The solid was analyzed by X-ray powder diffraction and the obtained XRPD pattern is presented in FIG. 12.

Example 14: Preparation of Resmetirom Form 16

Procedure A

Propionic acid (15 ml, 50V) was added to Resmetirom (300 mg, 0.7 mmol) to obtain a slurry. The slurry was magnetically stirred at 80° C. over a period of 30 minutes to obtain clear solution, followed by a hot mechanical filtration. Next, the filtered clear solution was magnetically stirred at 4° C. during 72 hours to obtain a solid precipitation. Next, the saturated solution was separated by centrifuge from the solid and then was concentrated by slow evaporation of the solvent at 80° C. during 48 hours to give a solid. The solid was analyzed by X-ray powder diffraction and the obtained XRPD pattern is presented in FIG. 13.

Example 15: Preparation of Resmetirom Form 17

Procedure A

Methyl ethyl ketone (2 ml, 20V) was added to Resmetirom (100 mg, 0.23 mmol) to obtain a slurry. The slurry was magnetically stirred at 72° C. over a period of 30 minutes to obtain a clear solution, followed by a hot mechanical filtration. Next, the filtered clear solution was magnetically stirred at 4° C. during 18 h to obtain a solid precipitate. The solid was then separated by centrifuge and dried in vacuum oven at 25° C. during 2 hours. The solid was analyzed by X-ray powder diffraction and the obtained XRPD pattern is presented in FIG. 14.

Procedure B

Methyl ethyl ketone (20 ml, 20V) was added to Resmetirom (1000 mg, 2.3 mmol) to obtain a slurry. The slurry was magnetically stirred at 72° C. over a period of 30 minutes to obtain a clear solution, followed by a hot mechanical filtration. Next, the filtered clear solution was concentrated by rotor vapor to give a solid. The solid was dried in vacuum oven at 25° C. during 18 hours. The solid was analyzed by X-ray powder diffraction and identified as form 17.

Example 16: Preparation of Resmetirom Form 19

Procedure A

Methyl ethyl ketone (2.0 ml, 20V) was added to Resmetirom (100 mg, 0.23 mmol) to obtain a slurry. The slurry was magnetically stirred at 70° C. over a period of 30 minutes to obtain a clear solution, followed by a hot mechanical filtration. Next, toluene as anti-solvent (8 ml) was added drop-wise to the stirred clear solution at 70° C. to obtain a solid precipitate. The obtained slurry was stirred at 70° C. during 1 hour and cooled to room temperature. Next, the slurry was magnetically stirred at room temperature during 18 hours. The solid was then separated by centrifuge and dried in vacuum oven at 25° C. during 3 hours. The solid was analyzed by X-ray powder diffraction and the obtained XRPD pattern is presented in FIG. 15.

Procedure B

Dimethylacetamide (DMAc) (2.5 ml, 5V) was added to Resmetirom (500 mg, 1.15 mmol) to obtain a slurry. The slurry was heated to 80° C. and magnetically stirred at 80° C. over a period of 30 minutes to obtain complete dissolution, followed by a hot mechanical filtration. Next, isopropyl alcohol (IPA) as anti-solvent (10 ml) was added drop-wise to the stirred clear solution at 80° C. The obtained clear solution was stirred at 80° C. during 1 hour and then cooled to room temperature. Next, the solution was magnetically stirred at RT over 18 hours to obtain a solid precipitate. The solid was then separated by centrifuge, dried in vacuum oven at 25° C. during 18 hours.

Toluene (2.0 ml, 20V) was added to Resmetirom obtained above (100 mg, and 0.23 mmol) to give a slurry. The obtained slurry was stirred at 80° C. over a period of 18 hours. Then, the slurry was cooled to room temperature, filtered by centrifuge, dried in vacuum oven at 45° C. during 18 hours and was analyzed by X-ray powder diffraction and identified as Resmetirom crystal Form 19.

Example 17: Preparation of Resmetirom Form 20

Procedure A

Acetonitrile (66 ml, 132V) was added to Resmetirom, prepared according to Example 1, (500 mg, 1.15 mmol) to obtain a slurry. The slurry was magnetically stirred at 80° C. over a period of 30 minutes to obtain a cloudy solution, followed by a hot mechanical filtration. Next, the filtered clear solution was magnetically stirred at room temperature during 18 h to obtain a solid precipitate. The solid was then separated by Buchner and dried in vacuum oven at 45° C. during 72 hours. The solid was analyzed by X-ray powder diffraction and the obtained XRPD pattern is presented in FIG. 16.

Example 18: Preparation of Resmetirom Form 21

Procedure A

Acetonitrile (10.8 ml, 120V) was added to Resmetirom (100 mg, 0.23 mmol) to obtain slurry. The slurry was magnetically stirred at 80° C. over a period of 30 minutes to obtain clear solution, followed by a hot mechanical filtration. Next, the filtered clear solution was concentrated by rotor vapor to give a solid. The solid was analyzed by X-ray powder diffraction and the obtained XRPD pattern is presented in FIG. 17.

Example 19: Preparation of Resmetirom Form 22

Procedure A

Ethylene glycol (10 ml, 20V) was added to Resmetirom (prepared according the Example 1A) (500 mg, 1.15 mmol) to give a slurry. The obtained slurry was stirred at room temperature during 48 hours. Next, the obtained solid was separated by centrifuge and dried in vacuum oven at 45° C. during 18 hours. The solid was analyzed by X-ray powder diffraction and the obtained XRPD pattern is presented in FIG. 18.

Resmetirom Forms 2, 3, 5 and 20 may also be used for preparation of Resmetirom Form 22.

Example 20: Preparation of Resmetirom N-Methylmorpholine Salt Form R1-A

Procedure A

N-methylmorpholine [4-methylmorpholine] (4.0 ml, 20V) was added to Resmetirom prepared according to Example 1A (200 mg, 0.26 mmol) to obtain a slurry. The slurry was magnetically stirred at room temperature over a period of 48 hours. Next the solid was separated by centrifuge and dried in vacuum oven at 45° C. for 18 hours and was then analyzed by X-ray powder diffraction and the obtained XRPD pattern is presented in FIG. 19.

Example 21: Preparation of Resmetirom Piperazine Salt Form R2-A

Procedure A 2-methoxy ethanol (4.2 ml, 35.3V) was added to Piperazine (119 mg, 1.38 mmol) to give a slurry. The slurry was magnetically stirred at 80° C. over a period of 30 minutes to obtain a clear solution, followed by a hot mechanical filtration. Then, Resmetirom (600 mg, 1.38 mmol) was added to the magnetically stirring clear solution at 80° C. to give slurry. Next, the slurry was magnetically stirred at 80° C. to give a clear solution and after 15 minutes a solid precipitation occurred. Next, obtained slurry was cooled to room temperature and then magnetically stirred at room temperature during 18 hours. Then the obtained solid was separated by centrifuge, dried in vacuum oven at 45° C. during 18 hours and analyzed by X-ray powder diffraction and the obtained XRPD pattern is presented in FIG. 20.

Procedure B 2-methoxy ethanol (0.42 ml, 70V) was added to Piperazine (6 mg, 0.07 mmol) to give a slurry. The slurry was magnetically stirred at 80° C. over a period of 30 minutes to obtain a clear solution, followed by a hot mechanical filtration. Then, the obtained clear solution was placed in a 4 ml vial. Next, in another 4 ml vial, 2-methoxy ethanol (0.25 ml, 8.3V) was added to Resmetirom (30 mg, 0.07 mmol) to give a slurry. The slurry was magnetically stirred at 80° C. over a period of 30 minutes to obtain a clear solution, followed by a hot mechanical filtration. Then, the Resmetirom hot solution was added to 4 ml vial that contains the Piperazine hot solution and the reaction was magnetically stirred at 80° C. during 15 minutes. Then, the clear solution was concentrated in vacuum oven at 45° C. during 24 hours. The obtained solid was analyzed by X-ray powder diffraction and identified as Resmetirom piperazine salt form R2-A.

Example 22: Preparation of Resmetirom:L-Proline Form R3-A

Procedure A 2-methoxy ethanol (3.5 ml, 26 Vol) was added to L-proline (132 mg, 1.15 mmol) to give a slurry. The slurry was magnetically stirred at 80° C. over a period of 30 minutes to obtain a clear solution, followed by a hot mechanical filtration. Then, Resmetirom (500 mg, 1.15 mmol) was added to the magnetically stirred clear hot solution at 80° C. to obtain a slurry. Next, the slurry was magnetically stirred at 80° C. to give a clear solution and after 15 minutes precipitation occurred. Next, the obtained slurry was cooled to room temperature and was magnetically stirred during 18 hours. Then the solid was filtered by Buchner and dried in vacuum oven at 45° C. during 18 hours. The obtained solid was analyzed by X-ray powder diffraction and the obtained XRPD pattern is presented in FIG. 21.

Procedure B 2-methoxy ethanol (0.66 ml, 55V) was added to L-proline (12 mg, 0.11 mmol) to give a slurry. The slurry was magnetically stirred at 80° C. over a period of 30 minutes to obtain clear solution, followed by a hot mechanical filtration. Then, the obtained clear solution was placed in a 4 ml vial. Next, in another 4 ml vial, 2-methoxy ethanol (0.21 ml, 7V) was added to Resmetirom (30 mg, 0.07 mmol) to give a slurry. The slurry was magnetically stirred at 80° C. over a period of 30 minutes to obtain clear solution, followed by a hot mechanical filtration. Then, the Resmetirom hot solution was added to the 4 ml vial that contained the L-Proline hot solution and the reaction was magnetically stirred at 80° C. during 15 minutes. Then, the clear solution was concentrated by rotor vapor. The obtained solid was analyzed by X-ray powder diffraction and identified as Resmetirom L-proline salt form R3-A.

Example 23: Preparation of Resmetirom Benzathine Salt Form R4-A

Procedure A

Ethanol (45 ml, 75V) was added to Resmetirom (0.6 grams, 1.38 mmol) to give a slurry. The obtained slurry was heated to 75° C. and magnetically stirred at this temperature during 30 minutes to obtain a clear solution, followed by a hot mechanical filtration. Then, benzathine (0.663 ml, 2.76 mmol) was added dropwise to the filtrated solution at 75° C. while magnetically stirred. Next, the obtained clear mixture was cooled to room temperature to give slurry and was stirred at room temperature during 18 hours. The obtained solid was filtered by Buchner and then dried in vacuum oven at 45° C. during 18 hours. The obtained solid was analyzed by X-ray powder diffraction and the obtained XRPD pattern is presented in FIG. 22.

Example 24: Preparation of Resmetirom: Nicotinamide Form RC1-A

Procedure A

Resmetirom (prepared by purification of Resmetirom crude according to example 1) (200 mg, 0.46 mmol) was grinded by mortar and pestle with Nicotinamide (56.2 mg, 0.46 mmol, 1 eq.) during 1 minute. Dichloromethane was added to 50 mg of grinding mixture of Resmetirom and Nicotinamide to give slurry. The obtained slurry was seeded with 0.1-0.5% of Resmetirom:nicotinamide Form RC1-A (prepared according to procedure B or C) and was magnetically stirred at room temperature during 18 hours. Then, the solid was separated by centrifuge and dried in vacuum oven at 45° C. during 18 hours. The obtained solid was analyzed by X-ray powder diffraction and the XRPD pattern is presented in FIG. 23.

Procedure B 2-methoxy ethanol (0.25 ml, 5V) was added to Resmetirom (prepared by purification of Resmetirom crude according to example 1) (50 mg, 0.115 mmol) to give slurry. The obtained slurry was stirred at 80° C. during 30 minutes to full dissolution of the solid. Next, Nicotinamide (14.05 mg, 0.115 mmol, 1 eq.) was added to obtained hot clear solution to give slurry. Then, the obtained slurry was magnetically stirred at 80° C., for 30 min. to full dissolution of the solid. Next, the above mixture was dried in a vacuum oven at 45° C. for 18 hours to obtain yellow solid. Then, Dichloromethane (0.512 ml, 8V) was added to give slurry. The obtained slurry was magnetically stirred at 25° C. during 18 hours. Then the solid separated by centrifuge and dried in vacuum oven at 45° C. during 18 hours. The solid was analyzed by X-ray powder diffraction and characterized as Resmetirom: nicotinamide Form RC1-A.

Procedure C

Resmetirom (prepared by purification of Resmetirom crude according to example 1) (50 mg, 0.115 mmol) was grinded by mortar and pestle with Nicotinamide (14.05 mg, 0.115 mmol, 1 eq.) during 1 minute. The obtained solids mixture was heated in 1.7 ml glass vial at 140° C. (10° C. higher than the melting point of co-former) during 2 hours. Then, the vial was cooled to 120° and heated at this temperature during 1 hour. Next, the vial was cooled to room temperature. The obtained solid was analyzed and characterized as Resmetirom:nicotinamide Form RC1-A.

Procedure D

Dichloromethane (0.48 ml, 8V) was added to Resmetirom Form 14 (methyltetrahydrofuran solvate) (50 mg, 0.115 mmol) to give slurry. Next, Nicotinamide (14 mg, 0.115 mmol, 1.0 eq.) was added to the obtained slurry. Then, the obtained slurry was magnetically stirred at room temperature, and then was seeded with 0.1-0.5% of Resmetirom Form RC1-A. Next, the slurry was magnetically stirred at room temperature during 4 days. The precipitate was separated by centrifuge and then was dried in vacuum oven at 45° C. for 18 hours. The obtained solid was analyzed by X-ray powder diffraction and identified as Resmetirom Nicotinamide crystal Form RC1-A.

Procedure E

Dichloromethane (0.48 ml, 8V) was added to Resmetirom Form 17 (methylethyl ketone solvate) (50 mg, 0.115 mmol) to give slurry. Next, Nicotinamide (14 mg, 0.115 mmol, 1.0 eq.) was added to the obtained slurry. Then, the obtained slurry was magnetically stirred at room temperature, and then was seeded with 0.1-0.5% of Resmetirom Form RC1-A. Next, the slurry was magnetically stirred at room temperature during 3 days. The precipitate was separated by centrifuge and then was dried in vacuum oven at 45° C. for 18 hours. The obtained solid was analyzed by X-ray powder diffraction and identified as Resmetirom Nicotinamide crystal Form RC1-A.

Example 25: Preparation of Resmetirom:Caffeine Form RC2-A

Procedure A 2-methoxy ethanol (0.2 ml, 6.7V) was added to Resmetirom (prepared by purification of Resmetirom crude according to example 1) (30 mg, 0.07 mmol) to give a slurry. The obtained slurry was stirred at 80° C. during 30 minutes to full dissolution of the solid. Next, Caffeine (13.4 mg, 0.07 mmol, 1 eq.) was added to obtained hot clear solution to give a slurry. Then, ethanol (0.2 ml, 6.7V) was added to the obtained slurry and was magnetically stirred at 80° C., for 30 minutes to full dissolution of the solid. The mixture was dried in a vacuum oven at 45° C. for 18 hours, to obtain yellow solid. Then, isopropanol (0.18 ml, 4V) was added to give slurry. The obtained slurry was magnetically stirred at 25° C. during 18 hours. Then the solid separated by centrifuge and dried in vacuum oven at 45° C. during 18 hours. The solid was analyzed by X-ray powder diffraction and the XRPD pattern is presented in FIG. 24.

Procedure B

Iso-propyl alcohol (0.45 ml, 6V) was added to Resmetirom Form 14 (methyltetrahydrofuran solvate) (50 mg, 0.115 mmol) to give slurry. Next, Caffeine (24.2 mg, 0.126 mmol, 1.1 eq.) was added to the obtained slurry. Then, the obtained slurry was magnetically stirred at room temperature, and then was seeded with 0.1-0.5% of Resmetirom Form RC2-A. Next, the slurry was magnetically stirred at room temperature during 4 days. The precipitate was separated by centrifuge and then was dried in vacuum oven at 45° C. for 18 hours. The obtained solid was analyzed by X-ray powder diffraction and identified as Caffeine Resmetirom crystal Form RC2-A.

Procedure C

Iso-propyl alcohol (0.45 ml, 6V) was added to Resmetirom Form 17 (methylethyl ketone solvate) (50 mg, 0.115 mmol) to give slurry. Next, Caffeine (24.2 mg, 0.126 mmol, 1.1 eq.) was added to the obtained slurry. Then, the obtained slurry was magnetically stirred at room temperature, and then was seeded with 0.1-0.5% of Resmetirom Form RC2-A. Next, the slurry was magnetically stirred at room temperature during 3 days. The precipitate was separated by centrifuge and then was dried in vacuum oven at 45° C. for 18 hours. The obtained solid was analyzed by X-ray powder diffraction and identified as Resmetirom Caffeine crystal Form RC2-A.

Example 26: Preparation of Resmetirom:Caffeine Form RC2-B

Procedure A 2-methoxy ethanol (0.2 ml, 6.7V) was added to Resmetirom (prepared by purification of Resmetirom crude according to example 1) (30 mg, 0.07 mmol) to give a slurry. The obtained slurry was stirred at 80° C. during 30 minutes to full dissolution of the solid. Next, Caffeine (13.4 mg, 0.07 mmol, 1 eq.) was added to obtained hot clear solution to give slurry. Then, ethanol (0.2 ml, 6.7V) was added to the obtained slurry and was magnetically stirred at 80° C., for 30 minutes to full dissolution of the solid. Next, the above mixture was dried in a vacuum oven at 45° C. for 18 hours, to obtain yellow solid. Then, toluene (0.18 ml, 4V) was added to give slurry. The obtained slurry was magnetically stirred at 25° C. during 18 hours. Then the solid separated by centrifuge and dried in vacuum oven at 45° C. during 18 hours. The solid was analyzed by X-ray powder diffraction and the XRPD pattern is presented in FIG. 25.

Procedure B

Resmetirom (prepared by purification of Resmetirom crude according to example 1) (200 mg, 0.46 mmol) was grinded by mortar and pestle with Caffeine (89 mg, 0.46 mmol, 1 eq.) during 1 minute. Toluene (4 Vol) was added to 250 mg of grinded mixture of Resmetirom and Caffeine to give a slurry. The obtained slurry was seeded with 0.1-0.5% of Resmetirom:Caffeine Form RC2-B (prepared according to procedure example 26, procedure A and was magnetically stirred at 25° C. during 48 hours. Then, the solid was separated by centrifuge and dried in vacuum oven at 45° C. during 72 hours. The obtained solid was analyzed by X-ray powder diffraction and identified as Form RC2-B.

Procedure C

Toluene (0.30 ml, 4V) was added to Resmetirom Form 14 (methyltetrahydrofuran solvate) (50 mg, 0.115 mmol) to give slurry. Next, Caffeine (24.2 mg, 0.126 mmol, 1.1 eq.) was added to the obtained slurry. Then, the obtained slurry was magnetically stirred at room temperature, and then was seeded with 0.1-0.5% of Resmetirom Form RC2-B. Next, the slurry was magnetically stirred at room temperature during 4 days. The precipitate was separated by centrifuge and then was dried in vacuum oven at 45° C. for 18 hours. The obtained solid was analyzed by X-ray powder diffraction and identified as Resmetirom Caffeine crystal Form RC2-B.

Procedure D

Toluene (0.30 ml, 4V) was added to Resmetirom Form 17 (methylethyl ketone solvate) (50 mg, 0.115 mmol) to give slurry. Next, Caffeine (24.2 mg, 0.126 mmol, 1.1 eq.) was added to the obtained slurry. Then, the obtained slurry was magnetically stirred at room temperature, and then was seeded with 0.1-0.5% of Resmetirom Form RC2-B. Next, the slurry was magnetically stirred at room temperature during 3 days. The precipitate was separated by centrifuge and then was dried in vacuum oven at 45° C. for 18 hours. The obtained solid was analyzed by X-ray powder diffraction and identified as Resmetirom Caffeine crystal Form RC2-B.

Example 27: Preparation of Resmetirom:
2-Picolinic Acid Form RC3-A

Procedure A 2-methoxy ethanol (0.375 ml, 7.5V) was added to Resmetirom (prepared by purification of Resmetirom crude according to example 1) (50 mg, 0.115 mmol) to give a slurry. The obtained slurry was stirred at 80° C. during 30 minutes to full dissolution of the solid. Next, 2-picolinic acid (14.6 mg, 0.115 mmol, 1 eq.) was added to obtained hot clear solution to give a slurry. Then, the obtained slurry was magnetically stirred at 80° C., for 30 minutes to full dissolution of the solid. Next, the above mixture was dried in a vacuum oven at 45° C. for 18 hours, to obtain yellow solid. The solid was analyzed by X-ray powder diffraction and the XRPD pattern is presented in FIG. 26.

Procedure B

Dichloromethane (0.5 ml, 8V) was added to Resmetirom Form 14 (methyltetrahydrofuran solvate) (50 mg, 0.115 mmol) to give slurry. Next, 2-picolinic acid (15.62 mg, 0.126 mmol, 1.1 eq.) was added to the obtained slurry. Then, the obtained slurry was magnetically stirred at room temperature, and then was seeded with 0.1-0.5% of Resmetirom Form RC3-A. Next, the slurry was magnetically stirred at room temperature during 4 days. The precipitate was separated by centrifuge and then was dried in vacuum oven at 45° C. for 18 hours. The obtained solid was analyzed by X-ray powder diffraction and identified as Resmetirom 2-picolinic acid crystal Form RC3-A.

Procedure C

Dichloromethane (0.5 ml, 8V) was added to Resmetirom Form 17 (methyltetrahydrofuran solvate) (50 mg, 0.115 mmol) to give slurry. Next, 2-picolinic acid (15.62 mg, 0.126 mmol, 1.1 eq.) was added to the obtained slurry. Then, the obtained slurry was magnetically stirred at room temperature, and then was seeded with 0.1-0.5% of Resmetirom Form RC3-A. Next, the slurry was magnetically stirred at room temperature during 3 days. The precipitate was separated by centrifuge and then was dried in a vacuum oven at 45° C. for 18 hours. The obtained solid was analyzed by X-ray powder diffraction and identified as Resmetirom 2-picolinic acid crystal Form RC3-A.

Example 28: Preparation of Resmetirom:Urea Form
RC4-A

Procedure A

Resmetirom (as can be prepared purification of Resmetirom crude according to example 1) (100 mg, 0.23 mmol) and Urea (14 mg, 0.23 mmol) were dissolved in 2-methoxy ethanol (0.57 ml, 5.7 Vol) at 80° C. during 30 minutes. The obtained solution was dried in vacuum oven at 50° C. for 18 hours to give a solid and then was dried in vacuum oven at 80° C. for 18 hour. The obtained solid was characterized by X-ray powder diffraction as Resmetirom Urea crystal Form RC4-A (FIG. 27).

Procedure B

Dichloromethane (0.48 ml, 8V) was added to Resmetirom Form 14 (Me-THF solvate) (50 mg, 0.115 mmol) to give slurry. Next, Urea (7.7 mg, 0.128 mmol, 1.1 eq.) was added to obtained slurry. Then, the obtained slurry was magnetically stirred at room temperature, and then was seeded with 0.1-0.5% of Resmetirom Form RC4-A. The slurry was magnetically stirred at room temperature during 4 days. The precipitate was separated by centrifuge and then was dried in vacuum oven at 45° C. for 18 hours. The obtained solid was analyzed by X-ray powder diffraction and identified as Resmetirom Urea crystal Form RC4-A.

Procedure C

Dichloromethane (0.46 ml, 8V) was added to Resmetirom Form 17 (methylethyl ketone solvate) (50 mg, 0.115 mmol) to give slurry. Next, Urea (7.7 mg, 0.128 mmol, 1.1 eq.) was added to the obtained slurry. Then, the obtained slurry was magnetically stirred at room temperature, and was seeded with 0.1-0.5% of Resmetirom Form RC4-A. Next, this slurry was magnetically stirred at room temperature during 3 days. The precipitate was separated by centrifuge and then was dried in vacuum oven at 45° C. for 18 hours. The obtained solid was analyzed by X-ray powder diffraction and identified as Resmetirom Urea crystal Form RC4-A.

The invention claimed is:

1. Crystalline Resmetirom: caffeine.

2. The crystalline Resmetirom: caffeine according to claim 1, which is a co-crystal.

3. The crystalline Resmetirom: caffeine according to claim 1, which is a salt.

4. The crystalline Resmetirom: caffeine according to claim 1, designated form RC2-A, which is characterized by data selected from one or more of the following:

i) an XRPD pattern having peaks at 6.0, 6.8, 10.4, 11.2 and 16.4 degrees 2-theta±0.2 degrees 2-theta;

ii) an XRPD pattern as depicted in FIG. 24;

iii) a solid state $^{13}$C NMR spectrum with characteristic peaks at 139.5, 118.8, 106.7, 34.0 and 29.6 ppm=0.2 ppm;

iv) a solid state $^{13}$C NMR spectrum having the following chemical shift absolute differences from reference peak at 161.0 ppm±1 ppm: 21.4, 42.2, 54.3, 127.0 and 131.4 ppm=0.1 ppm;

v) a solid state $^{13}$C NMR spectrum substantially as depicted in FIG. 34, 35 or 36; and vi) combinations of these data.

5. The crystalline Resmetirom: caffeine according to claim 4, designated form RC2-A, characterized by the XRPD pattern having peaks at 6.0, 6.8, 10.4, 11.2 and 16.4 degrees 2-theta±0.2 degrees 2-theta, and also having one, two, three or four additional peaks selected from 14.6, 15.6, 17.8, 19.5 and 26.9 degrees two theta±0.2 degrees two theta.

6. The crystalline Resmetirom: caffeine according to claim 4, which is characterized by an X-ray powder diffraction pattern having peaks at 6.0, 6.8, 10.4, 11.2, 14.6, 15.6, 16.4, 17.8, 19.5 and 26.9 degrees 2-theta±0.2 degrees 2-theta.

7. The crystalline Resmetirom: caffeine according to claim 4, wherein the molar ratio of Resmetirom and caffeine is 1:1.

8. The crystalline Resmetirom: caffeine according to claim 4, which is an anhydrous form.

9. The crystalline Resmetirom: caffeine according to claim 4, which contains no more than about 20% of any other crystalline forms of Resmetirom:caffeine or crystalline Resmetirom: caffeine salt.

10. The crystalline Resmetirom: caffeine according to claim 4, designated form RC2-A which contains no more than about 20% of amorphous Resmetirom:caffeine or Resmetirom: caffeine salt.

11. The crystalline Resmetirom: caffeine according to claim 1, designated form RC2-B, which is characterized by data selected from one or more of the following:
   i) an XRPD pattern having peaks at 8.9, 10.6, 11.2, 14.5 and 17.1 degrees 2-theta±0.2 degrees 2-theta;
   ii) an XRPD pattern as depicted in FIG. 25;
   iii) a solid state $^{13}$C NMR spectrum with characteristic peaks at 145.9, 142.7, 108.7, 33.5 and 28.1 ppm±0.2 ppm;
   iv) a solid state $^{13}$C NMR spectrum having the following chemical shift absolute differences from reference peak at 161.1 ppm±1 ppm: 15.2, 18.45, 52.4, 127.6 and 133.0 ppm±0.1 ppm;
   v) a solid state $^{13}$C NMR spectrum substantially as depicted in FIG. 37, 38 or 39; and
   vi) combinations of these data.

12. The crystalline Resmetirom: caffeine according to claim 11, designated form RC2-B, characterized by the XRPD pattern having peaks at 8.9, 10.6, 11.2, 14.5 and 17.1 degrees 2-theta±0.2 degrees 2-theta, and also having one, two, three or four additional peaks selected from 14.9, 20.0, 21.9, 24.5 and 28.2 degrees two theta±0.2 degrees two theta.

13. The crystalline Resmetirom: caffeine according to claim 11, which is characterized by an X-ray powder diffraction pattern having peaks at 8.9, 10.6, 11.2, 14.5, 14.9, 17.1, 20.0, 21.9, 24.5 and 28.2 degrees 2-theta±0.2 degrees 2-theta.

14. The crystalline Resmetirom: caffeine according to claim 11, wherein the molar ratio of Resmetirom and caffeine is 1:1.

15. The crystalline Resmetirom: caffeine according to claim 11, wherein the crystalline form is an anhydrous form.

16. The crystalline Resmetirom: caffeine according to claim 11, which contains no more than about 20% of any other crystalline forms of Resmetirom:caffeine or crystalline Resmetirom: caffeine salt.

17. The crystalline Resmetirom: caffeine according to claim 11, which contains no more than about 20% of amorphous Resmetirom: caffeine or Resmetirom:caffeine salt.

18. A pharmaceutical composition comprising a crystalline product according to claim 1, and at least one pharmaceutically acceptable excipient.

19. A process for preparing a pharmaceutical composition comprising combining the crystalline Resmetirom: caffeine according to claim 1 with at least one pharmaceutically acceptable excipient.

20. A medicament comprising the crystalline Resmetirom: caffeine according to claim 1.

21. A method of treating non-alcoholic steatohepatitis (NASH), non-alcoholic fatty liver disease (NAFLD) and/or associated dyslipidemias comprising administering a therapeutically effective amount of a crystalline product according to claim 1 to a subject in need of the treatment.

\* \* \* \* \*